United States Patent
Khanal et al.

(10) Patent No.: US 11,389,638 B2
(45) Date of Patent: Jul. 19, 2022

(54) HEMODYNAMIC ASSIST DEVICE

(71) Applicant: Hridaya, Inc., Lancaster, CA (US)

(72) Inventors: Sanjaya Khanal, Lancaster, CA (US); Joseph Kaminski, Campbell, CA (US)

(73) Assignee: Hridaya, Inc., Lancaster, CA (US)

( * ) Notice: Subject to any disclaimer, the term of this patent is extended or adjusted under 35 U.S.C. 154(b) by 351 days.

(21) Appl. No.: 15/902,177

(22) Filed: Feb. 22, 2018

(65) Prior Publication Data

US 2019/0060543 A1 Feb. 28, 2019

Related U.S. Application Data

(63) Continuation-in-part of application No. 15/097,044, filed on Apr. 12, 2016, now Pat. No. 10,149,934.
(Continued)

(51) Int. Cl.
*A61M 1/12* (2006.01)
*A61M 60/148* (2021.01)
(Continued)

(52) U.S. Cl.
CPC ......... *A61M 60/148* (2021.01); *A61B 1/0016* (2013.01); *A61B 1/04* (2013.01);
(Continued)

(58) Field of Classification Search
CPC ..... A61B 17/0057; A61B 1/0016; A61B 1/04; A61B 1/05; A61B 2017/00017;
(Continued)

(56) References Cited

U.S. PATENT DOCUMENTS 5,746,709 A * 5/1998 Rom ................... A61M 1/3621
604/8
5,749,855 A * 5/1998 Reitan ................. A61M 1/1024
604/131
(Continued)

FOREIGN PATENT DOCUMENTS

CN 1224999 A 8/1999
CN 1274293 11/2000
(Continued)

OTHER PUBLICATIONS

International Search Report for PCT/US13/25056, dated Sep. 16, 2013, Hridaya, Inc.

*Primary Examiner* — Amanda K Hulbert
(74) *Attorney, Agent, or Firm* — Novel IP

(57) ABSTRACT

A hemodynamic flow assist device includes a miniature pump, a basket-like cage enclosing and supporting the pump, and a motor to drive the pump. The device is implanted and retrieved in a minimally invasive manner via percutaneous access to a patient's artery. The device has a first, collapsed configuration to assist in implantation and a second, expanded configuration once deployed and active. The device is deployed within a patient's aorta and is secured in place via a self-expanding cage which engages the inner wall of the aorta. The device includes a helical screw pump with self-expanding blades, sensors, and anchoring structures. Also disclosed is a retrieval device to remove the hemodynamic flow assist device once it is no longer needed by the patient and an arterial closure device to close the artery access point after implantation and removal of the hemodynamic flow assist device. The hemodynamic flow assist device helps to increase blood flow in patients suffering from congestive heart failure and awaiting heart transplant.

20 Claims, 39 Drawing Sheets

Related U.S. Application Data which is a continuation of application No. 13/761,544, filed on Feb. 7, 2013, now Pat. No. 9,339,597.

(60) Provisional application No. 62/462,200, filed on Feb. 22, 2017, provisional application No. 61/595,953, filed on Feb. 7, 2012.

(51) Int. Cl.

| | | |
|---|---|---|
| *A61B 1/04* | (2006.01) | |
| *A61B 17/00* | (2006.01) | |
| *A61F 2/82* | (2013.01) | |
| *A61B 1/00* | (2006.01) | |
| *A61M 60/50* | (2021.01) | |
| *A61M 60/135* | (2021.01) | |
| *A61M 60/205* | (2021.01) | |
| *A61M 60/422* | (2021.01) | |
| *A61N 1/39* | (2006.01) | |
| *A61B 1/05* | (2006.01) | |
| *A61N 1/362* | (2006.01) | |
| *A61M 60/40* | (2021.01) | |
| *A61M 60/414* | (2021.01) | |
| *A61M 60/857* | (2021.01) | |
| *A61M 60/871* | (2021.01) | |

(52) U.S. Cl.
CPC ............ *A61B 17/0057* (2013.01); *A61F 2/82* (2013.01); *A61M 60/135* (2021.01); *A61M 60/205* (2021.01); *A61M 60/422* (2021.01); *A61M 60/50* (2021.01); *A61B 1/05* (2013.01); *A61B 2017/00017* (2013.01); *A61B 2017/00022* (2013.01); *A61B 2017/00044* (2013.01); *A61B 2017/00398* (2013.01); *A61B 2017/00606* (2013.01); *A61B 2017/00654* (2013.01); *A61B 2017/00659* (2013.01); *A61B 2017/00685* (2013.01); *A61B 2017/00734* (2013.01); *A61M 60/40* (2021.01); *A61M 60/414* (2021.01); *A61M 60/857* (2021.01); *A61M 60/871* (2021.01); *A61M 2205/0266* (2013.01); *A61M 2205/04* (2013.01); *A61M 2205/103* (2013.01); *A61M 2205/3334* (2013.01); *A61M 2205/50* (2013.01); *A61M 2205/7545* (2013.01); *A61M 2205/8206* (2013.01); *A61M 2230/63* (2013.01); *A61N 1/362* (2013.01); *A61N 1/3956* (2013.01)

(58) Field of Classification Search
CPC ........... A61B 2017/00022; A61B 2017/00044; A61B 2017/00398; A61B 2017/00606; A61B 2017/00654; A61B 2017/00659; A61B 2017/00685; A61B 2017/00734; A61F 2/82; A61M 1/1008; A61M 1/101; A61M 1/1012; A61M 1/1024; A61M 1/1029; A61M 1/1031; A61M 1/1034; A61M 1/1086; A61M 1/122; A61M 1/125; A61M 1/127; A61M 2205/0266; A61M 2205/04; A61M 2205/103; A61M 2205/3334; A61M 2205/50; A61M 2205/7545; A61M 2205/8206; A61M 2230/63; A61N 1/362; A61N 1/3956

See application file for complete search history.

(56) References Cited

U.S. PATENT DOCUMENTS

| | | | | |
|---|---|---|---|---|
| 5,819,736 A | * | 10/1998 | Avny | A61B 1/00147 600/407 |
| 5,911,685 A | * | 6/1999 | Siess | F04D 29/0467 600/16 |
| 5,921,913 A | * | 7/1999 | Siess | F04D 29/0467 600/16 |
| 5,964,694 A | * | 10/1999 | Siess | H02K 5/08 415/900 |
| 6,007,478 A | * | 12/1999 | Siess | A61M 25/0068 600/16 |
| 6,042,347 A | * | 3/2000 | Scholl | A61M 1/1031 417/423.12 |
| 6,083,260 A | * | 7/2000 | Aboul-Hosn | A61M 1/3653 600/16 |
| 6,136,025 A | * | 10/2000 | Barbut | A61F 2/90 604/530 |
| 6,176,822 B1 | * | 1/2001 | Nix | A61M 1/1015 415/900 |
| 6,176,848 B1 | * | 1/2001 | Rau | F04D 29/0467 600/16 |
| 6,210,318 B1 | * | 4/2001 | Lederman | A61M 1/1072 600/18 |
| 6,217,541 B1 | * | 4/2001 | Yu | F04D 1/02 415/900 |
| 6,245,007 B1 | * | 6/2001 | Bedingham | A61M 1/102 600/16 |
| 6,506,202 B1 | * | 1/2003 | Dutta | A61F 2/958 604/103.05 |
| 6,533,716 B1 | * | 3/2003 | Schmitz-Rode | F04D 3/02 600/16 |
| 6,610,004 B2 | * | 8/2003 | Viole | A61M 1/10 600/16 |
| 6,685,621 B2 | | 2/2004 | Bolling | |
| 6,794,789 B2 | * | 9/2004 | Siess | H02K 1/12 310/40 MM |
| 6,889,082 B2 | * | 5/2005 | Bolling | A61M 1/10 607/16 |
| 6,976,996 B1 | | 12/2005 | Aboul-Hosn | |
| 7,011,620 B1 | * | 3/2006 | Siess | H02K 3/47 600/16 |
| 7,022,100 B1 | * | 4/2006 | Aboul-Hosn | A61M 1/125 604/6.11 |
| 7,027,875 B2 | * | 4/2006 | Siess | A61M 25/0662 607/116 |
| 7,125,376 B2 | | 10/2006 | Viole | |
| 7,144,364 B2 | | 12/2006 | Barbut | |
| 7,172,551 B2 | * | 2/2007 | Leasure | A61M 1/1072 600/16 |
| 7,238,151 B2 | * | 7/2007 | Frazier | A61M 1/1015 600/16 |
| 7,241,257 B1 | * | 7/2007 | Ainsworth | A61B 17/00234 600/16 |
| 7,374,531 B1 | * | 5/2008 | Kantrowitz | A61M 1/1072 600/18 |
| 7,393,181 B2 | * | 7/2008 | McBride | F04D 29/026 416/142 |
| 7,438,699 B2 | * | 10/2008 | Pecor | A61M 39/1011 604/6.16 |
| 7,445,592 B2 | * | 11/2008 | Pecor | A61M 5/14276 600/16 |
| 7,458,929 B2 | | 12/2008 | Bolling | |
| 7,462,019 B1 | * | 12/2008 | Allarie | A61M 1/101 417/423.12 |
| 7,468,050 B1 | * | 12/2008 | Kantrowitz | A61M 1/1072 604/96.01 |
| 7,588,531 B2 | | 9/2009 | Bolling | |
| 7,591,778 B2 | | 9/2009 | Bolling | |
| 7,614,997 B2 | | 11/2009 | Bolling | |
| 7,722,568 B2 | * | 5/2010 | Lenker | A61M 25/0662 604/164.03 |
| 7,731,675 B2 | | 6/2010 | Aboul-Hosn | |
| 7,841,976 B2 | * | 11/2010 | McBride | F04D 29/542 600/16 |
| 7,878,967 B1 | * | 2/2011 | Khanal | F04D 3/00 415/71 |
| 7,914,436 B1 | * | 3/2011 | Kung | A61M 1/106 600/18 |
| 7,927,068 B2 | | 4/2011 | McBride | |
| 7,942,804 B2 | * | 5/2011 | Khaw | F04D 29/247 600/16 |

(56) References Cited

U.S. PATENT DOCUMENTS

| | | | |
|---|---|---|---|
| 7,976,452 B2* | 7/2011 | Kantrowitz | A61M 1/1072 600/18 |
| 7,993,260 B2 | 8/2011 | Bolling | |
| 7,998,054 B2 | 8/2011 | Bolling | |
| 7,998,190 B2 | 8/2011 | Gharib | |
| 8,012,079 B2* | 9/2011 | Delgado, III | A61M 1/1072 600/16 |
| 8,092,549 B2* | 1/2012 | Hillis | A61F 2/82 623/23.64 |
| 8,376,707 B2 | 2/2013 | McBride | |
| 8,439,859 B2 | 5/2013 | Pfeffer | |
| 8,449,443 B2 | 5/2013 | Rodefeld | |
| 8,489,190 B2* | 7/2013 | Pfeffer | A61M 1/1029 607/37 |
| 8,535,211 B2* | 9/2013 | Campbell | A61M 1/101 600/16 |
| 8,562,509 B2* | 10/2013 | Bates | A61F 2/01 600/16 |
| 8,585,572 B2* | 11/2013 | Mehmanesh | A61M 1/1072 600/18 |
| 8,684,904 B2 | 4/2014 | Campbell | |
| 8,690,749 B1* | 4/2014 | Nunez | A61M 1/101 600/16 |
| 8,721,517 B2* | 5/2014 | Zeng | A61M 1/101 600/19 |
| 8,727,959 B2 | 5/2014 | Reitan | |
| 8,814,933 B2* | 8/2014 | Siess | A61M 1/101 623/3.13 |
| 2003/0233143 A1* | 12/2003 | Gharib | A61M 1/10 623/3.1 |
| 2007/0179527 A1 | 8/2007 | Eskuri | |
| 2009/0093796 A1* | 4/2009 | Pfeffer | A61M 25/0074 604/530 |
| 2009/0118567 A1* | 5/2009 | Siess | F04D 29/406 600/16 |
| 2010/0041939 A1* | 2/2010 | Siess | F04D 13/0626 600/16 |
| 2010/0114156 A1 | 5/2010 | Mehl | |
| 2010/0114159 A1 | 5/2010 | Roorda | |
| 2010/0249907 A1* | 9/2010 | Dorn | A61F 2/962 623/1.23 |
| 2011/0082495 A1* | 4/2011 | Ruiz | A61B 17/0057 606/213 |
| 2011/0184224 A1* | 7/2011 | Garrigue | A61M 1/125 600/16 |
| 2011/0257462 A1* | 10/2011 | Rodefeld | A61M 1/1024 600/16 |
| 2011/0282128 A1* | 11/2011 | Reitan | A61M 1/12 600/16 |
| 2012/0041255 A1 | 2/2012 | Delgado | |
| 2014/0088340 A1* | 3/2014 | Kantrowitz | A61M 1/12 600/18 |

FOREIGN PATENT DOCUMENTS

| | | |
|---|---|---|
| CN | 1972725 | 5/2007 |
| CN | 101410064 A | 4/2009 |
| CN | 104039245 A | 9/2014 |
| EP | 2016961 | 2/2010 |
| EP | 2310067 | 4/2014 |
| JP | H04126158 | 4/1992 |
| WO | 2003103745 | 4/2004 |
| WO | 2005102414 | 11/2005 |
| WO | 2006111954 | 10/2006 |
| WO | 2008071952 A2 | 6/2008 |
| WO | 2010149393 A1 | 12/2010 |
| WO | 2011089022 | 7/2011 |
| WO | 2013119752 | 8/2013 |

* cited by examiner

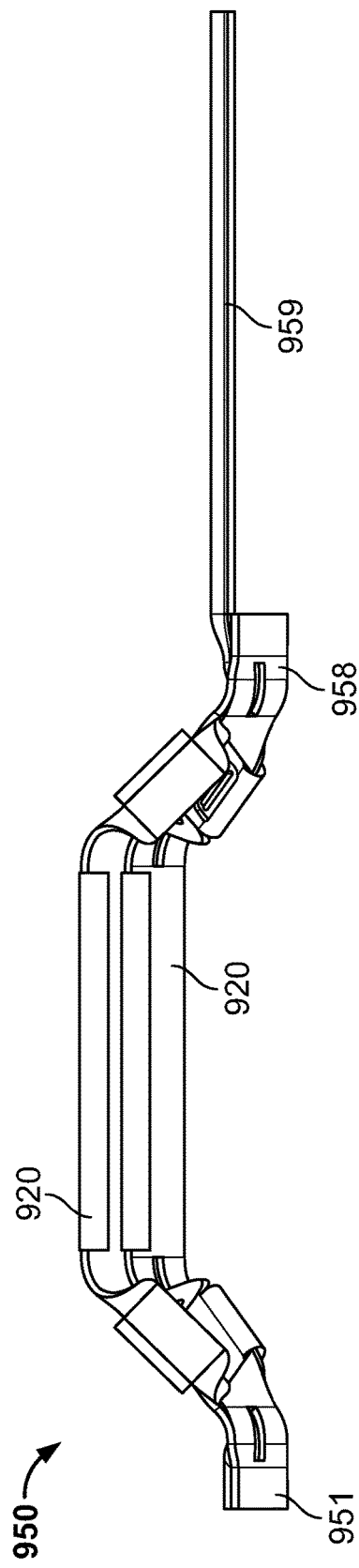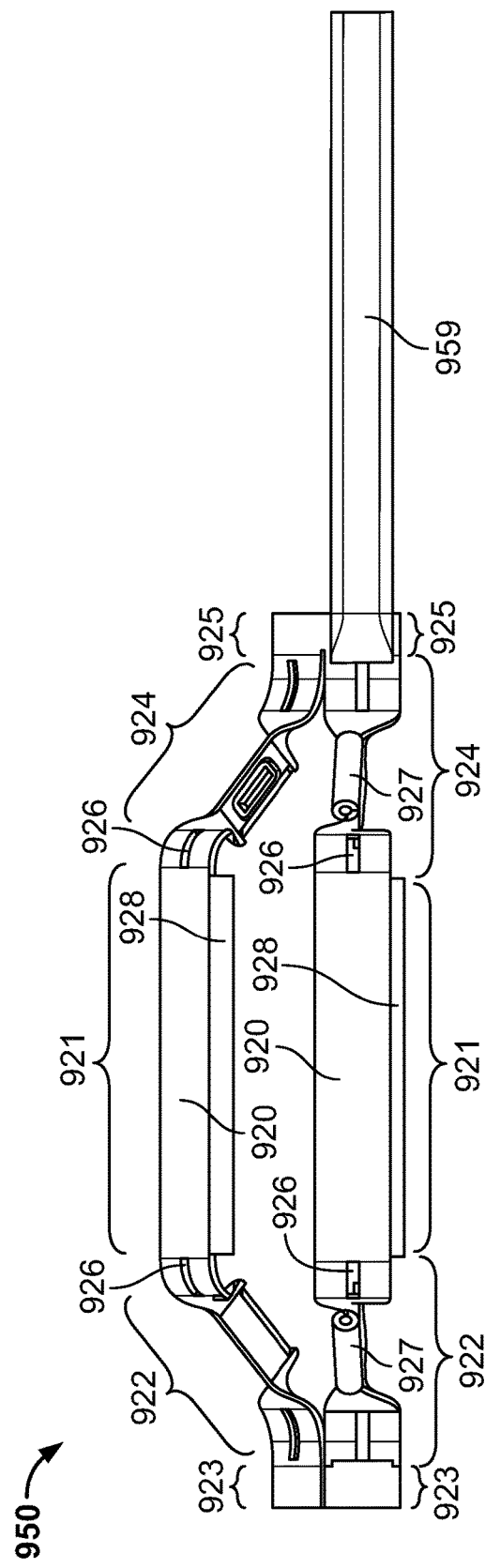

HEMODYNAMIC ASSIST DEVICE

CROSS-REFERENCE

The present application relies on U.S. Patent Provisional Application No. 62/462,200, entitled "Hemodynamic Assist Device" and filed on Feb. 22, 2017, for priority.

The present application is also a continuation-in-part application of U.S. patent application Ser. No. 15/097,044, entitled "ARTERIAL CLOSURE DEVICE", filed on Apr. 12, 2016, and issued as U.S. Pat. No. 10,149,934 on Dec. 11, 2018, which is a continuation application of U.S. patent application Ser. No. 13/761,544, entitled "Hemodynamic Assist Device", filed on Feb. 7, 2013, and issued as U.S. Pat. No. 9,339,597 on May 17, 2016, which, in turn, relies on U.S. Patent Provisional Application Number 61/595,953, of the same title and filed on Feb. 7, 2012, for priority.

All of the abovementioned applications are hereby incorporated by reference in their entirety.

FIELD

The present specification relates generally to cardiovascular flow assist devices. More particularly, the present specification relates to an intravascular, collapsible pumping device that is implanted and removed in a minimally invasive manner and which acts to increase blood flow in hemodynamically compromised patients.

BACKGROUND

Heart failure is defined as a condition in which a person's heart is no longer capable of supplying adequate blood flow to meet the needs of the body. Congestive heart failure (CHF) refers to a condition wherein the heart does not transfer blood to end organs efficiently or it has to do so with increased filling pressures. CHF, rather than being its own disease, occurs as a result of any one, or combination, of a number of conditions which affect the heart, including, but not limited to, myocardial infarction, dilated cardiomyopathy, valvular heart disease, hypertension, obesity, diabetes, and cigarette smoking. All of these conditions can lead to CHF by overloading or causing damage to the heart muscle.

It has been estimated that nearly 5 million Americans have CHF. Increasing prevalence, hospitalizations, and deaths have made CHF a major chronic condition in the United States and throughout the world. After the diagnosis of CHF, the death rate is 50% within 5 years. Each year, there are more than 400,000 new cases in the United States alone. The prevalence of CHF is increasing as the population ages.

Therapies for patients suffering from CHF include medical, surgical, and biopharmaceutical (for example, growth factors, cytokines, myoblasts, and stem cells). Improvement in prognosis through medical therapy has reached a ceiling. There is widespread thought that current medical therapies cannot be effectively expanded upon. Heart transplant is an effective surgical remedy for patients with CHF. However, the demand far outstrips the availability of donor hearts. Therefore, a mechanical solution is sorely needed to treat heart failure.

Typically for mechanical treatment of CHF, a pump such as a ventricular assist device (VAD) is implanted in a patient awaiting a heart transplant. The VAD is implanted as a "bridge to transplant" or "destination therapy" for those weakened hearts that are expected to become unable to pump enough blood to sustain life. A VAD is typically attached to the left ventricle and draws blood from the left ventricle and sends the blood to the aorta.

A number of other devices have been proposed for assisting the diseased heart and supporting decompensated hemodynamics. For example, U.S. Pat. No. 5,911,685, assigned to Impella Cardiosystems AG, describes "An intravascular microaxial flow pump, comprising: a cylindrical drive unit of preselected outer diameter having an electric motor disposed therein driving a shaft distally extending therefrom wherein such shaft is supported solely by two bearings, one located at the extreme proximal end of said drive unit and another at the extreme distal end of said drive unit; a cylindrical intravascular microaxial flow pump housing rigidly attached to said drive unit having essentially the same preselected outer diameter and oriented to be coaxially and distally disposed with respect to said drive unit; and an impeller disposed within said pump housing, rigidly affixed to said shaft, and located immediately adjacent said distal bearing, operative to draw fluid into and through said housing and over said drive unit."

In addition, U.S. Pat. No. 7,125,376, assigned to Thoratec Corporation, describes "An intravascular extracardiac pumping system for supplementing blood circulation through a patient experiencing congestive heart failure without any component thereof being connected to the patient's heart, the extracardiac system comprising: a pump configured to pump blood through the patient at subcardiac volumetric rates, said pump having an average flow rate that, during normal operation thereof, is substantially below that of the patient's heart when healthy, the pump configured to be positioned within the vasculature of a patient; an inflow conduit fluidly coupled to the pump to direct blood to the pump, the inflow conduit configured to be positioned within the vasculature of the patient; and an outflow conduit fluidly coupled to the pump to direct blood away from the pump, the outflow conduit configured to be positioned within the vasculature of the patient; whereby the pump and the inflow and outflow conduits are configured so as to be inserted subcutaneously into the vasculature in an minimally-invasive procedure; and wherein the pump comprises an impeller."

A cardiac recovery is possible for patients who suffer from CHF, especially through treatment with biopharmaceuticals. The likelihood of cardiac recovery is believed to be increased by reducing the stress on the heart from the decompensated state. However, the existence of a VAD surgically inserted into the heart reduces the likelihood of cardiac recovery from CHF. The gold standard for treatment of advanced heart failure is a heart transplant but the scarcity of transplantable hearts makes this impossible for the vast majority of patients.

Therefore, there exists a need for a hemodynamic assist device that can be implanted and retrieved in a minimally invasive manner, without damaging the heart and preventing cardiac recovery.

SUMMARY

The present specification discloses a retrievable intravascular hemodynamic flow assist device comprising: a pump comprising: a plurality of collapsible blades attached to a rotatable shaft; and a motor configured to coaxially rotate said shaft; a collapsible cage enclosing said pump; and an engagement mechanism configured to engage said pump with said cage; wherein said device has a first diameter in an undeployed configuration and a second diameter in a deployed configuration, wherein the second diameter is greater than the first diameter, wherein said blades and said cage are positioned against said shaft when the device is in the undeployed configuration, and wherein said blades expand away from said shaft and said cage expands away from said shaft to surround said blades when the device is in said deployed configuration, and wherein said engagement mechanism is configured to disengage said pump from said cage, upon activation of a release mechanism, such that said pump is capable of being retrieved from a blood vessel of a patient while said cage remains within said blood vessel.

Optionally, said engagement mechanism comprises at least one hook.

Optionally, said engagement mechanism is provided at a junction of said pump with said cage.

Optionally, said cage is configured to function as a stent after retrieval of said pump.

Optionally, said cage comprises a plurality of cage support members comprising a plurality of struts, proximal and distal hinge portions, and proximal and distal connectors. Optionally, each of said plurality of struts is rectangular shaped and links one of said plurality of proximal hinge portions with one of said plurality of distal hinge portions to allow for compression and expansion of said cage as said device changes from said undeployed configuration to said deployed configuration. Optionally, each of said plurality of proximal connectors comprises a first end and a second end wherein said first end and second end are secured to proximal ends of adjacent struts of said plurality of struts and each of said plurality of distal connectors comprises a first end and a second end and said first end and second end are secured to distal ends of adjacent struts of said plurality of struts to create a contiguous structure at a proximal end and a distal end of the cage. Optionally, each of said plurality of connectors is welded to each of said plurality of struts. Optionally, said plurality of struts, proximal and distal hinge portions, and proximal and distal connectors are laser cut from a single Nitinol cylinder. The cage may comprise eight support members.

Optionally, said release mechanism comprises a central release mechanism positioned within said shaft and is controlled from a proximal end of said shaft.

Optionally, said engagement mechanism comprises a plurality of proximal couplers and a plurality of distal couplers configured to secure said pump to said cage. Optionally, said shaft is elongated to release said plurality of proximal couplers and said plurality of distal couplers.

Optionally, said intravascular hemodynamic flow assist device further comprises a proximal cap and a distal cap, wherein said engagement mechanism comprises a plurality of convex bevels on an outer surface of proximal and distal ends of said struts which are configured to dislodge from a plurality of concave repositories inside said proximal and distal caps when said shaft is elongated.

Optionally, said intravascular hemodynamic flow assist device further comprises at least one sensor and a microprocessor, wherein said at least one sensor and microprocessor are configured to monitor data representative of a shape and size of said cage in said deployed configuration and said microprocessor is configured to control said motor to adjust a shape and size of said cage based on said data.

Optionally, said cage is configured to remain in a blood vessel for a period up to six months after retrieval of said pump.

The present specification also discloses a retrievable intravascular hemodynamic flow assist device comprising: a retrievable helical screw pump comprising: a first shaft having a lumen, a proximal end, and a distal end, said first shaft comprising a plurality of blades forming a helical screw pump; a second shaft having a proximal end and a distal end, wherein a portion of said proximal end of said second shaft is disposed within, and configured to telescope into and out of, a portion said lumen of said first shaft at the distal end of said first shaft; and a motor positioned at said proximal end of said first shaft for coaxially rotating said first shaft and said blades about said second shaft to pump blood through the device; a cage enclosing said helical screw pump and comprising a plurality of cage support members; and an engagement mechanism configured to engage said helical screw pump with said cage; wherein said device has a first diameter in an undeployed configuration and a second diameter in a deployed configuration, wherein the second diameter is greater than the first diameter, wherein said plurality of blades and said plurality of cage support members are positioned against said first shaft when the device is in the undeployed configuration, and wherein said blades expand away from said first shaft and said cage support members expand away from said first shaft to form a cage surrounding said blades when the device is in said deployed configuration, and wherein said engagement mechanism is configured to disengage said helical screw pump from said cage, upon activation of a release mechanism, such that said helical screw pump is capable of being retrieved from a blood vessel of a patient while said cage remains within said blood vessel.

The present specification also discloses a retrievable intravascular hemodynamic flow assist device comprising: a retrievable helical screw pump comprising: a first shaft having a lumen, a proximal end, and a distal end, said first shaft comprising a plurality of blades forming a helical screw pump; a second shaft having a proximal end and a distal end, wherein a portion of said proximal end of said second shaft is disposed within, and configured to telescope into and out of, a portion said lumen of said first shaft at the distal end of said first shaft; and a motor positioned at said proximal end of said first shaft for coaxially rotating said first shaft and said blades about said second shaft to pump blood through the device; a stent enclosing said helical screw pump; and an engagement mechanism configured to engage said helical screw pump with said stent, wherein said engagement mechanism is configured to disengage said pump from said stent, upon activation of a release mechanism, such that said pump is capable of being retrieved from a blood vessel of a patient while said stent remains within said blood vessel.

Optionally, said engagement mechanism comprises at least a first hook positioned on a proximal end of said stent and at least a second hook positioned on a distal end of said stent and wherein each of the at least one first hook and at least one second hook is configured to engage with a plurality of recesses positioned in a proximal end of the helical screw pump and a distal end of the helical screw pump respectively.

Optionally, said engagement mechanism comprises a plurality of magnets of opposing poles positioned on said stent and on said helical screw pump.

The present specification also discloses an intravascular, hemodynamic flow assist device, comprising: a miniature helical screw pump with at least one collapsible blade; a collapsible cage structure surrounding said pump; and, a motor to drive said pump; wherein said device transforms from a first, collapsed configuration to a second expanded configuration, wherein the diameter of the first configuration is smaller than the diameter of the second configuration, and further wherein said device is converted into said first configuration during implantation and retrieval and converted into said second configuration for deployment and operation.

Optionally, the intravascular hemodynamic flow assist device comprises a first shaft having a lumen, a proximal end, and a distal end; a second shaft having a proximal end and a distal end, wherein a portion of said proximal end of said second shaft is disposed within, and configured to telescope into and out of, a portion of said lumen of said first shaft at the distal end of said first shaft; at least one set of pump blades adapted to expand to an expanded configuration from a first collapsed configuration and collapse from the expanded configuration back to said first collapsed configuration, wherein said at least one set of pump blades is attached to said first shaft and arranged such that said first shaft has the form of a helical screw pump; a motor attached to said proximal end of said first shaft for coaxially rotating said first shaft and said blades about said second shaft to pump blood through the device; a housing encircling and containing said motor; a cap attached to said distal end of said second shaft; a plurality of arms each having a proximal end and a distal end, wherein said proximal end of each of said plurality of arms is attached to said housing and wherein said distal end of each of said plurality of arms is attached to said cap; and a battery contained within said housing providing power to said motor, wherein said device is transformable between the first collapsed configuration and the expanded configuration, wherein the diameter of the first collapsed configuration is smaller than the diameter of the second expanded configuration, wherein said blades and said arms are compressed against said first shaft when the device is in the first collapsed configuration, and wherein said blades expand away from said first shaft and said arms expand away from said first shaft to form a cage surrounding said blades when the device is in said expanded configuration.

Optionally, the hemodynamic flow assist device further comprises a wire attached to said motor, wherein said wire provides power and/or control from a power and/or control device external to a patient. The blades and portions of said arms comprise a shape memory metal. The shape memory metal is Nitinol. The hemodynamic flow assist device further comprises a coupling positioned between said proximal end of said first shaft and said motor for transferring rotation to said first shaft.

Optionally, the hemodynamic flow assist device further comprises at least one sensor for sensing a functional parameter of said device and/or a physiological parameter of a patient, wherein data from said sensor is transmitted to a controller and wherein said controller uses said data to control said device. The hemodynamic flow assist device further comprises at least one camera. The hemodynamic flow assist device further comprises a mechanism for changing a size of said cage based on the size of a patient's aorta. The first shaft further comprises a plurality of compression rings to allow for deformation of the first shaft during placement.

Optionally, the hemodynamic flow assist device further comprises a compressible tubular cylinder having a lumen for directing blood flow into said device, wherein said cylinder is positioned within said cage and is attached to said second shaft by at least one strut, further wherein said cylinder is compressed against said first shaft when said device is in said first collapsed configuration. The hemodynamic flow assist device further comprises a self-charging battery or inverter, wherein said self-charging battery is charged by the unassisted flow of blood turning said blades when a patient having said device implanted is in the resting position.

Optionally, the hemodynamic flow assist device further comprises an accelerometer, wherein said accelerometer detects a position of a patient and generates data indicative of said position, and wherein a controller receives said data and causes a rotational speed of the device to adjust accordingly. The cage has a cone shape configured to resist dislodgement within a patient's aorta.

Optionally, an intravascular hemodynamic flow assist device comprises: a first shaft having a lumen, a proximal end, and a distal end; a second shaft having a proximal end and a distal end, wherein a portion of said proximal end of said second shaft is disposed within, and configured to telescope into and out of, a portion said lumen of said first shaft at the distal end of said first shaft; at least one set of collapsible pump blades attached to said first shaft, said blades arranged such that said first shaft forms a helical screw pump; a motor attached to said proximal end of said first shaft for coaxially rotating said first shaft and said at least one set of collapsible blades about said second shaft to pump blood through the device; a housing encircling and containing said motor; a cap attached to said distal end of said second shaft; an elongate, collapsible tubular cylinder having a lumen, a proximal end, and a distal end, wherein said cylinder is attached to said second shaft by a plurality of struts; and, a battery contained within said housing providing power to said motor.

Optionally, an intravascular hemodynamic flow assist device comprises a first shaft having a lumen, a proximal end, and a distal end; a second shaft having a proximal end and a distal end, wherein a portion of said proximal end of said second shaft is disposed within, and configured to, telescope into and out of, a portion said lumen of said first shaft at the distal end of said first shaft; a first bearing coupled to and coaxially rotatable about said proximal end of said first shaft; a second bearing coupled to and coaxially rotatable about said distal end of said second shaft; at least one set of collapsible pump blades attached at a first end to said first bearing and at a second end to said second bearing, said blades arranged such that said first shaft and second shafts form a helical screw pump; a housing attached to said proximal end of said first shaft; a cap attached to said distal end of said second shaft; and, a plurality of arms each having a proximal end and a distal end, wherein said proximal end of each of said plurality of arms is attached to said housing and wherein said distal end of each of said plurality of arms is attached to said cap; wherein portions of said arms are magnetically charged and cause said blades to spin via magnetic coupling; wherein said device is transformable between a first, collapsed configuration and a second expanded configuration, wherein the diameter of the first configuration is smaller than the diameter of the second configuration, further wherein said device is converted into said first configuration during implantation and retrieval and converted into said second configuration for deployment and operation, further wherein said second shaft partially telescopes distally out of said first shaft and said blades and said arms are compressed against said first shaft when the device is in said first configuration, further wherein said second shaft partially telescopes proximally into said first shaft, said blades expand away from said first shaft, and said arms expand away from said first shaft to form a cage surrounding said blades when the device is in said second configuration, still further wherein said arms contact an inner wall of an aorta to hold the device in place.

The present specification also discloses a method of implanting the hemodynamic flow assist devices disclosed above, where the method comprises: providing a tubular sheath having a lumen, a proximal end, a distal end, and a guide wire disposed within said lumen; creating an access point into an artery of a patient; inserting said sheath and wire into said artery and advancing it such that said distal end of said sheath is positioned within said patient's descending aorta; inserting said flow assist device, in said first configuration, into said sheath and advancing it along said guide wire to said distal end of said sheath; providing a positioning device comprising an elongate flexible shaft having a proximal end and a distal end, wherein said distal end is coupled to said housing of said flow assist device and said proximal end is manipulated by a physician; using said positioning device to advance said flow assist device beyond said distal end of said sheath and to position said flow assist device within said patient's aorta, wherein said flow assist device passively expands from said first configuration to said second configuration once it is beyond said distal end of said sheath; uncoupling said positioning device from said flow assist device and removing said positioning device and said sheath from said aorta via said artery; and, closing said access point in said artery.

Optionally, the artery is any one of a femoral, external iliac, common iliac, subclavian, brachial, and axillary artery. The flow assist device is positioned within said descending aorta between a left subclavian artery and a point distal a renal artery.

The specification also discloses a blood vessel closure device comprising: an elongate tubular sheath having a sheath lumen, a proximal end, and a distal end; an elongate tamper tool disposed within said sheath lumen and having a tool lumen, a proximal end, and a distal end wherein said distal end of said tool is positioned proximate and within said distal end of said sheath and said proximal end of said tool extends beyond said proximal end of said sheath, further wherein said tool includes a handle at said proximal end; and a pair of compressible discs positioned within said distal end of said sheath distal to and in contact with said distal end of said tool, said discs connected by a center member and transformable between a first configuration and a second configuration, wherein said discs are compressed and have a tubular shape when in said first configuration and are expanded and have an umbrella shape when in said second configuration, further wherein said discs are deployable beyond said distal end of said sheath by pushing on said handle of said tool such that said tool moves distally into said sheath and pushes out said discs; further wherein said discs are in said first configuration when disposed within said sheath and are in said second configuration when advanced beyond said distal end of said sheath; wherein, when said discs are deployed in said second configuration, a first distal disc is positioned within a blood vessel and a second proximal disc is positioned outside the blood vessel with the center member occluding an opening in a wall of said blood vessel.

The present specification also discloses a method of closing an opening in a blood vessel wall using the closure device disclosed above, where the method comprises the steps of: providing a guide wire having a proximal end and a distal end; inserting a said distal end of said guide wire into said blood vessel through said opening; inserting said proximal end of said guide wire into said tool lumen and advancing said closure device along said guide wire; positioning said distal end of said sheath in the interior of said blood vessel; pushing on said handle of said tool of said closure device to advance a distal disc beyond said distal end of said sheath, said distal disc passively expanding into said second configuration within said blood vessel; pulling back on said closure device to position said distal disc against an inner wall of said blood vessel; pushing on said handle of said tool of said closure device to advance a proximal disc beyond said distal end of said sheath, said proximal disc passively expanding into said second configuration outside of said blood vessel and resting against an outer wall of said blood vessel such that the distal and proximal discs and center member act to occlude said opening in said blood vessel; and, removing said sheath with said tool and said guidewire.

Optionally, the method further comprises removing from the patient said second shaft, said at least one set of pump blades, said motor, battery and said cap; and keeping said plurality of arms, wherein said plurality of arms are configured to function as a stent.

Optionally, the intravascular hemodynamic flow assist device may further comprise at least one of a camera and a sensor. Optionally, said sensor is at least one of an accelerometer sensor, a flow meter sensor, and an EKG sensor. Optionally, said accelerometer generates activity data and wherein a rotational speed of said motor is modulated based upon said activity data. Optionally, said flow meter generates data indicative of blood flow and wherein a rotational speed of said motor is modulated based upon said data indicative of blood flow.

Optionally, said battery is configured to be charged by a movement of said at least one set of pump blades caused by a flow of blood when the motor is off.

Optionally, the intravascular hemodynamic flow assist device may further comprise hooks on said plurality of arms to resist dislodgement within a patient's aorta.

Optionally, the intravascular hemodynamic flow assist device may further comprise a bifurcated anchor to resist dislodgement within a patient's aorta, wherein said bifurcated anchor comprises two arms and wherein each arm is configured to respectively sit within each branch of an aortic bifurcation.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 9B is a side view illustration of the same embodiment of two cage support members formed together into a singular cage arm in the expanded configuration of FIG. 9A;

FIG. 9C is a top-down view illustration of the same embodiment of two cage support members formed together into a singular cage arm in the expanded configuration of FIG. 9A;

DETAILED DESCRIPTION

Figure 1:
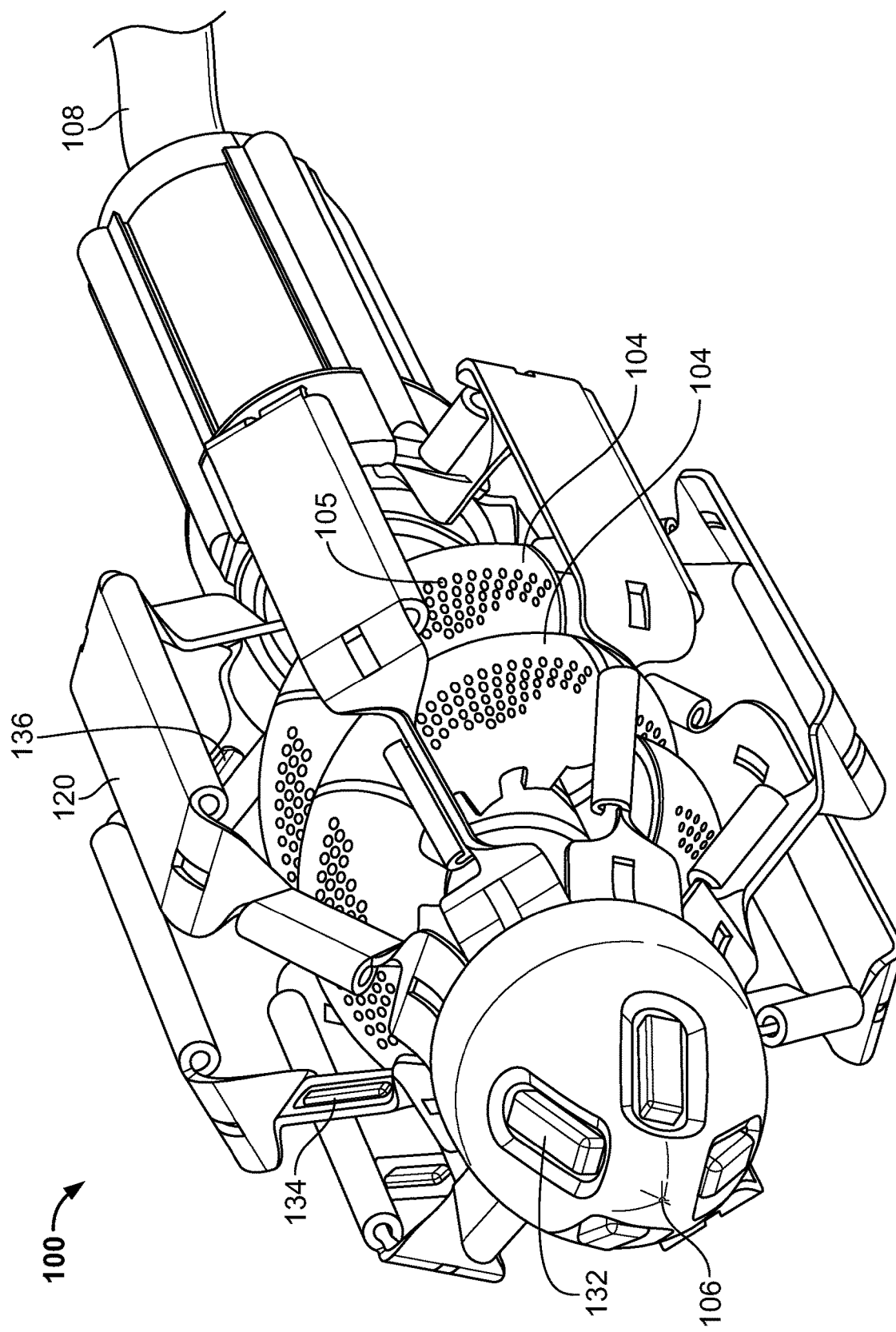
FIG. 1 is an oblique front view illustration of one embodiment of the cardiovascular flow assist device in the expanded, deployed configuration.

The present specification is directed toward an intravascular, collapsible pumping device that is implanted and removed in a minimally invasive manner and which acts to increase blood flow in hemodynamically compromised patients. The device is positioned within the aorta, downstream of the aortic arch, and offloads the diseased heart by increasing systemic blood flow. In one embodiment, the device is an elongate, cylindrically-shaped device with a proximal end and a distal end, comprising a miniature pump, a basket-like cage enclosing said pump, and a motor to drive the pump. In one embodiment, power for the motor is supplied by an internal battery. In another embodiment, at least one wire extends from the proximal end of the device and provides power to the device. Optionally, in one embodiment, the wire also provides control for the device. In another embodiment a wireless Radio Frequency (RF) system is embedded within the device for wireless electromagnetic powering of the device.

In one embodiment, the device includes a cap at its distal end. In one embodiment, the pump is a helical screw pump, such as an Archimedes' pump, comprising a rotating shaft with at least one set of collapsible pump blades attached thereto. In one embodiment, the rotating shaft comprises an inner portion and an outer portion, wherein the inner portion is capable of slidable movement partially into and out of the outer portion. In one embodiment, preloaded compression separating rings on the shaft provide fluid tight seals and allow for any axial displacement introduced by flexible coupling and pressure on the pump blades. The cage is comprised of a multitude of support members and provides support to the pump and anchors the pump within the descending aorta. The pump blades and portions of the cage support members are composed of a shape memory metal that allows the device to change from a first, deliverable and collapsed configuration into a second, deployed and expanded configuration. In one embodiment, the pump blades and portions of each support member are composed of Nitinol. In one embodiment, as the device is collapsed, the inner portion of the rotating shaft extends partially from the outer portion, causing the device to become elongated when in the collapsed configuration. At the same time, the pump blades and cage support members collapse in toward the center of the device, resulting in the total diameter of the device being decreased while in the collapsible configuration.

In one embodiment, the intravascular, collapsible pumping device of the present specification includes at least one sensor. In one embodiment, the sensor is a full 3D space profile pressure quad-sensor. In another embodiment, the sensor is an inflow quad-sensor. In another embodiment, the sensor is a temperature and outflow quad-sensor. The sensor is used to relay information regarding the initial positioning and initial aortic wall proximity, based on differentials of comparable sensor pairs at any stage of the device. In one embodiment, the sensor provides the health care professional with vital device functionality information. In another embodiment, the device includes two or more sensors positioned at different locations along the length of the device. In one embodiment, a first sensor is positioned proximate the distal end of the device and a second sensor is positioned proximate the proximal end of the device. Differences in values measured between the first sensor and the second sensor are used to determine rates of flow and functionality of the device. In one embodiment, the intravascular, collapsible pumping device of the present specification includes at least one camera. In one embodiment, the camera is positioned proximate the distal end of the device. In one embodiment, the camera is an infra-red (IR) charged coupled device (CCD) camera.

In one embodiment, the device is implanted percutaneously through a patient's artery. In one embodiment, the device is introduced via the femoral artery. In another embodiment, the device is introduced via the external iliac artery. In another embodiment, the device is introduced via the common iliac artery. In yet another embodiment, the device is introduced via the axillary or subclavian artery. In one embodiment, a puncture is made in the patient's thigh area and a sheath is introduced into the femoral artery and its distal end is positioned in the aorta. The device is mechanically inserted into the sheath. The sheath has a diameter that is smaller than the diameter of the device in its expanded configuration and is larger than the diameter of the device in its collapsed configuration. In one embodiment, the act of inserting the device into the sheath causes the device to compress into its collapsed configuration. The sheath and collapsed device are advanced into the patient's aorta to the desired deployment location. In one embodiment, the device is deployed in the descending aorta just downstream from the left subclavian artery. In another embodiment, the device is deployed in the descending aorta just downstream from the renal arteries. In various other embodiments, the device is deployed anywhere along the descending aorta between the left subclavian artery and just downstream from the renal arteries, with care taken not to occlude any branches contained therewithin. In various other embodiments, access is obtained through the subclavian, axillary or brachial or radial arteries.

Once the sheath and device have reached the desired deployment location, the sheath is retracted while the device is held in place by an attached positioning shaft. The positioning shaft is an elongate, flexible, solid shaft having a proximal end and a distal end. The distal end of the shaft attaches to the proximal end of the device with either a screw or clip and the shaft traverses the entire length of the sheath. The proximal end of the shaft exits from the proximal end of the sheath and includes a proximal knob that can be manipulated outside the sheath. The shaft is detached from the device via an unlock mechanism after the device is positioned appropriately. In one embodiment, once the sheath has cleared the device, the pump blades and cage support members expand and the inner portion of the rotating shaft telescopes partly into the outer portion of said shaft. In another embodiment, a distal portion of the rotating shaft extends partially into the distal cap when in the expanded configuration. In this embodiment, the distal cap comprises a fluid filled cavity to accommodate a distal portion of the rotating shaft. The fluid is eliminated when the cage expands. As the device changes into its deployed, expanded configuration, its length shortens and diameter increases. The cage support members come to rest upon the walls of the aorta and the rotating shaft with attached pump blades is free to spin within the cage. The positioning shaft is disengaged from the proximal end of the device and removed from the sheath. The sheath is then removed from the patient. In an embodiment in which the device has an internal battery, the puncture site is sutured close. In an alternate embodiment, in which the device includes a power and/or control wire, said wire extends from the puncture site and is secured at the patient's skin. In one embodiment, the wire extends to a battery and/or control pack which sits in a belt or vest at the belt level.

The present specification is also directed toward a retrieval device used to remove the pumping device from the patient's aorta. In one embodiment, the retrieval device is similar to the one described in U.S. Pat. No. 7,878,967, entitled "Heart Failure/Hemodynamic Device" and assigned to the applicant of the present invention, which is hereby incorporated in its entirety. In one embodiment, when the pumping device is ready to be removed, a sheath is once again introduced percutaneously into the femoral artery using the power and/or control wire, if remaining. In another embodiment, the control and the power wires comprise at least two separate wires coming from diagonally opposite ends of the proximal portion of the device. The removal device is then inserted into the sheath and both are advanced through the vasculature into the descending aorta and up to the pumping device. The retrieval device is then advanced further beyond the end of the sheath. The distal end of the retrieval device interfaces with the proximal end of the pumping device such that the pumping device becomes connected to the retrieval device. This connection can be a mechanical locking mechanism or magnetically assisted. The retrieval device is then retracted back into the sheath, bringing the pumping device with it. The attached proximal wires and enclosing wires jacket that, in one embodiment, is reinforced for added strength can be used to pull the device into the sheath. As the cage comes into contact with the sheath, the support members are compressed back toward the center of the pumping device. Compression of the cage causes the inner portion of the rotating shaft to partially extend out from the outer portion of said rotating shaft. In another embodiment, wherein the distal cap comprises a cavity to house a distal portion of the shaft, the distal cap extends away from the shaft and said cavity fills with blood during retrieval. In one embodiment, as the cage gradually collapses, the shaft with helical pump blades rotates reversely. The initial blade shape and the fully expanded blade shape are developed with a blade profile such that when rotated reversely allow the blades to be deformed and take a similar shape as in the insertion stage. In one embodiment, the inner construction and details of the enclosed cage will provide further support and guidance to the pump blades to assist in their deformation and effectively place them in the inside space of the compressed cage. Compression of the cage support members and extension of the rotating shaft inner portion result in collapse of the helical pump blades. Pulling of the pumping device into the sheath via the attached retrieval device causes the pumping device to revert back to its collapsed, retrievable configuration. Once fully withdrawn into the sheath, the pumping device, along with the attached retrieval device and sheath, is removed through the femoral artery and the access site is sutured closed. In one embodiment, a sieve-like filter is attached to the distal end of the retrieval device. This circular filter is deployed when the retrieval device is extended beyond the distal end of the sheath. The filter traps any debris that is dislodged in the process of retrieving the pumping device. The filter then also collapses into the sheath along with the device after the device is retracted into the sheath.

In one embodiment, retrieval of the device employs two wires attached to the proximal end of the pumping device. A retrieval device is inserted into the access vessel using the two wires as rails to guide the retrieval device to the pumping device. In one embodiment, the wires can be used to elongate the shaft of the pumping device when put on tension, thereby collapsing the device prior to retrieval.

In another embodiment, wherein the pumping device includes an internal battery and no wires extend from the body of the patient, retrieval of the device employs magnetism. The proximal end of the pumping device and the distal end of the retrieval device are magnetized with opposite polarities so that the two will connect when the retrieval device is advanced to the deployed pumping device.

Optionally, in one embodiment, the rotating shaft of the pump is comprised of a stretchable material rather than inner and outer portions. When the device is collapsed, the shaft stretches, increasing the length of the device. Once released from the insertion sheath, the shaft contracts to its default shape. In this embodiment, the at least one set of blades is attached only at the proximal and distal ends of the shaft. As the shaft is stretched, the blades and cage support members stretch and compress toward the center of said shaft. As the shaft contracts to its default shape, the blades return to their operable, expanded configuration.

Optionally, in one embodiment, the at least one set of blades is attached only to bearings positioned at the proximal and distal ends of the shaft. In this embodiment, only the blades rotate with the bearings. In one embodiment, the blades are rotated via magnetic coupling. The shaft does not rotate, resulting in fewer moving parts and lower power consumption. This embodiment can be utilized on a telescoping shaft or a stretchable shaft as described above.

Optionally, in one embodiment, the basket-like cage acts as a stator and rotates the blades such that the entire helical blade set(s) and cage are magnetically active and become a rotor of the coreless motor, eliminating the need for an electric motor at the proximal end of the device. In this embodiment, the blades are composed of a magnetic field material and the cage components possess the ability to electrically induce a polarized magnetic field.

Optionally, in one embodiment, the device includes a collapsible, continuous cylinder positioned just within the cage. The cylinder is open at its distal and proximal ends to allow for the passage of blood. The space between the blades of the pump and the cylinder is minimal, improving the efficiency of the device by decreasing the amount of leakage around the blades. In one embodiment, the blades and the cylinder are like charged so that the cylinder would be magnetically levitated and not come into contact with the blades.

Optionally, in one embodiment, the device includes a collapsible, continuous cylinder in place of the basket-like cage. The cylinder is open at its distal and proximal ends to allow for the passage of blood. The outside circumference of the cylinder rests upon the inner wall of the aorta. In one embodiment, the cylinder is attached to the device via collapsible struts. The space between the blades of the pump and the cylinder is minimal, improving the efficiency of the device by decreasing the amount of leakage around the blades.

Optionally, in one embodiment, the device includes a mechanism to adjust the diameter of the device in the deployed configuration dependent upon the size of the patient's aorta. In one embodiment, the power/control wire leading from the proximal end of the device enables the physician to dial in the cage diameter by extending or retracting the inner shaft portion within the outer shaft portion.

Optionally, in one embodiment, the device is designed in a manner such that when in the expanded configuration, said device takes on a slightly elliptical shape in which the proximal end is slightly smaller in diameter than the distal end. Such a design provides at least two benefits. First, the device sits in the aorta like a cone, resisting migration caused by the constant blood flow and forward pressure experienced by the device. Second, the device is easier to retrieve as it fits more easily back into the sheath.

Optionally, in one embodiment, magnetic coupling is used between the motor and the pump with the motor parts being hermetically sealed so that no fluid seepage can occur.

Optionally, in one embodiment, the device includes a self-charging battery in its proximal end. In this embodiment, the device includes an inverter. While the patient is at rest or in prone position, and the device is not in use, inertia and momentum caused by the blood flow generated by the heart continues to rotate the blades and is stored as energy for use when the device is in operation.

Optionally, in one embodiment a wireless Radio Frequency (RF) system is used for wireless electromagnetic powering of the device.

Optionally, in one embodiment, the device includes an accelerometer to detect increased movement by the patient, signifying increased physical activity. Based on the heightened physical activity, the device increases blood flow to meet demands. Conversely, if the accelerometer detects decreased physical activity, the device will decrease blood flow. In another embodiment, the device includes a flow meter. The flow meter will detect increased blood flow from the heart during heightened physical activity and the device will in turn increase speed and therefore blood flow. In one embodiment, the flow meter sends data to the patient via the cable attached to the proximal end of the device. The patient can then increase or decrease blood flow provided by the device based upon values obtained from the flow meter.

Optionally, in one embodiment, the distal end cap includes a mechanism that assists in the transformation of the device from the collapsed configuration into the deployed configuration. The distal cap is hollow and contains a biocompatible fluid that is used to provide hydraulics to change the device between collapsed and expanded shapes.

The device of the present specification increases blood flow to the body parts located downstream of said device, thereby decreasing strain upon the diseased heart. As demand on the heart is lessened, the heart muscle is able to rest and, over time, partially repair itself. In one embodiment, the helical screw pump of the device spins at a variable rate that is fully controlled in a closed loop via a monitoring and controlling computer. In one embodiment, the helical screw pump of the device spins at a rate within a range of 100 to 10,000 rpms. The lower speed allows for greater energy efficiency and decreased red blood cell destruction caused by the pump. In one embodiment, at least an additional 2.5 L/min of blood flow is provided by the device of the present specification. In various embodiments, additional blood flow greater than the amount of 2.5 L/min, and greater than that provided by a normally functioning heart at rest (about 5 L/min) are provided by the device of the present specification. Without assistance, the compromised heart would not be able to sustain adequate blood flow to the body, resulting in continual worsening of heart failure, eventually leading to death of the patient.

The present specification is also directed toward an arterial closure device used to close the access point in the artery following implantation or removal of the pumping device. In one embodiment, the arterial closure device comprises a sheath having a lumen, a proximal end, and a distal end. Disposed within the distal end of the sheath is a pair of arterial closure discs connected by a center member. When in the sheath, the discs are compressed into a tubular configuration. A tamper tool having a proximal end and a distal end extends within the lumen of the sheath. The proximal end of the tamper tool includes a handle and the distal end abuts the proximal disc of the pair of arterial closure discs. A physician places the distal end of the sheath in the artery through the access site. The physician then pushes on the handle of the tamper tool which causes the distal disc to extend beyond the distal end of the sheath and into the artery. As the distal disc extends, it expands into an umbrella shape. The physician then pulls back on the device such that the distal disc abuts the inner wall of the artery. Pushing again on the handle extends the proximal disc beyond the distal end of the sheath. The proximal disc also expands into an umbrella shape and comes to rest on the outer wall of the artery, effectively closing the arterial access site.

The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

FIG. 1 is an oblique front view illustration of one embodiment of the cardiovascular flow assist device 100 in the expanded, deployed configuration. In the pictured embodiment, the device 100 includes two sets of helical pump blades 104. Each blade 104 includes a multitude of small fenestrations 105. These fenestrations 105 impart increased flexibility to each blade 104 so that the blades will be easier to compress without sacrificing efficiency of the pump. Each blade 104 is connected to a portion of the rotating pump shaft, which is not easily visualized in this figure but is further discussed with reference to FIGS. 5A-6B. A cable 108 extends from the proximal end of the device 100 and, in various embodiments, carries power supply and/or control wires from outside the body to the device 100. The device 100 includes eight cage support members 120 encircling the pump. In one embodiment, two support members 120 are manufactured together in one piece to assist in assembly of the device, as will be further discussed with reference to FIGS. 9A-9D. In one embodiment, the device 100 includes a cap 106 at its distal end. In one embodiment, the distal end cap 106 is cone shaped. In the pictured embodiment, the distal end cap 106 includes four sensors 132 positioned equidistant from one another proximate the distal tip of said end cap 106. Four additional sensors 134 are positioned proximate the distal end of every second cage support member 120, such that every support member 120 containing a sensor is adjacent to a support member 120 without a sensor. Each support member 120 containing a distal end sensor 134 also has an additional sensor 136 proximate its proximal end, resulting in a total of twelve sensors on the device 100. Although twelve sensors are depicted in the pictured embodiment, any number of sensors may be used to provide the health care professional information regarding the functionality of the device 100. Data gathered by the sensors is transferred to a processor outside the patient via cable 108.

Figure 2:
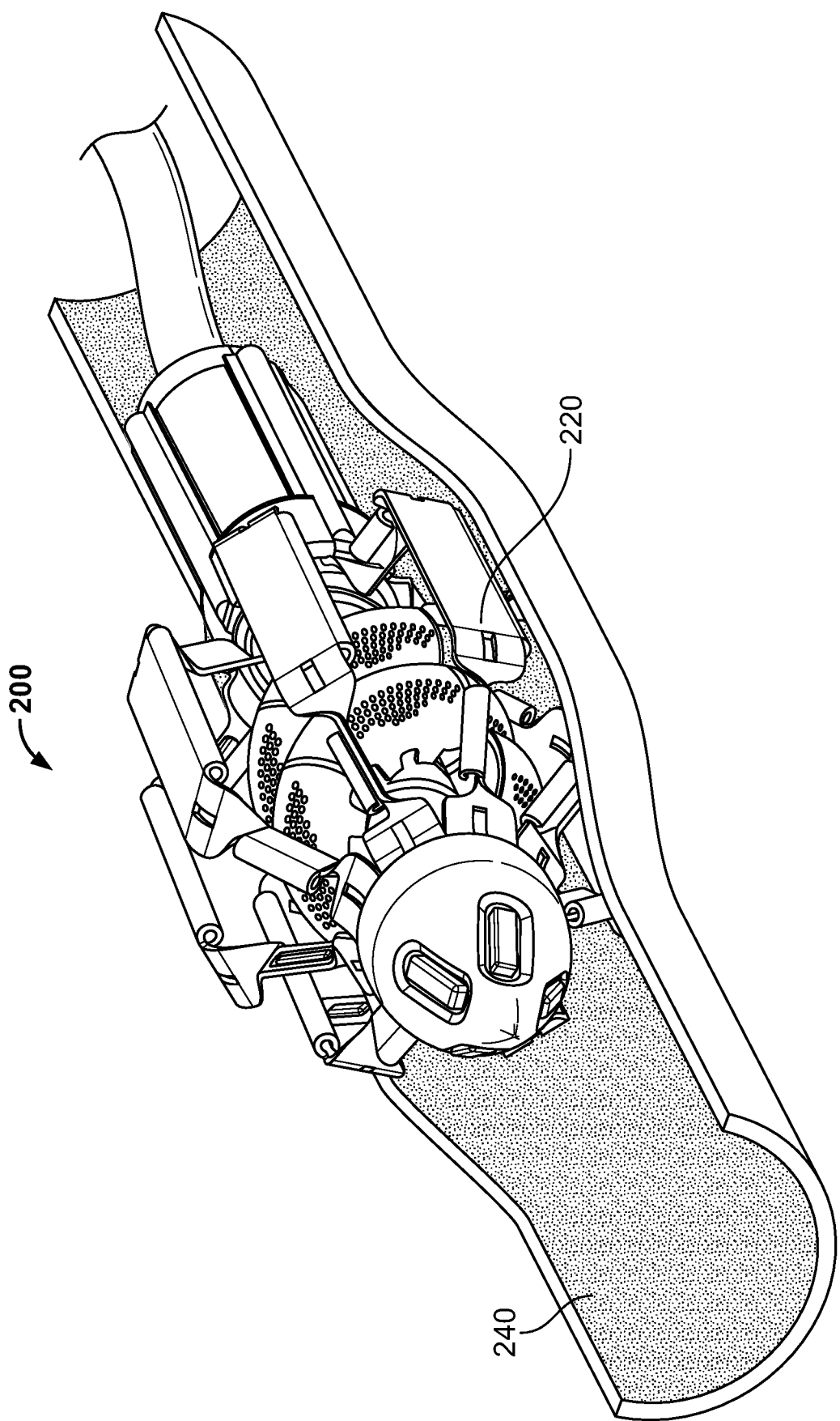
FIG. 2 is an oblique, cross-sectional illustration of an aorta depicting one embodiment of the cardiovascular flow assist device in the expanded, deployed configuration positioned therein.

FIG. 2 is an oblique, cross-sectional illustration of an aorta 240 depicting one embodiment of the cardiovascular flow assist device 200 in the expanded, deployed configuration positioned therein. When deployed, the diameter of the cage of the device 200 is slightly larger than the internal diameter of the aorta, such that the cage support members 220 contact the inner wall of the aorta. Each cage support member 220 becomes fixed in place against the aortic wall, securing the device 200 within the aorta 240. The pump is then free to rotate within the support cage, increasing blood flow downstream from the device 200.

Figure 3:
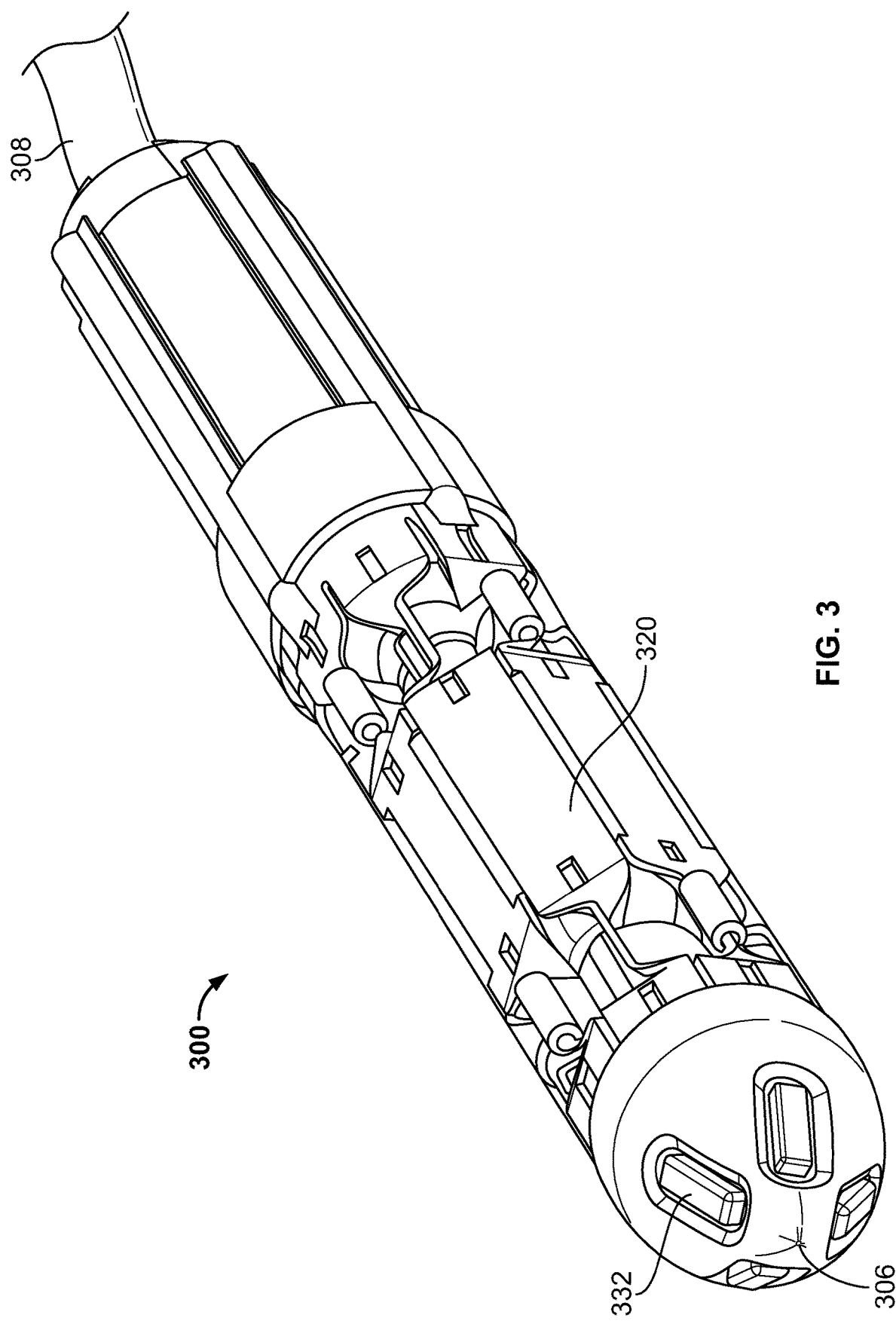
FIG. 3 is an oblique front view illustration of one embodiment of the cardiovascular flow assist device in the collapsed, deliverable configuration.

FIG. 3 is an oblique front view illustration of one embodiment of the cardiovascular flow assist device 300 in the collapsed, deliverable configuration. In the pictured embodiment, the device 300 includes a distal end cap 306 with sensors 332 and a power/control cable 308 emanating from its proximal end. The cage support members 320 are collapsed in toward the center of the device 300, forming an elongate, streamlined cylindrical shape. This collapsed configuration enables the physician to implant the device in a percutaneous fashion, avoiding a more invasive surgical procedure and resulting in less stress and discomfort to the patient.

Figure 4A:
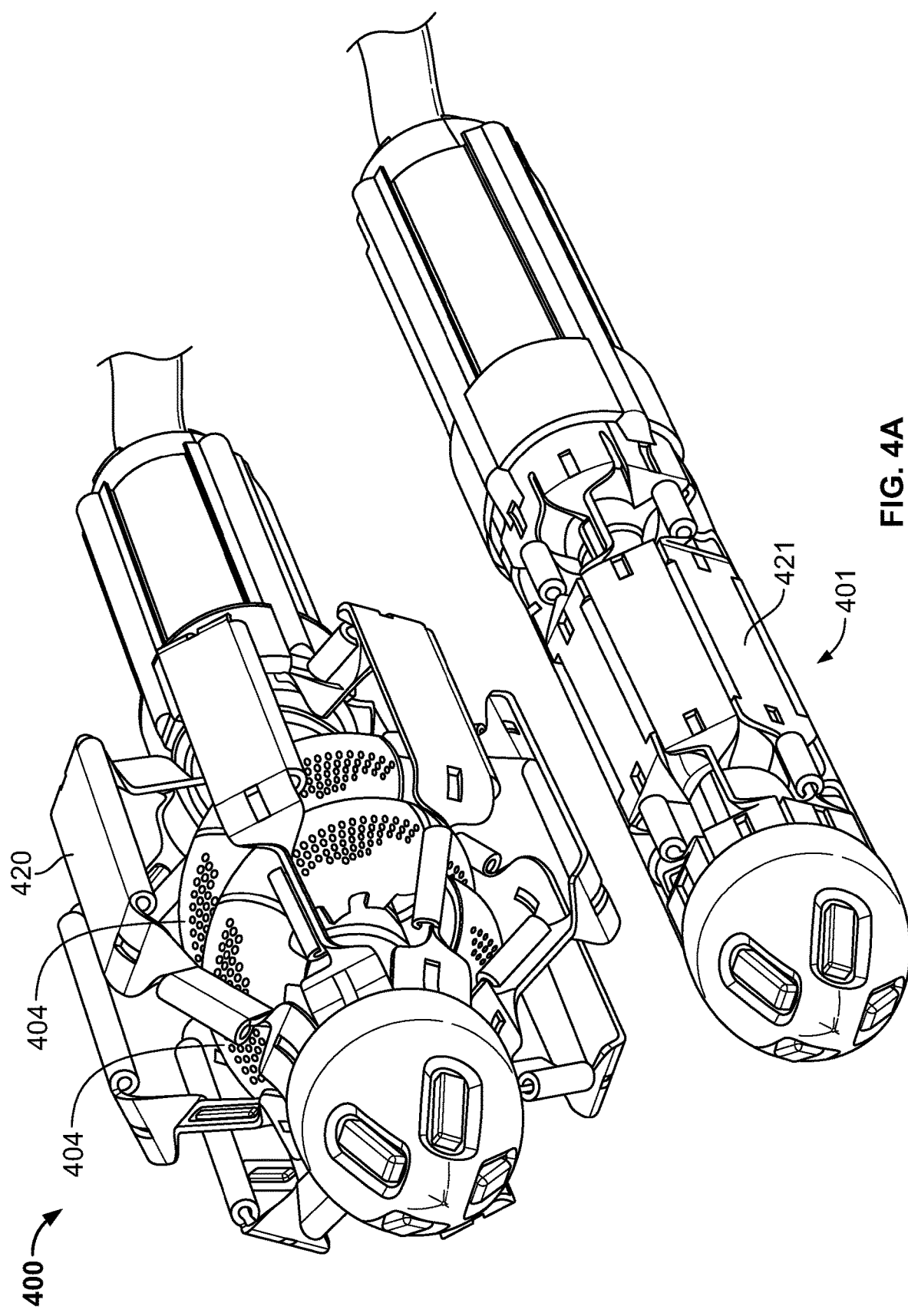
FIG. 4A is an oblique, front view illustration depicting one embodiment of a cardiovascular flow assist device in the expanded, deployed configuration side by side with another cardiovascular flow assist device in the collapsed, deliverable configuration.
Figure 4B:
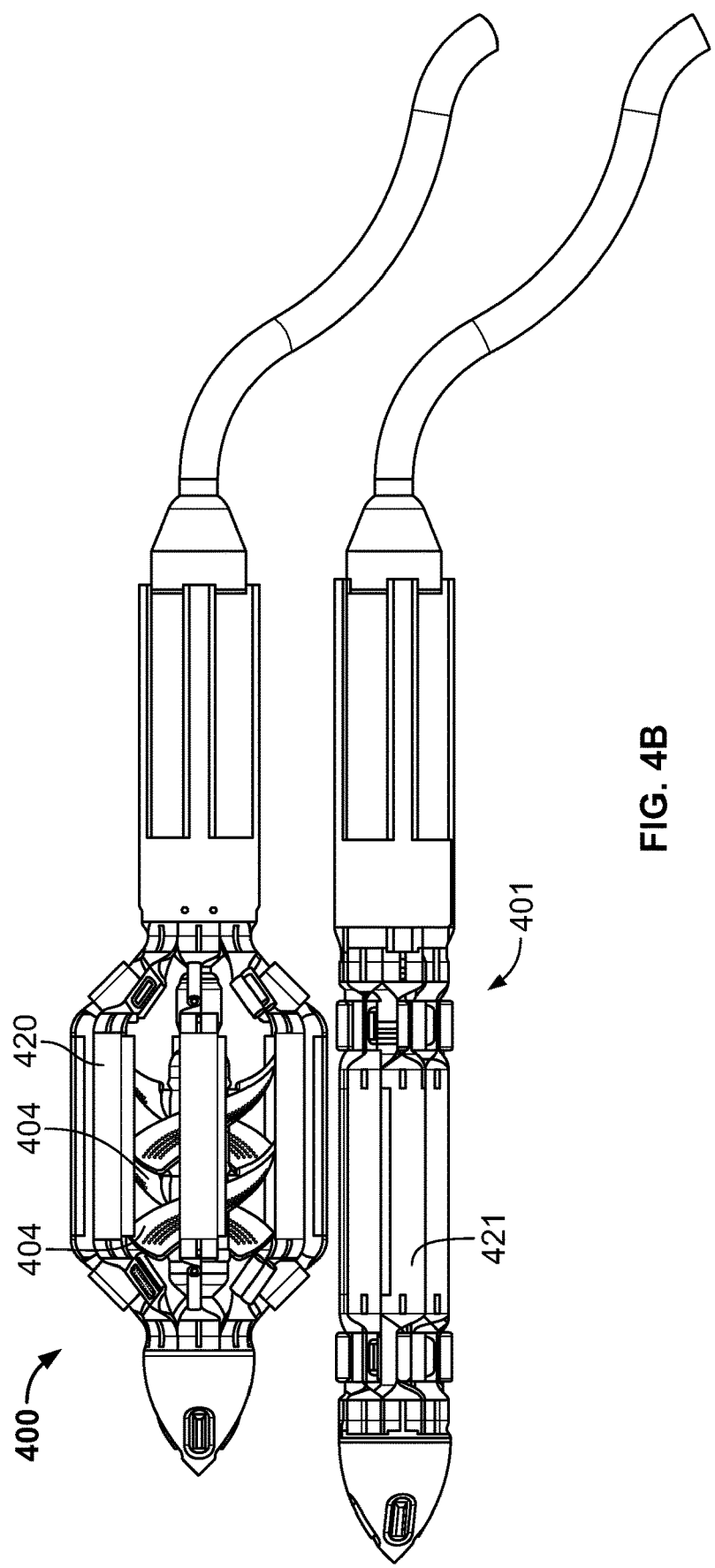
FIG. 4B is a side view illustration depicting the same embodiment of a cardiovascular flow assist device in the expanded, deployed configuration side by side with another cardiovascular flow assist device in the collapsed, deliverable configuration, of FIG. 4A.

FIGS. 4A and 4B are oblique front and side illustrations, respectively, depicting one embodiment of a cardiovascular flow assist device 400 in the expanded, deployed configuration side by side with another cardiovascular flow assist device 401 in the collapsed, deliverable configuration. The cage support members 420 of the deployed device 400 are seen in their fully expanded state, exposing the pump and helical pump blades 404. The cage support members 421 of the collapsed device 401 are seen in their fully compressed state, collapsed toward the center of the device and coming to rest in contact with one another.

As can be seen in FIGS. 4A and 4B, the diameter of the device 400 when in the expanded configuration, particularly the diameter of the cage, is larger than the diameter of the device 401 when in the collapsed configuration. There are different sized devices for different sized aortas. The impeller (rotary portion) is also sized corresponding to each different sized device. The surface area of the impeller itself determines its efficacy—the larger the surface area of the impeller, the more efficient it is at pumping blood. The cage is sized accordingly so that it can be placed over the impeller.

Some embodiments of the impeller of the present specification incorporate a blade skeleton comprising a plurality of morphed microcells each having a substantially hexagonal shape and comprised of a shape memory alloy such as Nitinol. A thin layer of silicone is coated over the hexagonal microcells and in the space or area within each hexagon to complete the blade structure. As the blade of the impeller is wrapped around an inner shaft of the impeller in the collapsed configuration, the microcells are reshaped by tessellations, allowing for tight compression of the blade about the shaft. In embodiments, each side of each hexagon comprises an 'S' or dollar sign shape to impart increased flexibility to the blade such that it is more easily deformed. Since the width and thickness of each skeleton junction are equal, the deformation of the blade skeleton in a collapsed configuration is distributed by wrapping around said impeller shaft. The hexagonal patterns are preferred due to their efficiency in changing the shape of the blade as the device moves from a collapsed configuration to an expanded configuration, although other polygonal patterns are possible, such as trigonal, tetragonal, pentagonal, heptagonal, octagonal, enneagonal and other shapes. In a hexagonal grid, each skeletal component is the smallest it can possibly be, while the area of the blade skeleton is the largest it can possibly be, and the area is filled with the fewest number of hexagons in the impeller structure. The hexagonal shape provides for the greatest flexibility and deformability while requiring the least amount of material and therefore the least weight. The impeller design, in accordance with the present embodiments, assures the lowest mass of the blade which is directly related to the motor torque requirement.

An optimal torque can be obtained for the device 400 by determining a ratio of the diameter of the device 400 and the length of the device 400. Because the diameter is fixed for each device size, the variable factor for achieving optimal torque is device length. In embodiments, a longer motor length corresponds to a stronger motor. In embodiments, device 401 when in the collapsed configuration is 30-35% the size of device 400 when in the expanded configuration.

As can also be seen in FIGS. 4A and 4B, the length of the device 400 when in the expanded configuration is shorter than the length of the device 401 when in the collapsed configuration. In one embodiment, the length of the device 400 when in the expanded configuration is in the range of 20 mm to 90 mm. In one embodiment, the length of the device 401 when in the collapsed configuration is in the range of 30 mm to 100 mm.

An inner shaft portion and various outer shaft portions that are used to mount the blades 404 are proportioned to be as small in diameter as possible. In an embodiment, the inner shaft portion and various outer shaft portions together span a diameter of 2 mm. In an embodiment, the blades 404 are wrapped on the outer shaft portions in a closed form. In various embodiments, the diameter of the device 400 in the expanded configuration is in the range of 15 mm to 30 mm. In various embodiments, the diameter of the device 400 in an expanded configuration is in the range of 18 mm to 24 mm. In some embodiments, the diameter of the device 401 in the collapsed configuration is in the range of 3 mm to 8 mm. In one embodiment, the diameter of the device 400 in the expanded configuration is 18 mm, while the diameter of the device 401 in the collapsed configuration is 6 mm.

In one embodiment, a motor having a diameter of 5 mm is positioned within a housing having a diameter of 6 mm. In this embodiment, an impeller opens to a diameter of 15 mm and a cage opens to a diameter of 18 mm. In an expanded configuration, the cage has a diameter having a range of 16 mm, 17 mm, and up to 18 mm. In another embodiment, a motor having a diameter of 6 mm is positioned within a housing having a diameter of 7 mm. In this embodiment, an impeller opens to a diameter of 18 mm and a cage opens to a diameter of 21 mm. In the expanded configuration, the cage has a diameter having a range of 19 mm, 20 mm, and up to 21 mm. In yet another embodiment, a motor having a diameter of 7 mm is positioned within a housing having a diameter of 8 mm. In this embodiment, an impeller opens to a diameter of 22 mm and a cage opens to a diameter of 25 mm. In this embodiment, in an expanded configuration, the cage has a diameter having a range of 22 mm to 23.5 mm and up to 25 mm. In still another embodiment, a motor having a diameter 7 mm is positioned within a housing having a diameter 8 mm. In this embodiment, an impeller opens to a diameter of 24 mm and a cage opens to a diameter of 28 mm. In the expanded configuration, the cage has a diameter having a range of 26 mm, 27 mm, and up to 28 mm. In some embodiments, and discussed subsequently with reference to FIGS. 20A and 20B, a second anchoring cage is added outside the device 400/401. The total diameter of the device 400/401 with the second anchoring cage may increase by approximately 4 mm. Therefore, in some embodiments, the total outer diameter of the device in the expanded configuration is 32 mm.

Figure 5A:
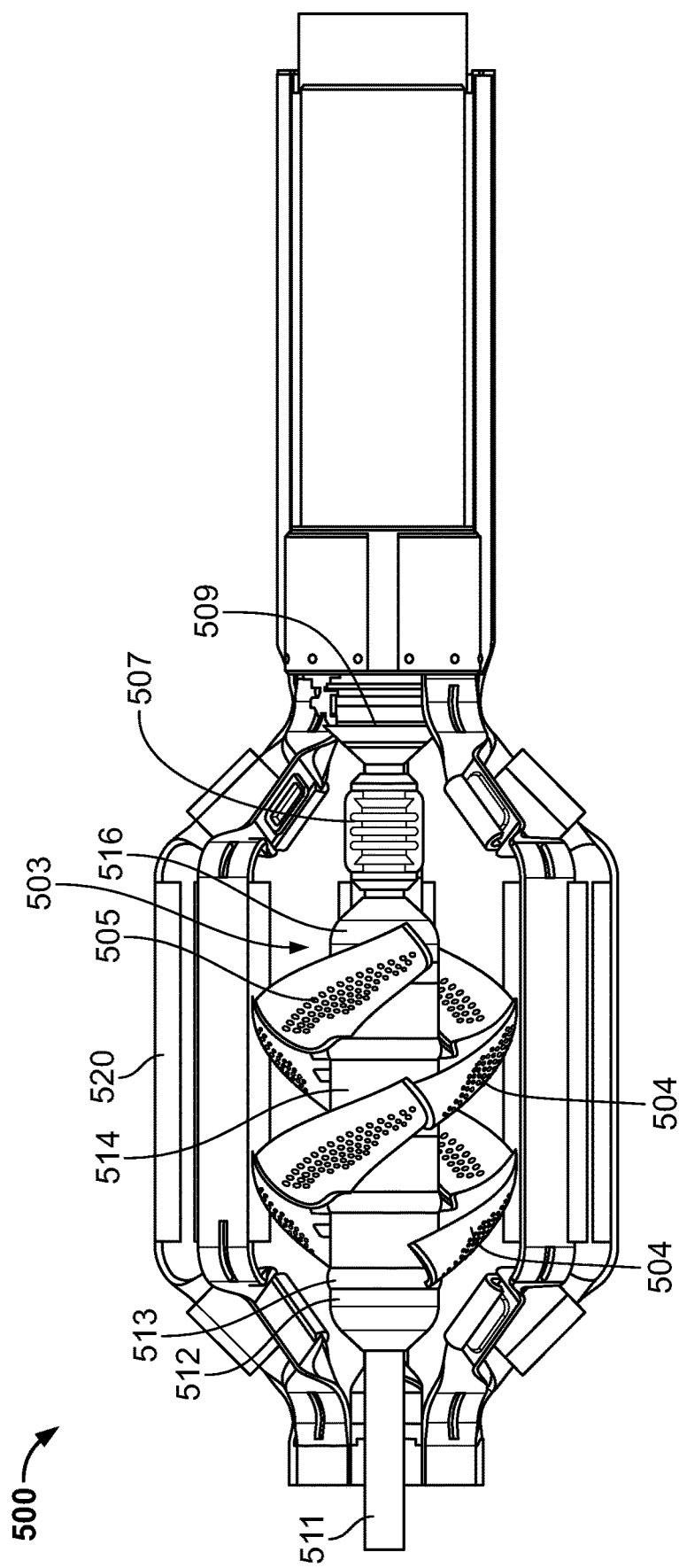
FIG. 5A is a side view illustration of one embodiment of the cardiovascular flow assist device in the expanded, deployed configuration, depicting two cage support members removed from either side of the helical screw pump.

FIG. 5A is a side view illustration of one embodiment of the cardiovascular flow assist device 500 in the expanded, deployed configuration, depicting two cage support members 520 removed from either side of the helical screw pump 503. The end cap (not shown) has also been removed from the device 500 pictured in FIG. 5A. These components have been removed to provide enhanced visualization of the helical screw pump 503 of the device 500. In one embodiment, the helical screw pump 503 comprises an elongate, cylindrical inner shaft portion 511, a distal outer shaft portion segment 512, four outer shaft portion blade attachment segments 514, five outer shaft portion spacer segments 513, and a proximal outer shaft portion segment 516. The pump 503 is connected at its proximal end, via a coupling 507, to a motor 509. In one embodiment, motor 509, coupling 507 and inner shaft 511 are manufactured as a single component. In one embodiment, the coupling 507 is a low friction flexible coupling which transfers rotation from the motor 509 to the shaft. The coupling 507 acts to keep the motor 509 and shaft in alignment and prevents binding and stoppage of the motor 509. In the pictured embodiment, the pump 503 includes two sets of helical blades 504. Each outer blade attachment segment 514 of the pump 503 shaft includes two attached blades 504 positioned 180 degrees apart on either side of said segment 514. Each of the two blade sets comprises four separate blades 504. In various embodiments, the pitch of each blade in the deployed configuration is within the range of 20 to 70 degrees. In one embodiment, the pitch of each blade in the deployed configuration is 45 degrees. The blades 504 in each set join to form a continuous helical screw spiraling around either side of the pump 503. Having two sets of blades 504 improves performance of the pump by increasing pumping efficiency and by balancing the pump 503. In addition, having the pump blades formed in segments eases collapsibility and allows for intended deformation to create the smallest outside profile for minimally invasive intravascular insertion. In one embodiment, each blade 504 includes a multitude of fenestrations 505 to increase flexibility of the blades for compression and expansion. In one embodiment, the blades 504 are coated in silicon to prevent blood flow through the fenestrations 505.

In one embodiment, the inner shaft portion 511 of the pump extends through to the coupling 507 and is slidably movable within the pump's outer shaft portion segments 512, 514, 513, 516. This allows the device to lengthen and shorten during compression and expansion respectively. In one embodiment, the distal end of the inner shaft portion 511 of the pump 503 and the distal ends of the cage support members 520 attach to the distal end cap (not shown). To lend linear stability to the device 500, in one embodiment, the inner shaft portion 511, distal outer shaft portion segment 512, outer shaft portion blade attachment segments 514, and proximal outer shaft portion segment 516 are composed of stainless steel. In one embodiment, the outer shaft portion spacer segments 513 are composed of silicon to absorb pressure during compression and expansion of the device 500. As mentioned earlier, the blades 504 are composed of a shape memory metal to allow for compression and expansion of said blades 504. In one embodiment, the shape memory metal is Nitinol. In one embodiment, the device 500 includes a Teflon motor seal.

Figure 5B:
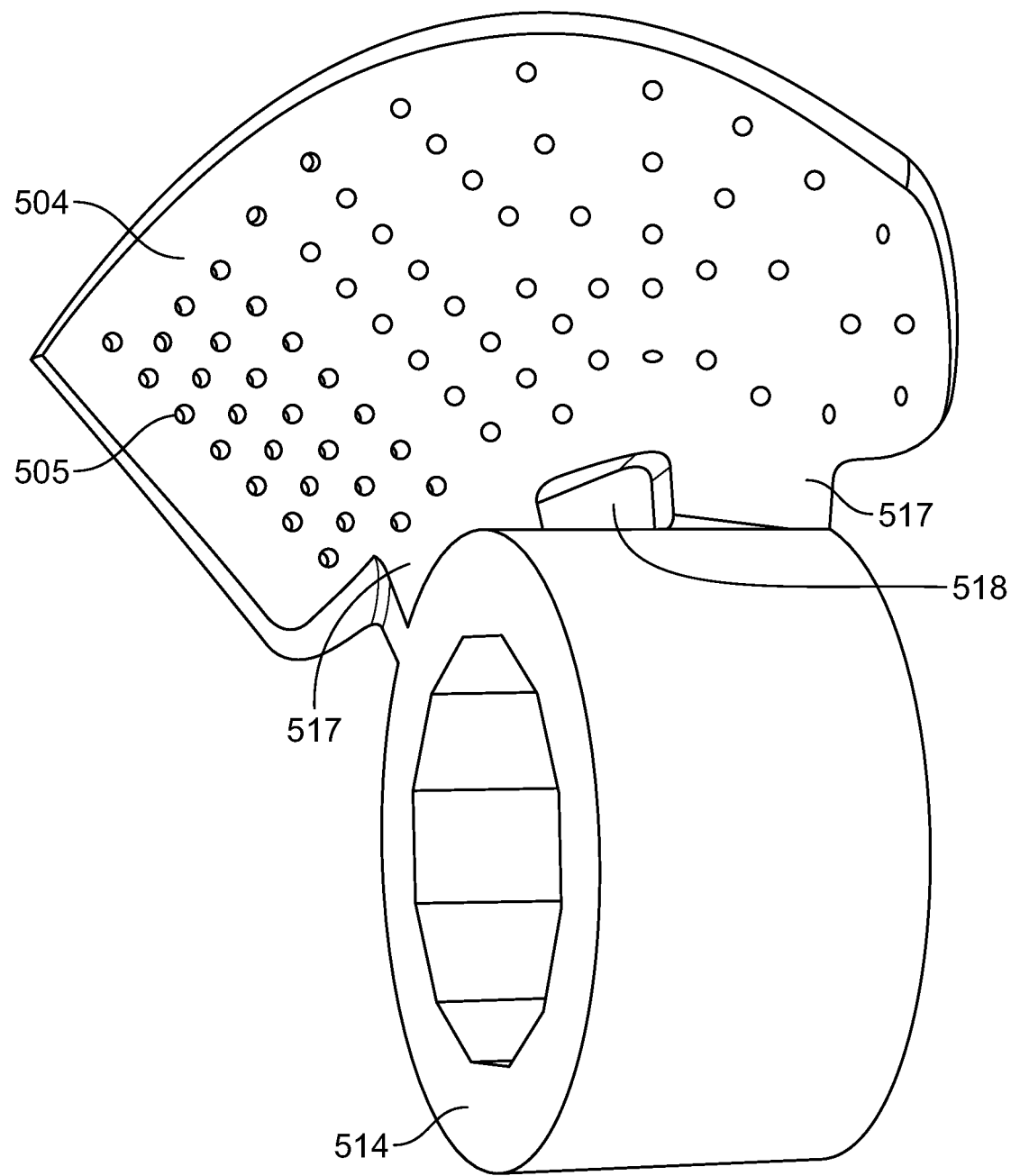
FIG. 5B is an oblique, side view illustration of one embodiment of an outer shaft portion blade attachment segment, with one attached blade, of the cardiovascular flow assist device.

FIG. 5B is an oblique, side view illustration of one embodiment of an outer shaft portion blade attachment segment 514, with one attached blade 504, of the cardiovascular flow assist device. In one embodiment, each blade 504 is laser welded to each segment 514 at two points 517 along the outer circumference of the segment 514, with a gap 518 in between the two weld points 517. The gap 518, along with the fenestrations 505 in the blade 504, lends greater flexibility to the blade 504 to ease blade compression and expansion.

Figure 6A:
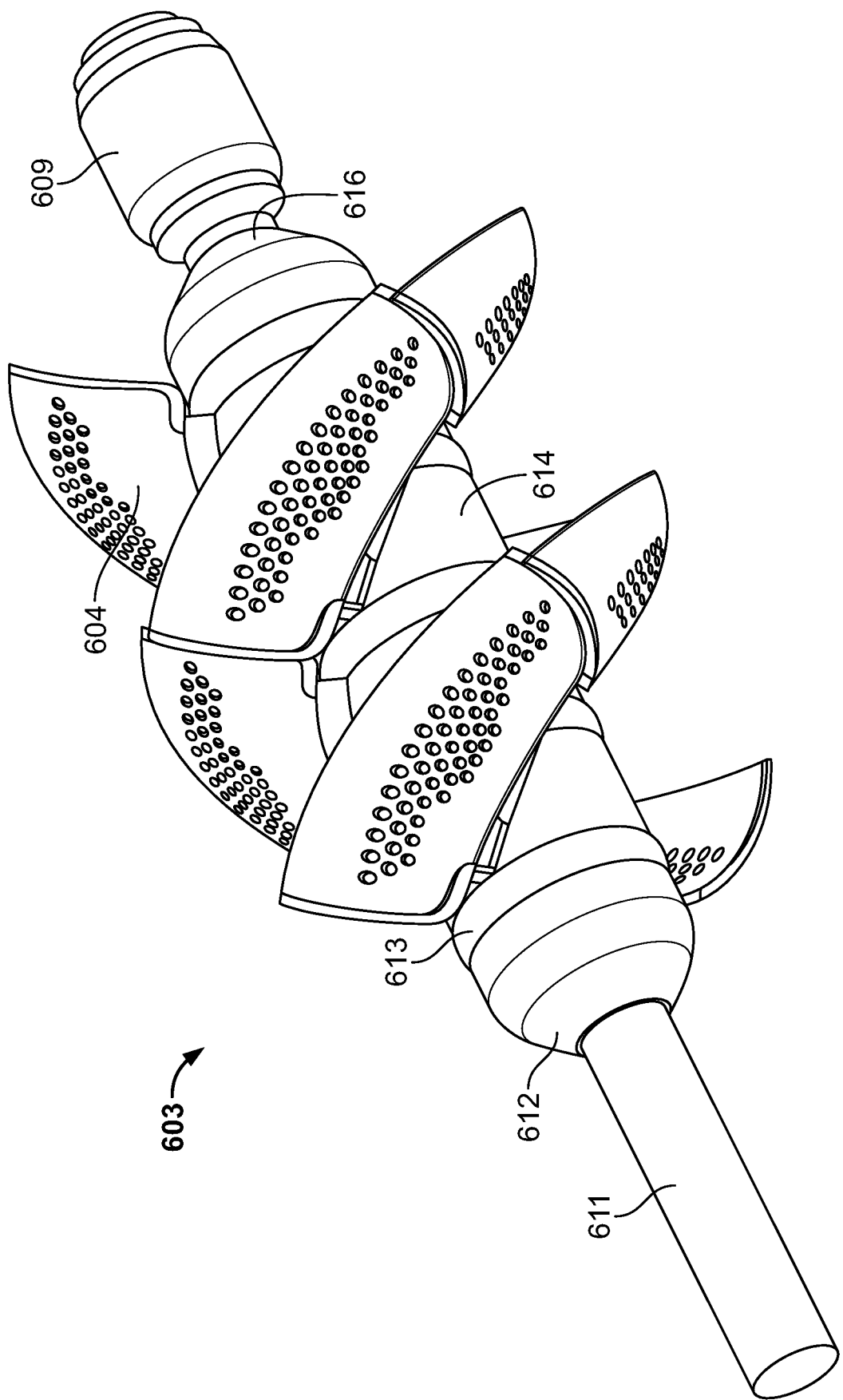
FIG. 6A is an oblique, front view illustration of one embodiment of the helical screw pump of the cardiovascular flow assist device, depicting two sets of helical blades in the expanded configuration.
Figure 6B:
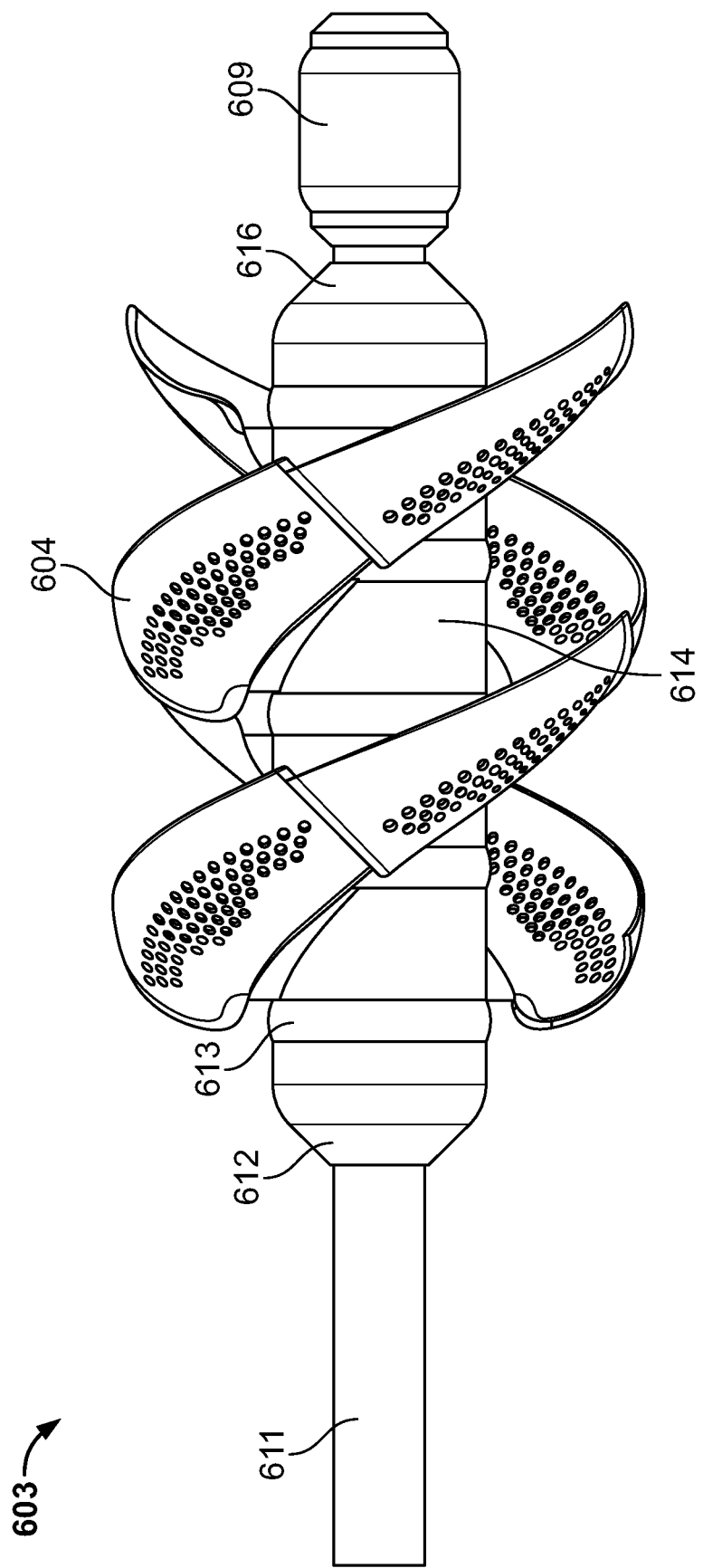
FIG. 6B is a side view illustration of the same embodiment of the helical screw pump of the cardiovascular flow assist device, depicting two sets of helical blades in the expanded configuration, of FIG. 6A.

FIG. 6A is an oblique, front view illustration and FIG. 6B is a side view illustration of one embodiment of the helical screw pump 603 of the cardiovascular flow assist device, depicting two sets of helical blades 604 in the expanded configuration. The distal end cap and cage have been completely removed to enhance pump 603 visualization. In the embodiment depicted in FIGS. 6A and 6B, the pump 603 does not include a coupling and the entirety of the motor 609 can be seen. Also visible are the inner shaft portion 611, distal outer shaft portion segment 612, outer shaft portion blade attachment segments 614, outer shaft portion spacer segments 613, and proximal outer shaft portion segment 616.

Figure 7A:
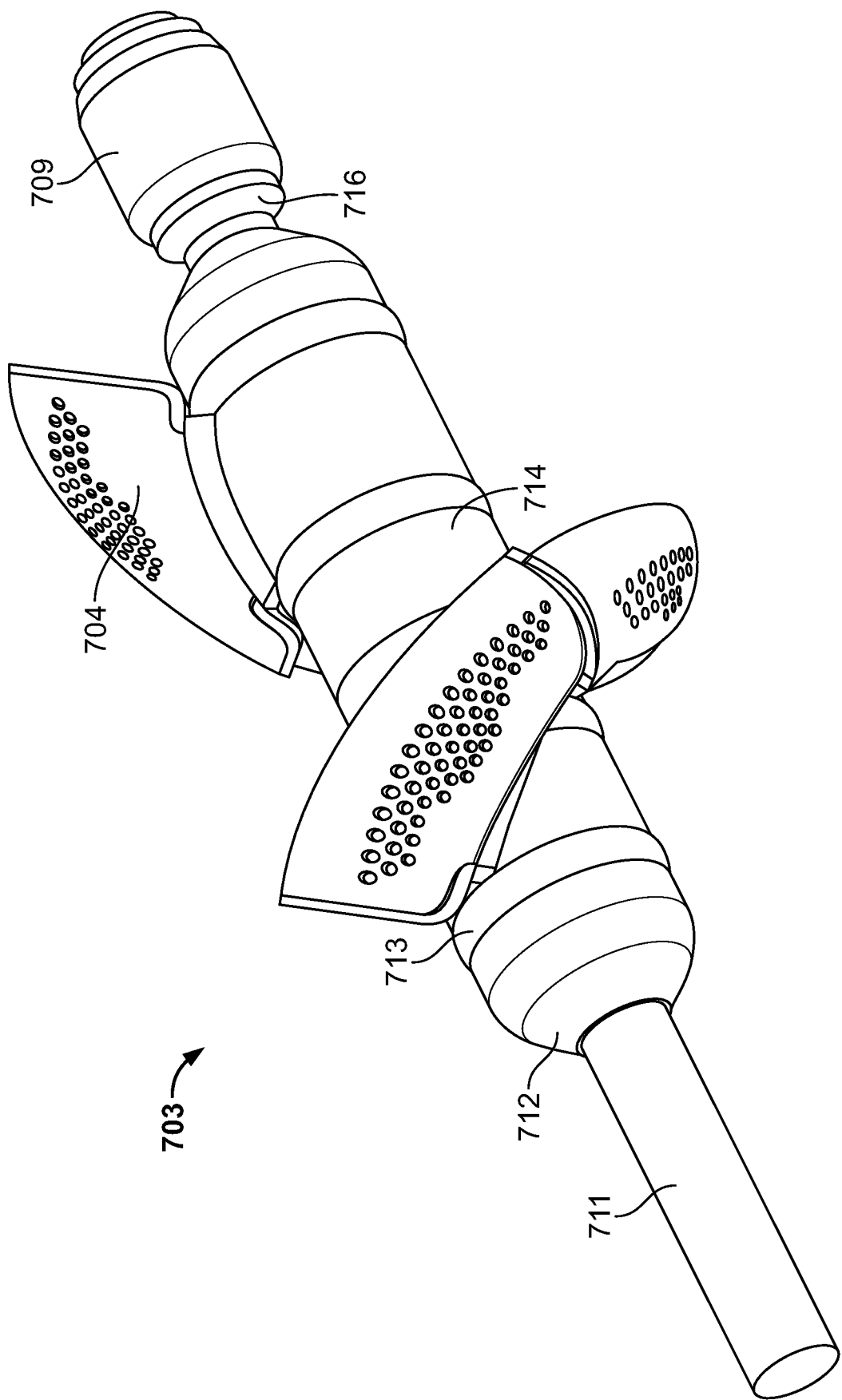
FIG. 7A is an oblique, front view illustration of one embodiment of the helical screw pump of the cardiovascular flow assist device in the expanded configuration, depicting one set of helical blades.
Figure 7B:
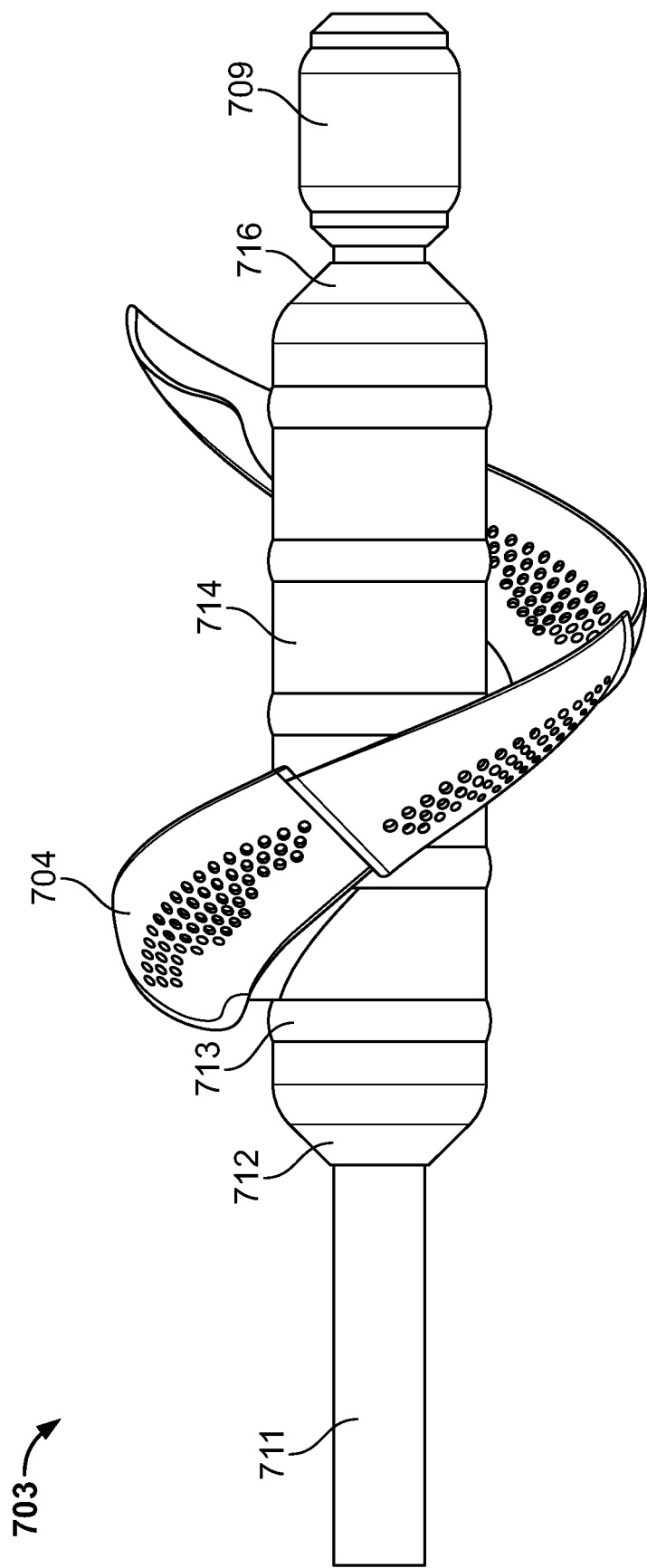
FIG. 7B is a side view illustration of the same embodiment of the helical screw pump of the cardiovascular flow assist device, depicting one set of helical blades in the expanded configuration, of FIG. 7A.
Figure 7C:
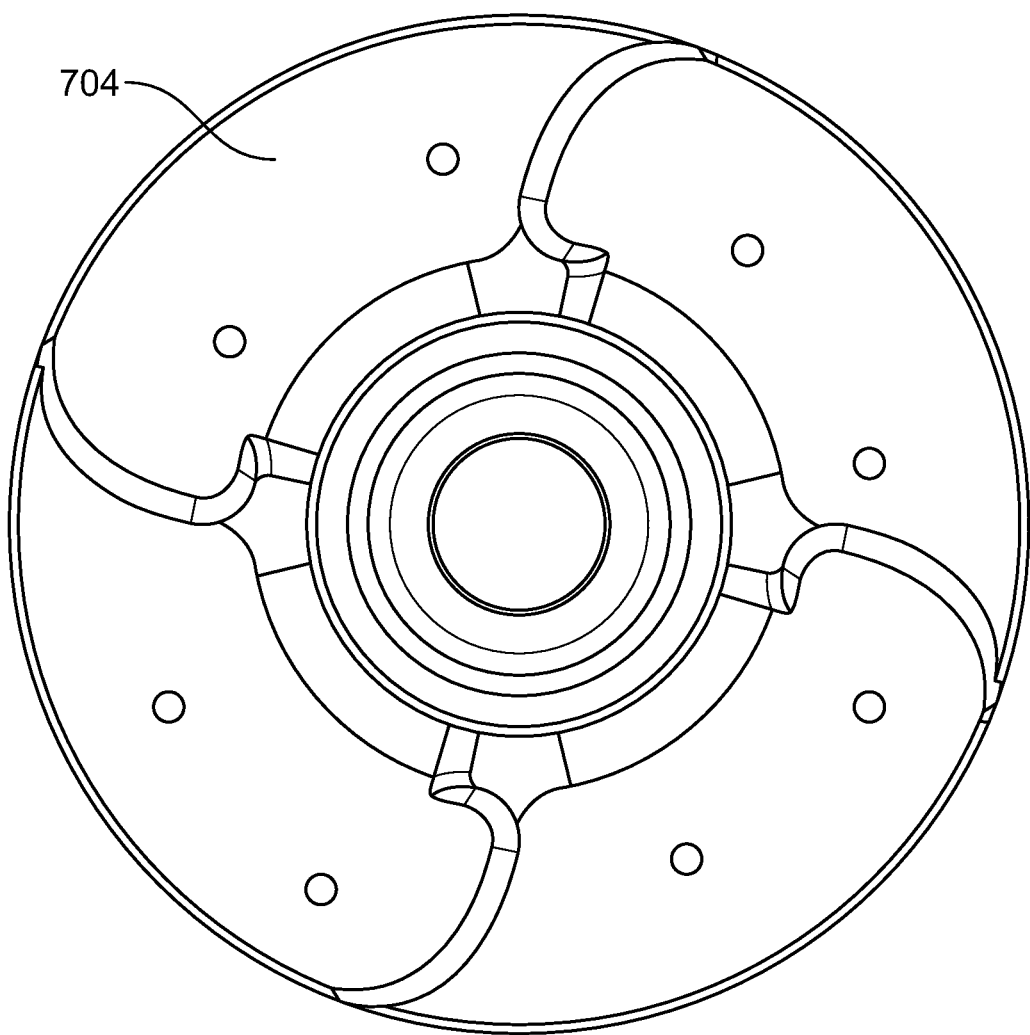
FIG. 7C is a front-on view illustration of the same embodiment of the helical screw pump of the cardiovascular flow assist device, depicting one set of helical blades in the expanded configuration, of FIG. 7A.

FIGS. 7A, B, and C are oblique front, side, and front-on view illustrations respectively, of one embodiment of the helical screw pump 703 of the cardiovascular flow assist device, depicting one set of helical blades 704 in the expanded configuration. The distal end cap and cage have been completely removed to enhance pump 703 visualization. Referring simultaneously to FIGS. 7A and 7B, the pictured embodiment of the pump 703 does not include a coupling and the entirety of the motor 709 can be seen. Also visible are the inner shaft portion 711, distal outer shaft portion segment 712, outer shaft portion blade attachment segments 714, outer shaft portion spacer segments 713, and proximal outer shaft portion segment 716. FIG. 7C illustrates how each blade 704 meets the other to form a virtually seamless helical screw.

Figure 8A:
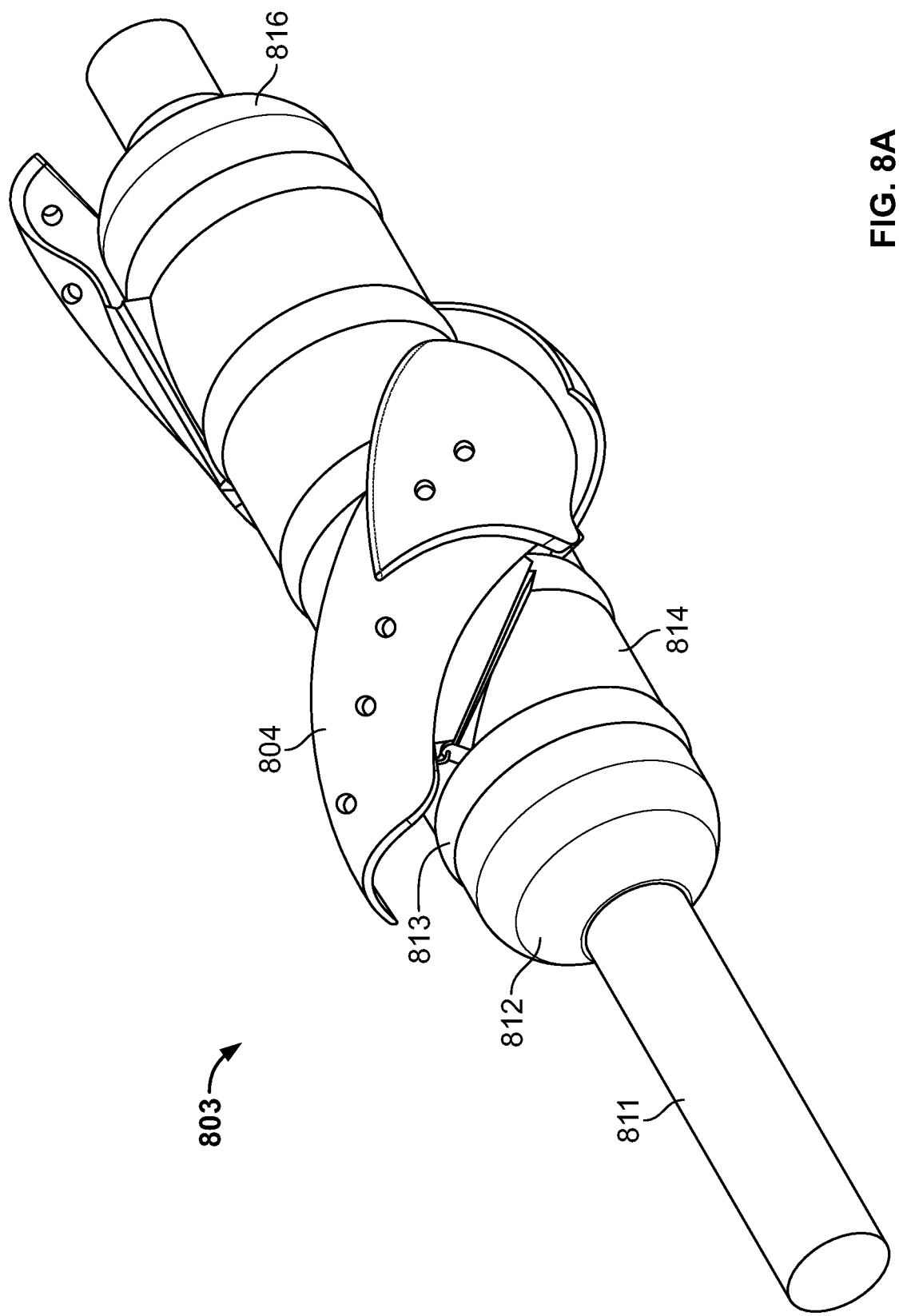
FIG. 8A is an oblique, front view illustration of one embodiment of the helical screw pump of the cardiovascular flow assist device, depicting one set of helical blades in the collapsed configuration.
Figure 8B:
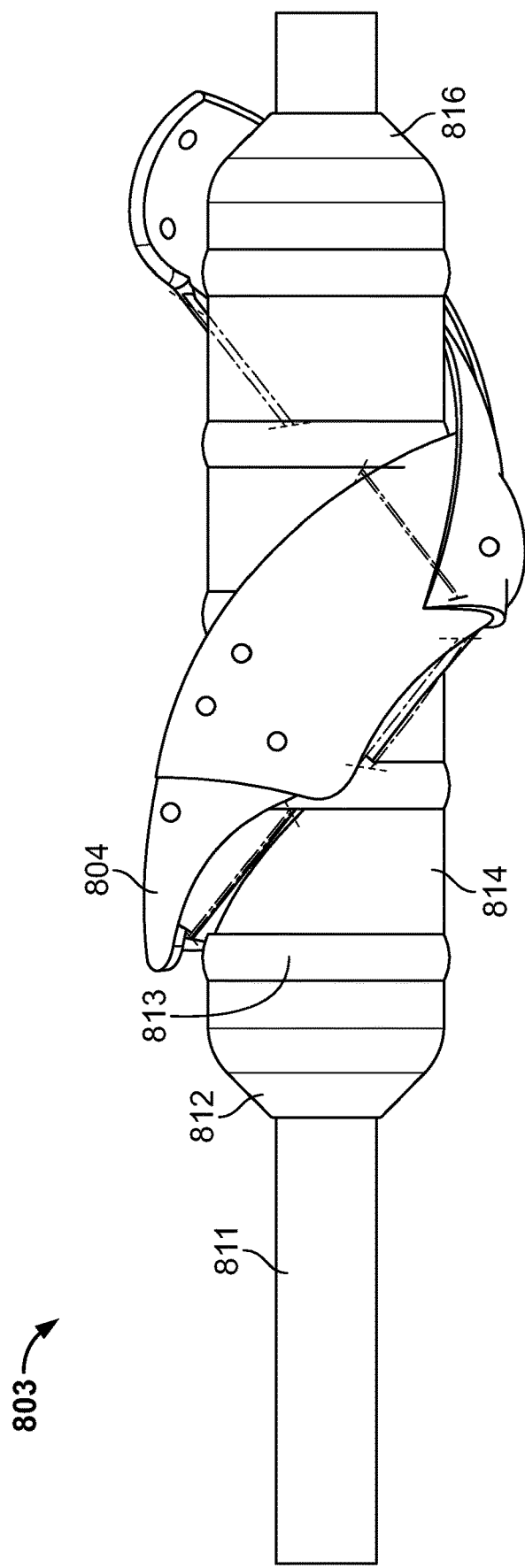
FIG. 8B is a side view illustration of the same embodiment of the helical screw pump of the cardiovascular flow assist device, depicting one set of helical blades in the collapsed configuration, of FIG. 8A.
Figure 8C:
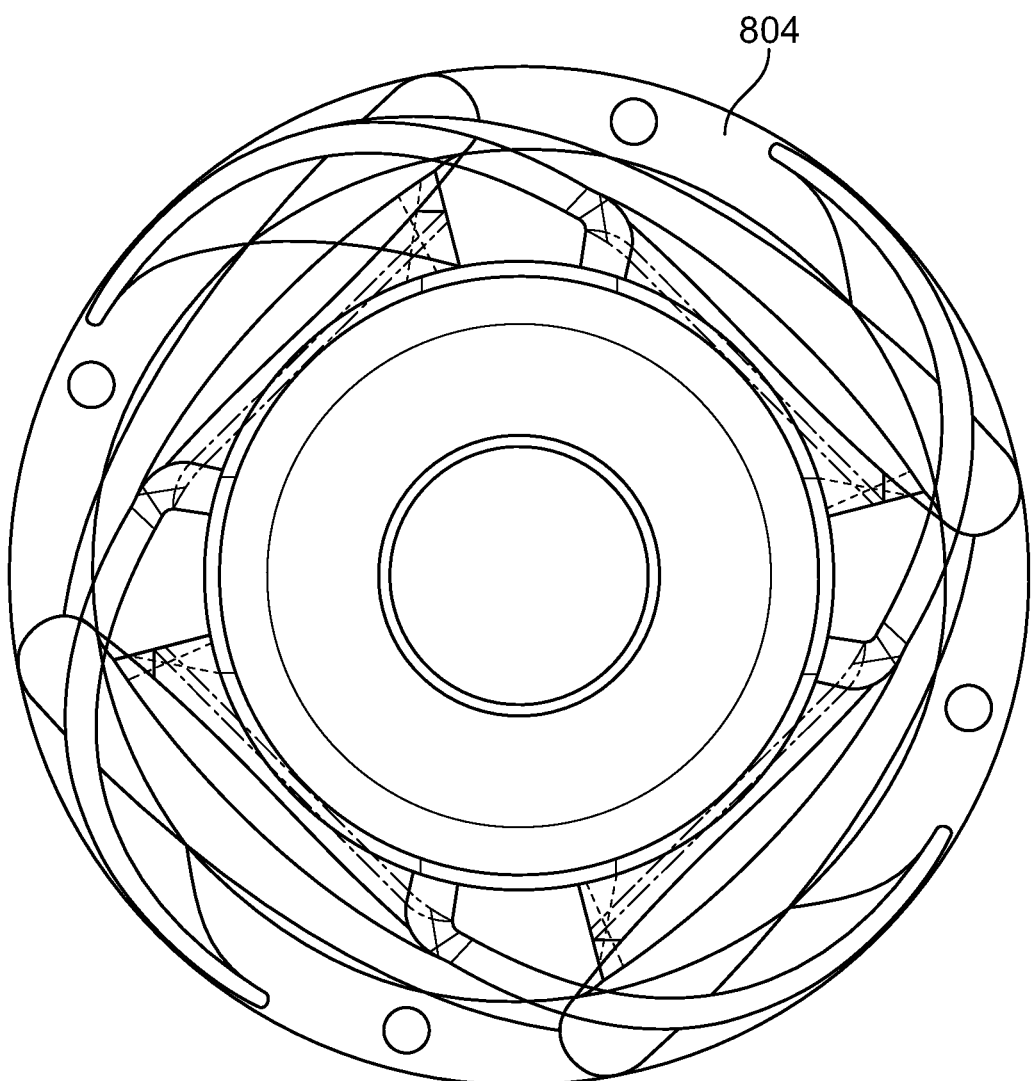
FIG. 8C is a front-on view illustration of the same embodiment of the helical screw pump of the cardiovascular flow assist device, depicting one set of helical blades in the collapsed configuration, of FIG. 8A.

FIGS. 8A, 8B, and 8C are oblique front, side, and front-on view illustrations respectively, of one embodiment of the helical screw pump of the cardiovascular flow assist device, depicting one set of helical blades in the collapsed configuration. The distal end cap, cage, coupling, and motor have been completely removed to enhance pump 803 visualization. Referring simultaneously to FIGS. 8A and 8B, the inner shaft portion 811, distal outer shaft portion segment 812, outer shaft portion blade attachment segments 814, outer shaft portion spacer segments 813, and proximal outer shaft portion segment 816 are all visible. FIG. 8C illustrates how each blade 804 compresses in toward the body of the pump shaft while in the collapsed configuration.

Figure 9A:
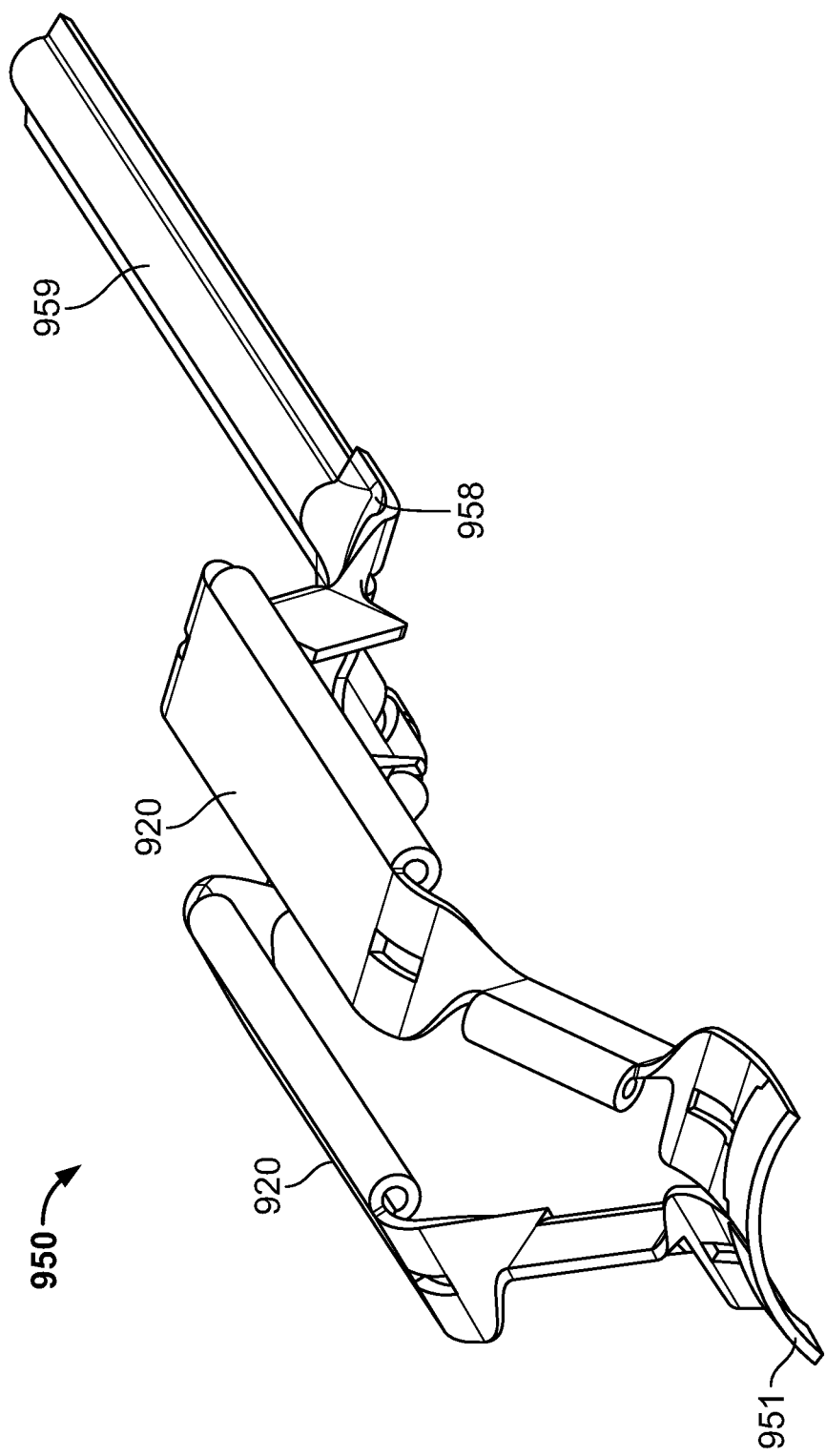
FIG. 9A is an oblique, front view illustration of one embodiment of two cage support members formed together into a singular cage arm in the expanded configuration.

FIG. 9A is an oblique, front view illustration and FIG. 9B is a side view illustration of one embodiment of two cage support members 920 formed together into a singular cage arm 950 in the expanded configuration. Referring simultaneously to FIGS. 9A and 9B, while in the expanded configuration, the two cage support members 920 of each cage arm 950 are expanded outward from the pump (not shown) and from one another. At the distal end of each cage arm 950, the two support members come together in the form of a distal quarter-circle 951. At the proximal end of each cage arm 950, the two support members come together in the form of a proximal quarter circle 958 with attached elongate linear member 959. In one embodiment, four cage arms 950 are circularly arranged around the helical screw pump (not shown) of the device to form the basket-like cage support structure. The four distal quarter-circles 951 are attached to the distal end cap (not shown) and inner shaft portion (not shown) of the pump at the distal end of the device. The four proximal quarter-circles 958, with attached elongate linear members 959, are attached to a housing (not shown) supporting the motor (not shown) at the proximal end of the device.

FIG. 9C is a top-down view illustration of the same embodiment of two cage support members 920 formed together into a singular cage arm 950 in the expanded configuration of FIG. 9A. In one embodiment, the central, thin rectangular shaped portion 921 of each cage support member 920 is composed of stainless steel. In this embodiment, the rigidity of this portion 921 lends stability to the device. In another embodiment, the central, thin rectangular shaped portion 921 of each cage support member 920 is composed of a shape memory metal. In one embodiment, the shape memory metal is Nitinol. In this embodiment, the flexibility of this portion 921 allows the cage to fit more snugly within the aorta. This portion 921 comes to rest against the inner wall of the aorta when the device is deployed. Distal and proximal to each central portion 921 are two hinge portions 922 and 924 respectively. Each hinge portion 922, 924 is composed of a shape memory metal and allows for compression and expansion of each cage support member 920. In one embodiment, the shape memory metal is Nitinol. In one embodiment, the distal end 923 and proximal end 925 of each support member 920 are composed of stainless steel. This again lends overall stability to the device and allows for attachment of the support members 920 to the other components of the device. In one embodiment, each elongate linear member 959 is composed of stainless steel.

In one embodiment, each hinge portion 922, 924 includes at least one slit 926 to enhance flexibility and for the passage of a wire leading from a sensor positioned distally on the device. Additionally, in one embodiment, each hinge portion 922, 924 includes an elongate tubular member 927 along its external edge for the guiding of sensor and/or camera wires. In one embodiment, each central rectangular portion 921 includes an elongate tubular member along one side for the guiding of sensor and/or camera wires.

Figure 9D:
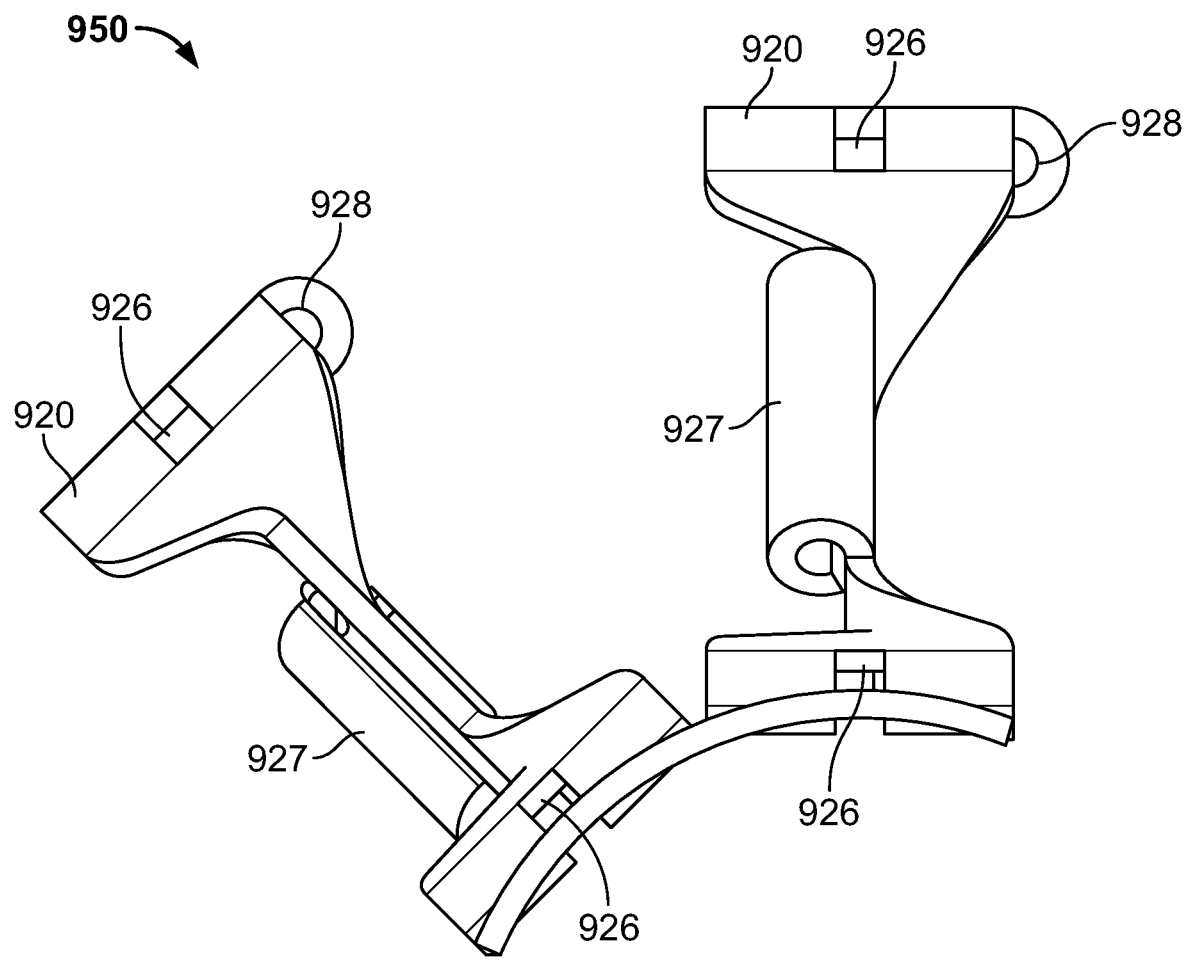
FIG. 9D is a front-on view illustration of the same embodiment of two cage support members formed together into a singular cage arm in the expanded configuration of FIG. 9A.

FIG. 9D is a front-on view illustration of the same embodiment of two cage support members 920 formed together into a singular cage arm 950 in the expanded configuration of FIG. 9A. Visible in FIG. 9D are the slits 926 and elongate tubular members 927, 928 for the passage of sensor and/or camera wires.

Figure 10A:
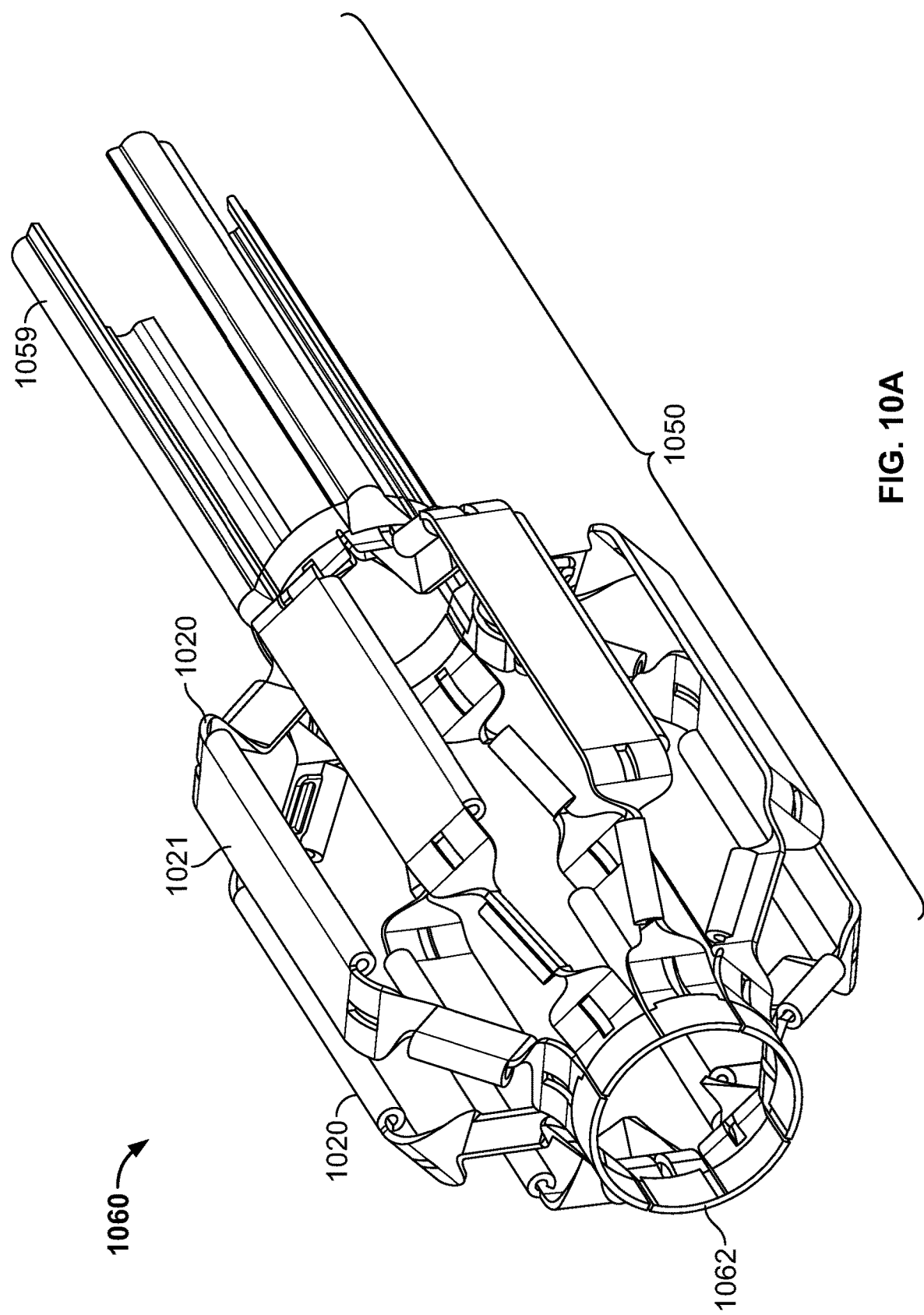
FIG. 10A is an oblique, front view illustration of one embodiment of four cage arms combined together to form a complete basket-like cage in the expanded configuration.
Figure 10B:
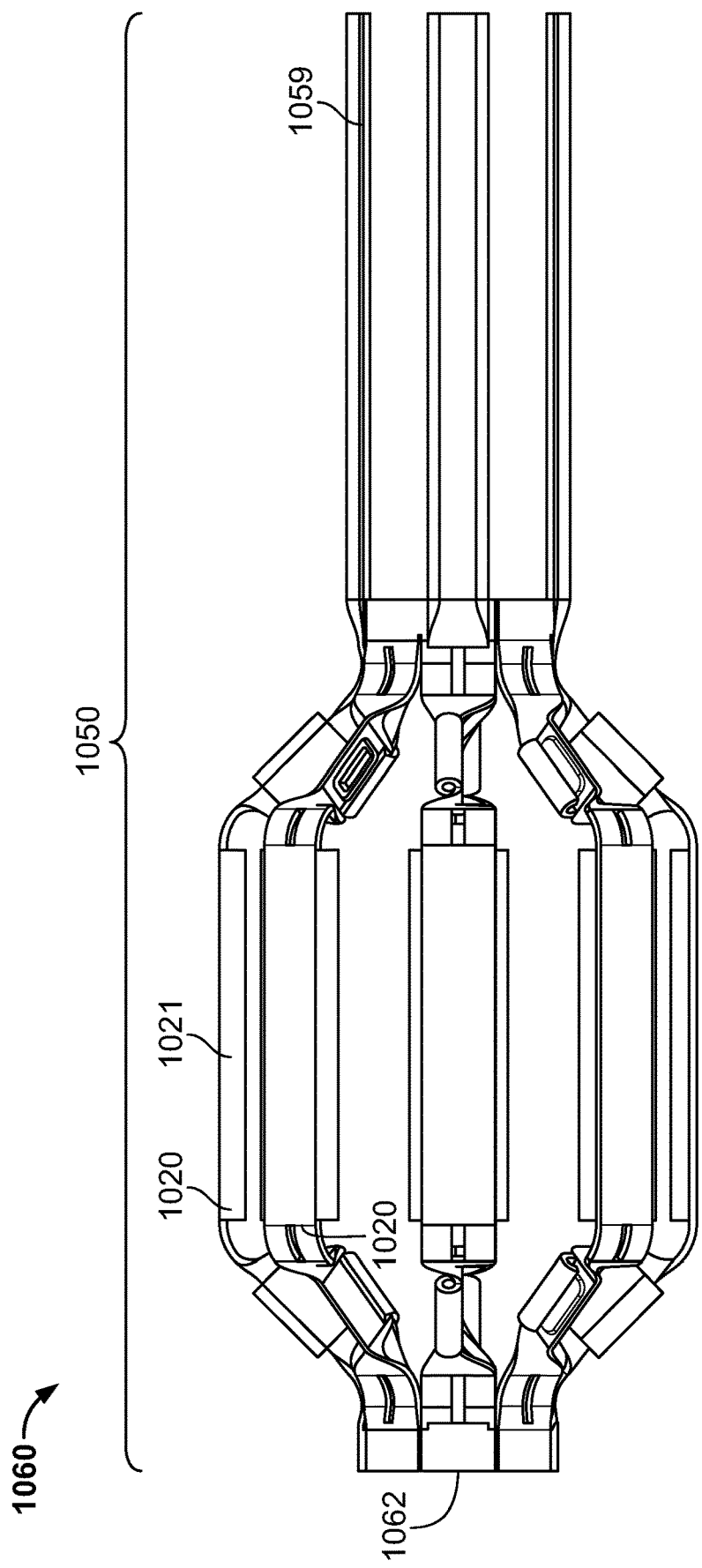
FIG. 10B is a side view illustration of the same embodiment of four cage arms combined together to form a complete basket-like cage in the expanded configuration of FIG. 10A.
Figure 10C:
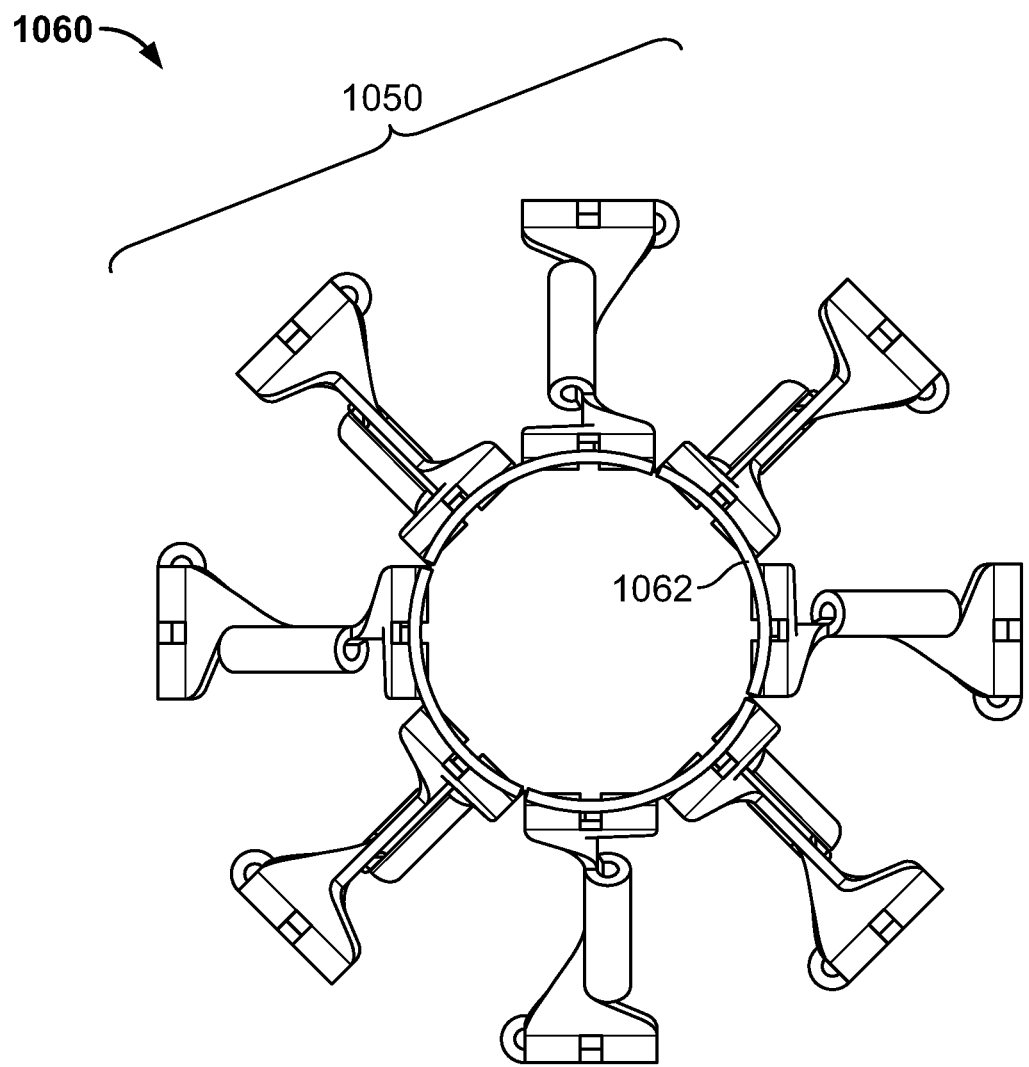
FIG. 10C is a front-on view illustration of the same embodiment of four cage arms combined together to form a complete basket-like cage in the expanded configuration of FIG. 10A.

FIGS. 10A, 10B, and 10C are oblique front, side, and front-on view illustrations respectively, of one embodiment of four cage arms 1050 combined together to form a complete basket-like cage 1060 in the expanded configuration. In various other embodiments, the cage includes fewer or more than four arms and takes on a variety of other shapes, including, but not limited to, an ellipse or a trapezoid. Referring simultaneously to FIGS. 10A and 10B, each cage arm 1050 comprises two cage support members 1020 and one elongate linear member 1059. The complete cage 1060 comprises four cage arms 1050 arranged together such that the distal ends of each cage arm 1050 come together to form a circle 1062 at the distal end of the device. The distal end of the cage 1060 is attached to the distal end cap (not shown) and inner shaft portion at the circle 1062. The four elongate linear members 1059 enclose a housing at the proximal end of the device and are spaced apart from one another in 90 degree increments. In one embodiment, the housing contains the motor to drive the device and a battery to power the motor. In addition, in one embodiment, the housing includes a locking mechanism to couple with the positioning shaft. In the expanded configuration, the eight central rectangular portions 1021 of each cage support member 1020 are expanded out away from the center of the device and from one another. FIG. 10C illustrates the circle 1062 formed at the distal end of the cage 1060 by the combination of four cage arms 1050.

Figure 11A:
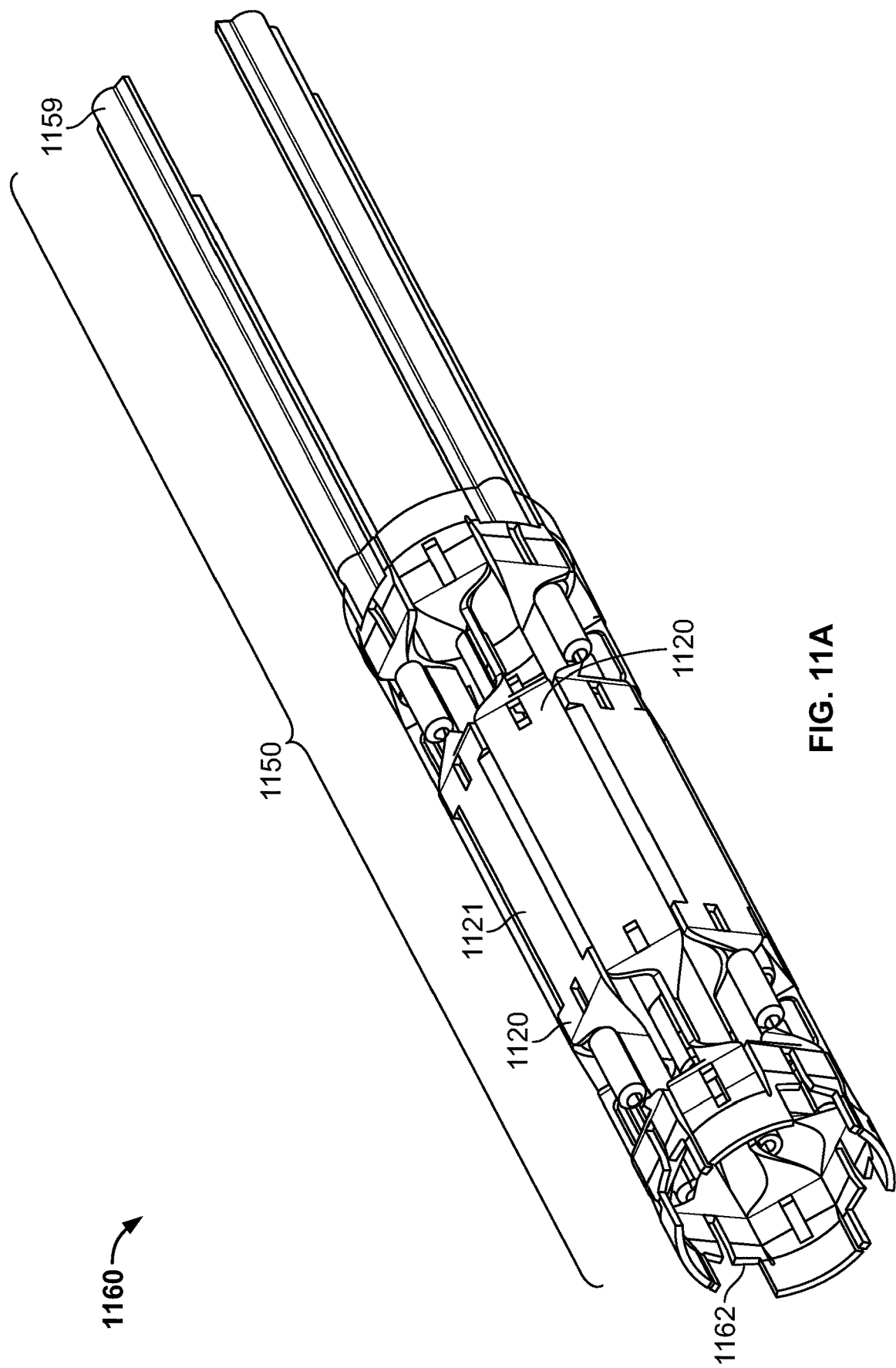
FIG. 11A is an oblique, front view illustration of one embodiment of four cage arms combined together to form a complete basket-like cage in the collapsed configuration.
Figure 11B:
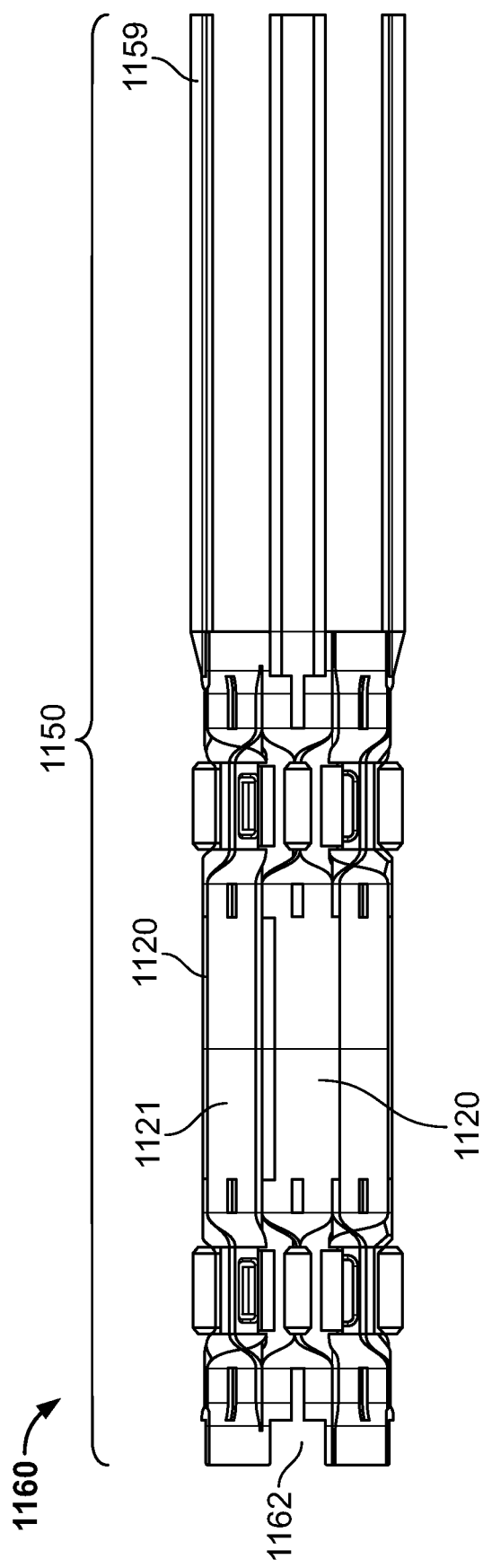
FIG. 11B is a side view illustration of the same embodiment of four cage arms combined together to form a complete basket-like cage in the collapsed configuration of FIG. 11A.
Figure 11C:
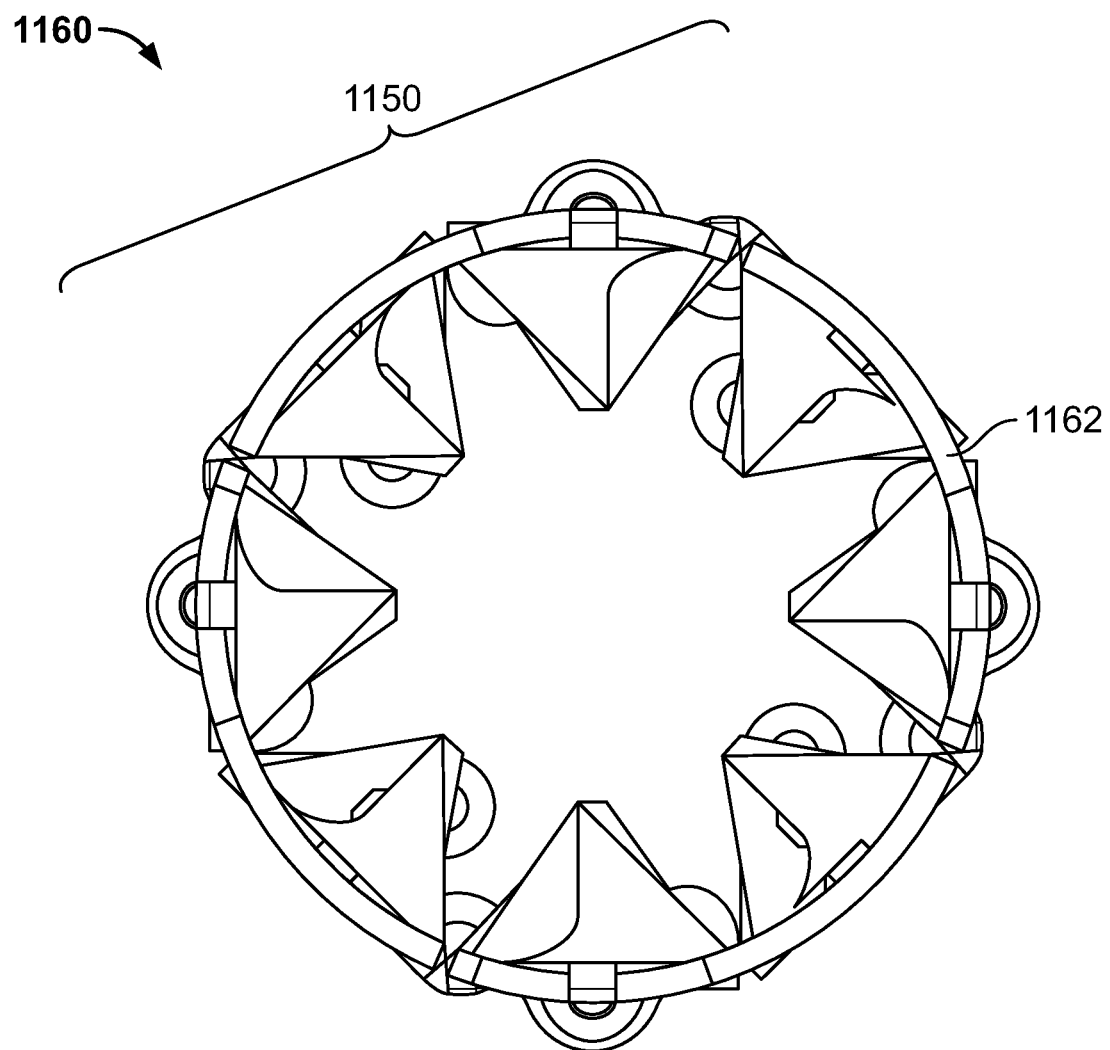
FIG. 11C is a front-on view illustration of the same embodiment of four cage arms combined together to form a complete basket-like cage in the collapsed configuration of FIG. 11A.

FIGS. 11A, 11B, and 11C are oblique front, side, and front-on view illustrations respectively, of one embodiment of four cage arms 1150 combined together to form a complete basket-like cage 1160 in the collapsed configuration. Referring simultaneously to FIGS. 11A and 11B, each cage arm 1150 comprises two cage support members 1120 and one elongate linear member 1159. The complete cage 1160 comprises four cage arms 1150 arranged together such that the distal ends of each cage arm 1150 come together to form a circle 1162 at the distal end of the device. The distal end of the cage 1160 is attached to the distal end cap (not shown) and inner shaft portion (not shown) at the circle 1162. The four elongate linear members 1159 enclose a housing (not shown) at the proximal end of the device and are spaced apart from one another in 90 degree increments. In the collapsed configuration, the eight central rectangular portions 1121 of each cage support member 1120 are compressed in toward the center of the device and are in contact with one another. FIG. 11C illustrates the circle 1162 formed at the distal end of the cage 1160 by the combination of four cage arms 1150.

Figure 12A:
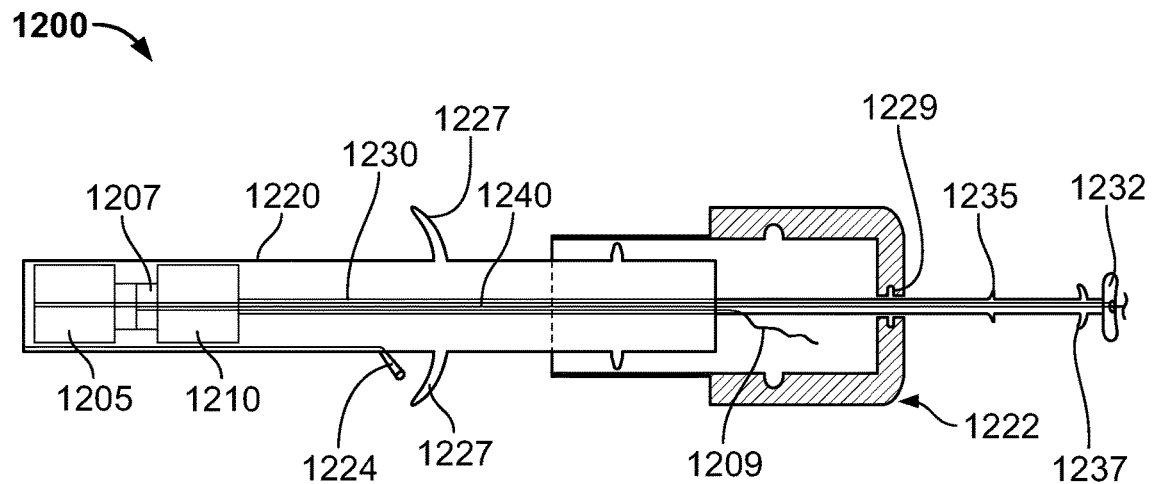
FIG. 12A is a side view illustration on one embodiment of an arterial closure device, depicting the arterial closure discs of the device positioned within a delivery sheath.

FIG. 12A is a side view illustration on one embodiment of an arterial closure device 1200, depicting the arterial closure discs 1205, 1210 of the device 1200 positioned within a delivery sheath 1220. The arterial closure device is used to seal the arteriotomy site after insertion or retrieval of the pumping device of the present specification. In one embodiment, the closure device 1200 includes a pair of opposing umbrella shaped discs 1205, 1210. The distal disc 1205 includes a concave-convex deployed shape wherein its inner concave surface contacts the inner wall of the artery and the proximal disc 1210 includes a concave-convex deployed shape wherein its inner concave surface contacts the outer wall of the artery. The discs 1205, 1210 are connected at their centers by a diaphragm 1207 having a lumen. Both discs 1205, 1210 are initially constrained inside an elongate delivery sheath 1220, having a lumen and proximal and distal ends, and are deployed and expanded by extending distally from the distal tip of the delivery sheath 1220.

The delivery sheath 1220 includes a delivery sheath head 1222 at its proximal end and handles 1227 along its length. The delivery sheath head 1222 includes a distal end that attaches to the proximal end of the sheath and a proximal end. The delivery sheath head 1222 and handles 1227 are used by the physician to manipulate the closure device 1200 during placement. The delivery sheath 1220 includes an elongate blood return tube 1224 having a proximal end and a distal end. The distal end of the blood return tube 1224 is positioned at the distal end of the delivery sheath 1220 and the proximal end of the blood return tube 1224 exits at a point between the distal and proximal ends of the delivery sheath 1220. The closure device 1200 includes a tamper tool 1230 for extending the discs 1205, 1210 beyond the distal end of the delivery sheath 1220. The tamper tool 1230 comprises an elongate shaft having a tamper tool lumen, a proximal end, and a distal end and extends within the lumen of the delivery sheath 1220. The distal end of the tamper tool 1230 abuts the proximal end of the proximal disc 1210. At its proximal end, the tamper tool 1230 includes a handle 1232 that extends beyond the proximal end of the delivery sheath head 1222. Positioned on the tamper tool 1230 distal to the handle 1232 are a distal rivet 1235 and a proximal rivet 1237. During placement of the discs 1205, 1210 the distal rivet 1235 and proximal rivet 1237 sequentially engage a groove 1229 positioned within the proximal end of the delivery sheath head 1222. A string 1209 is attached to the distal disc 1205 and extends through the lumen of the diaphragm 1207, through the center of the proximal disc 1210, and proximally through the tamper tool 1230 lumen.

During placement of the arterial closure discs 1205, 1210, the entire sheath system is advanced over the wire 1240 extending from the distal end of the pumping device. The wire 1240 extends through the tamper tool lumen and guides the closure device 1200. If arterial closure is being performed after removal of the pumping device, a separate guide wire is first introduced into the artery. For arterial closure after the insertion of the pumping device, the delivery sheath 1220 of the closure device 1200 is delivered through the existing arterial sheath used to insert the pumping device.

Figure 12B:
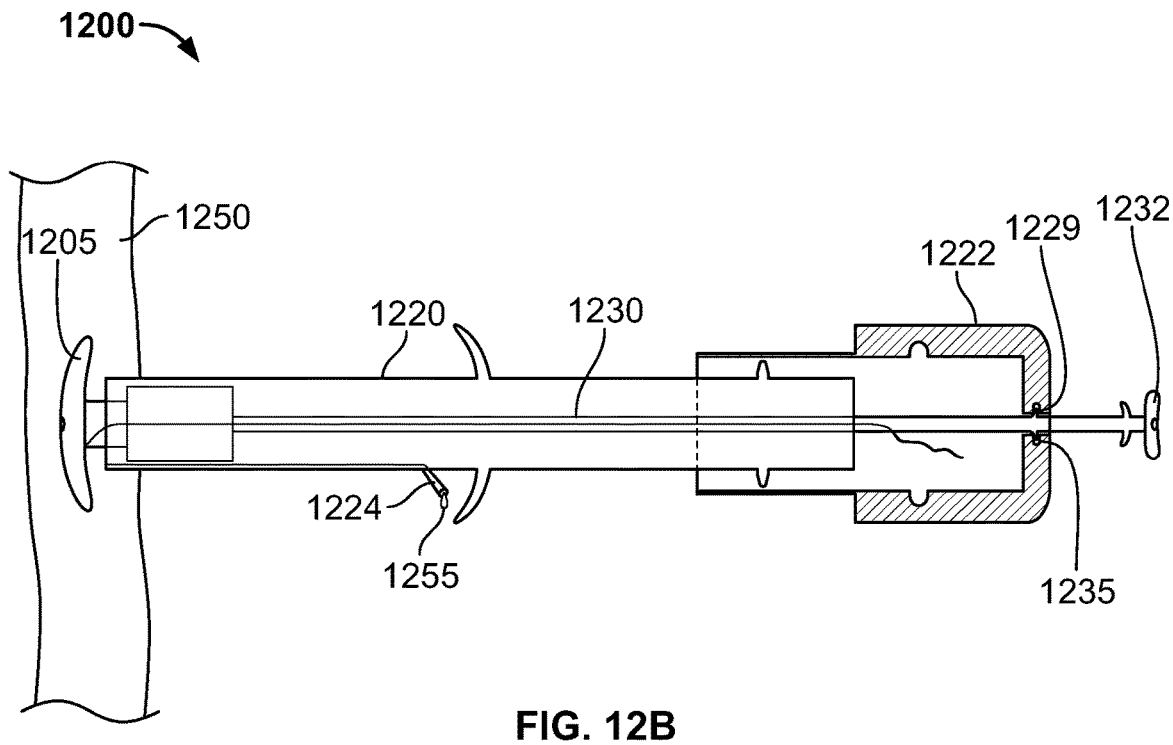
FIG. 12B is a side view illustration of the same embodiment of the arterial closure device of FIG. 12A, depicting the distal arterial closure disc expanded and deployed from the distal end of the delivery sheath.

FIG. 12B is a side view illustration of the same embodiment of the arterial closure device 1200 of FIG. 12A, depicting the distal arterial closure disc 1205 expanded and deployed from the distal end of the delivery sheath 1220. Once the distal end of the delivery sheath 1220 is positioned inside the artery 1250, as confirmed by the presence of blood 1255 at the proximal end of the blood return tube 1224, the distal disc 1205 of the closure device 1200 is pushed out with the tamper tool 1230. Once beyond the distal end of the delivery sheath 1220, the distal disc 1205 expands to its umbrella shape. The tamper handle 1232 is pushed distally into the delivery sheath head 1222 until the distal rivet 1235 engages the groove 1229, effectively locking the tamper tool 1230 in place. The entire closure device 1200 is then pulled back so that the umbrella shaped distal disc 1205 opposes the hole in the artery from the inside. The existing arterial sheath for inserting the pumping device is then removed and the delivery sheath 1220 is left just outside the artery 1250.

Figure 12C:
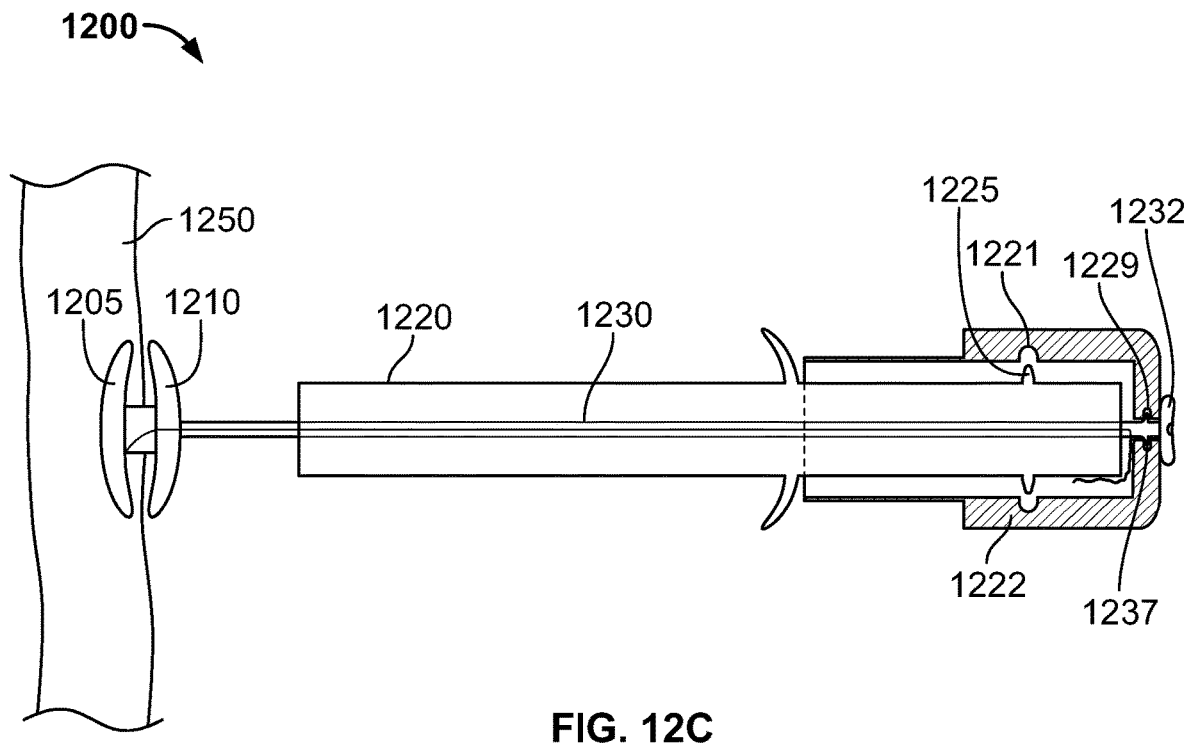
FIG. 12C is a side view illustration of the same embodiment of the arterial closure device of FIG. 12A, depicting both the distal and proximal arterial closure discs expanded and deployed from the distal end of the delivery sheath.

FIG. 12C is a side view illustration of the same embodiment of the arterial closure device 1200 of FIG. 12A, depicting both the distal 1205 and proximal 1210 arterial closure discs expanded and deployed from the distal end of the delivery sheath 1220. The reverse umbrella shaped proximal disc 1210 of the closure device 1200 is delivered to the outside of the artery 1250 by simultaneously pulling back the delivery sheath 1220 and pushing in the tamper tool handle 1232 until the delivery sheath head 1222 and tamper tool handle 1232 are fully apposed. In this position, the proximal rivet 1237 of the tamper tool 1230 engages the groove 1229 of the delivery sheath head 1222, effectively locking the tamper tool 1230 in place. In one embodiment, the delivery sheath head 1222 is pushed distally along the delivery sheath 1220, wherein the delivery sheath 1220 includes a rivet 1225 that engages a second groove 1221 within the delivery sheath head 1222, effectively locking the delivery sheath 1220 in place within the delivery sheath head 1222. The delivery sheath 1220, with the delivery sheath head 1222, and the tamper tool 1230 are then removed.

Figure 12D:
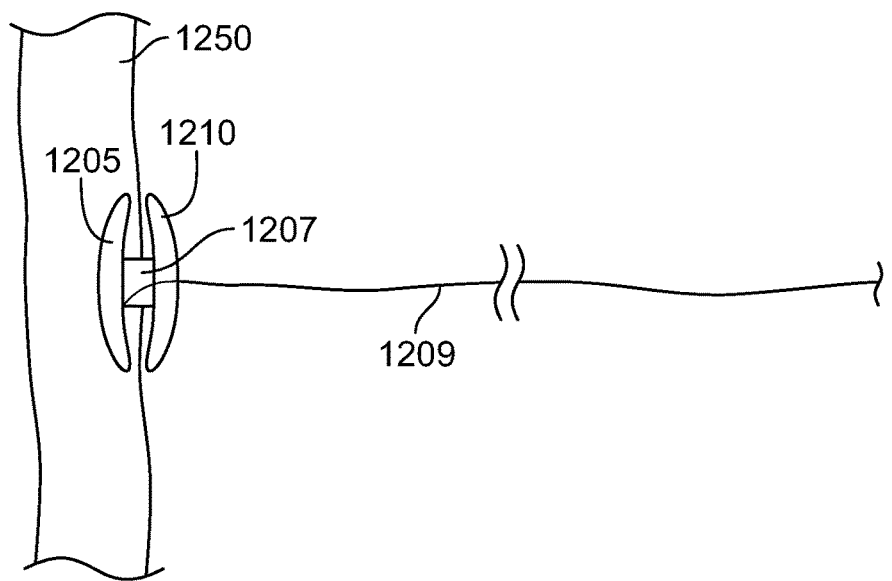
FIG. 12D is a side view illustration of one embodiment of the arterial closure discs fully deployed with the delivery sheath removed.

FIG. 12D is a side view illustration of one embodiment of the arterial closure discs 1205, 1210 fully deployed with the delivery sheath removed. The distal disc 1205 is depicted within the artery 1250 and the proximal disc 1210 is depicted outside the artery 1250. The two apposing discs 1205, 1210 with center diaphragm 1207 seal the arteriotomy site. Once both discs 1205, 1210 are in place, the sheath and tamper are pulled out, exposing only the string 1209 attached to the distal disc 1205. Once arteriotomy closure is confirmed, the string 1209 is cut below the skin. The guide wire in the center can be removed if necessary from the center diaphragm 1207 keeping the artery 1250 sealed.

Figure 12E:
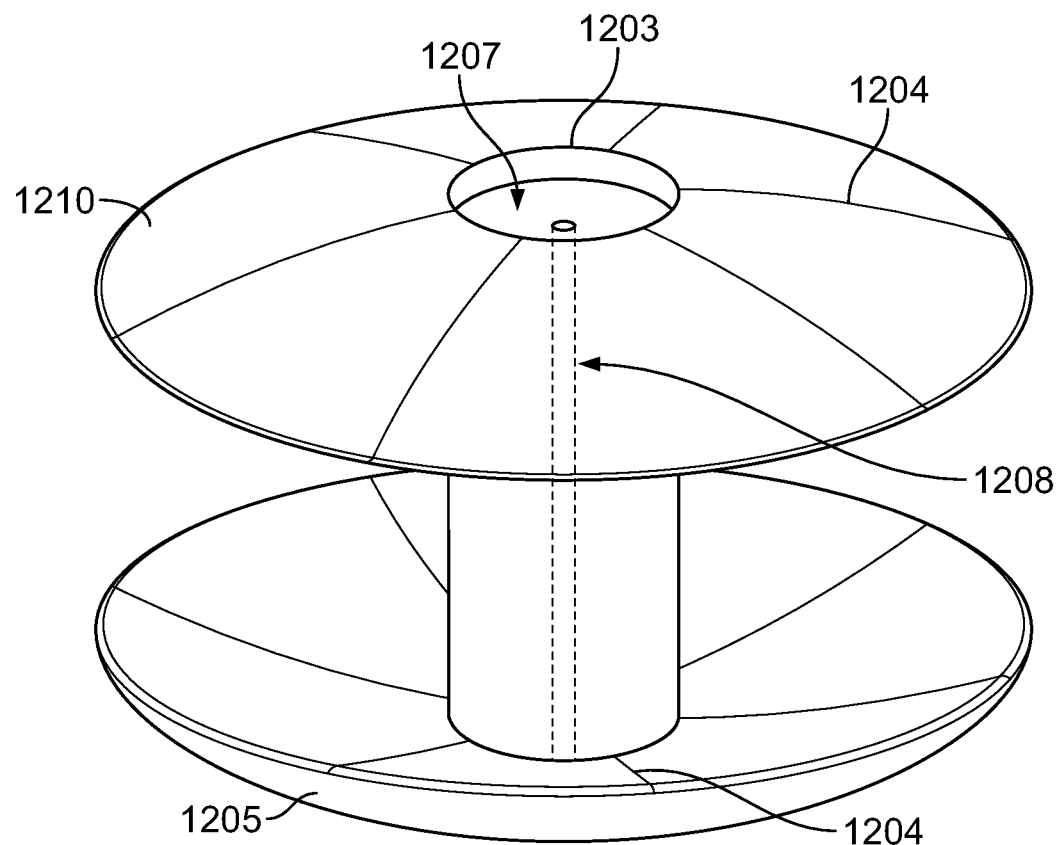
FIG. 12E is an illustration of one embodiment of the arterial closure discs, depicting the struts used to expand the discs to their deployed configuration.

FIG. 12E is an illustration of one embodiment of the arterial closure discs 1205, 1210, depicting the struts 1204 used to expand the discs 1205, 1210 to their deployed configuration. The discs 1205, 1210 are constricted and tubular shaped, as depicted in FIG. 12A, when constrained in the restraining sheath and expand into umbrella shaped discs 1205, 1210 outside the sheath, as depicted in FIG. 12E. The proximal surface 1203 of the proximal disc 1210 indicates the point where the tamper tool pushes on the discs to deploy them from the sheath. In one embodiment, the discs are made out of an expandable and biocompatible material. The discs 1205, 1210 include a diaphragm 1207 interconnecting them with a lumen 1208 in the center to accommodate the string and guide wire exiting the artery. Each disc 1205, 1210 also includes a hole at its center for accommodation of the string and guide wire. The radiating struts 1204 act to expand the discs into their umbrella shape upon deployment.

Figure 13:
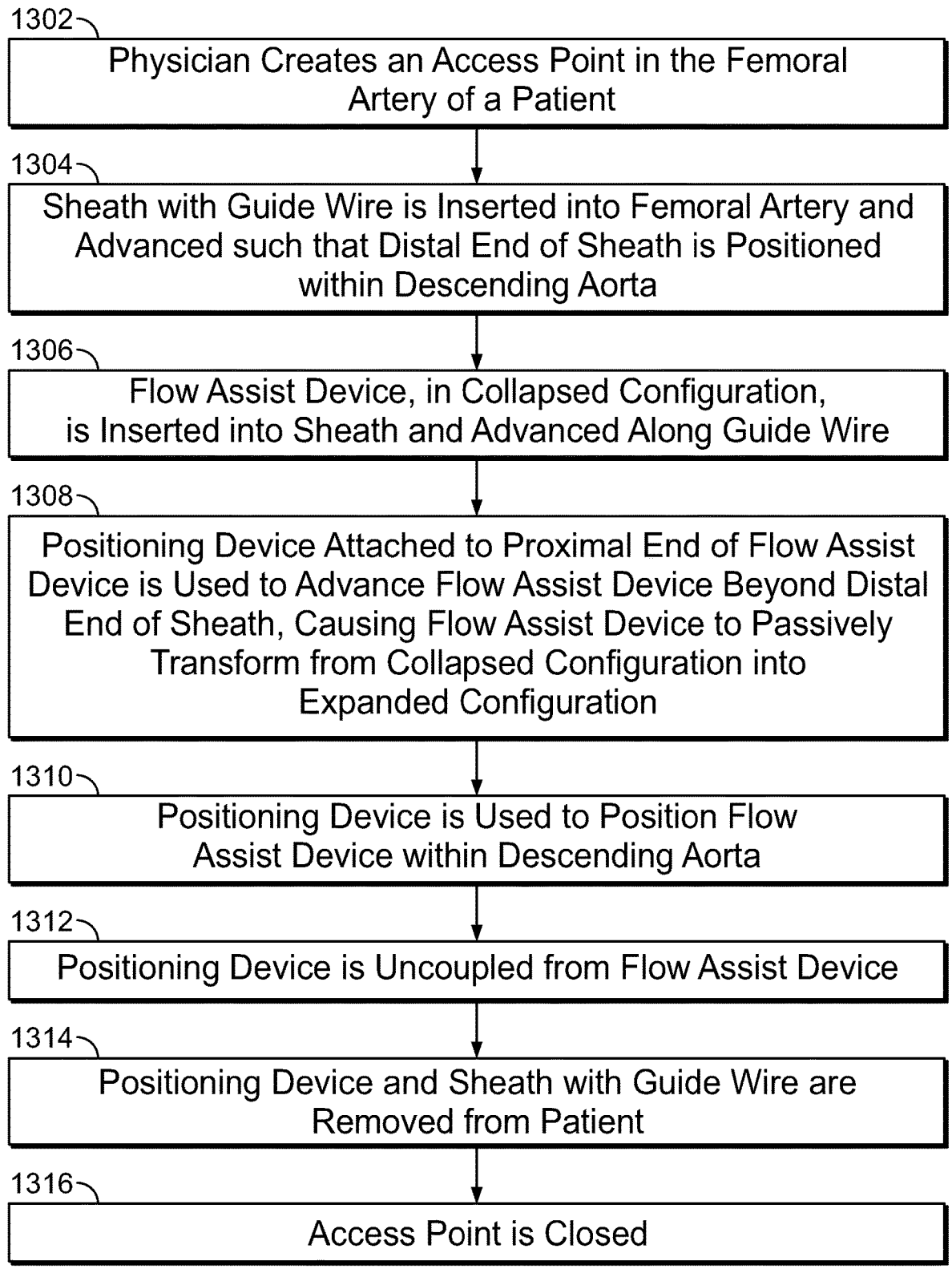
FIG. 13 is a flowchart illustrating the steps involved in implanting the hemodynamic flow assist device in the descending aorta of a patient, in accordance with one embodiment of the present specification.

FIG. 13 is a flowchart illustrating the steps involved in implanting the hemodynamic flow assist device in the descending aorta of a patient, in accordance with one embodiment of the present specification. At step 1302, a physician creates an access point in the femoral artery of a patient. A sheath with a guide wire is inserted into the femoral artery and advanced such that the distal end of the sheath is positioned within the descending aorta at step 1304. Then, at step 1306, the hemodynamic flow assist device, in the collapsed configuration, is inserted into the sheath and is advanced along the guide wire. At step 1308, a positioning device attached to the proximal end of the flow assist device is used to advance the flow assist device beyond the distal end of the sheath, causing the flow assist device to passively transform from its collapsed configuration into its expanded configuration. At step 1310, the positioning device is used to position the flow assist device within the descending aorta. The positioning device is then uncoupled from the flow assist device at step 1312. At step 1314, the positioning device and sheath with guide wire are removed from the patient. The access point is then closed at step 1316.

Figure 14:
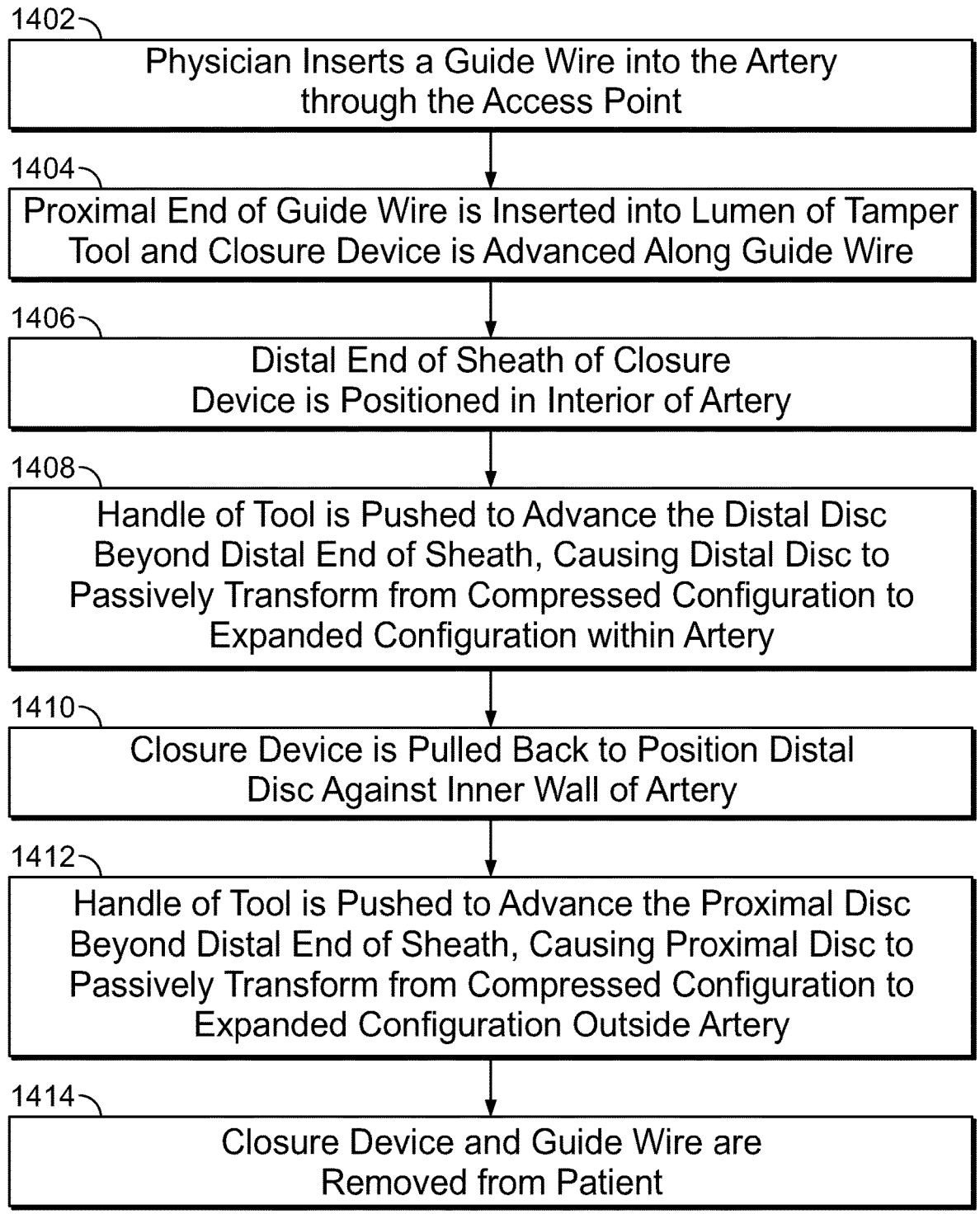
FIG. 14 is a flowchart illustrating the steps involved in closing an arterial access point using the arterial closure device, in accordance with one embodiment of the present specification.

FIG. 14 is a flowchart illustrating the steps involved in closing an arterial access point using the arterial closure device, in accordance with one embodiment of the present specification. At step 1402, a physician inserts a guide wire into the artery through the access point. The proximal end of the guide wire is inserted into the lumen of the tamper tool and the closure device is advanced along the guide wire at step 1404. The distal end of the closure device is positioned in the interior of the artery at step 1406. Then, at step 1408, the handle of the tamper tool is pushed to advance the distal disc beyond the distal end of the sheath, causing the distal disc to passively transform from its compressed configuration into its expanded configuration within the artery. At step 1410, the closure device is pulled back to position the distal disc against the inner wall of the artery. Then, at step 1412, the handle of the tamper tool is pushed to advance the proximal disc beyond the distal end of the sheath, causing the proximal disc to passively transform from its compressed configuration into its expanded configuration outside the artery. The closure device and guide wire are then removed from the patient at step 1414.

A variety of optional components may be used or implemented with each of the aforementioned embodiments. Those optional components include sensors, cameras, modified cage sizes, different energy management or battery charging systems, removability features, migration prevention, and positioning components.

Sensors and Camera(s)

Referring back to FIG. 1, in an embodiment, at least one of sensors 132, 134, and 136 includes an accelerometer. The accelerometer is configured to detect increased movement by the patient, signifying increased physical activity. The accelerometer generates data indicative of the physical activity of the patient, and, based on the heightened physical activity, the device increases blood flow to meet demands. In an embodiment, the accelerometer generates data indicative of physical activity, such as walking or climbing stairs and transmits that data to a controller, which is in data communication with the pump. The controller uses data from the accelerometer to manipulate the rotational speed of the rotating pump shaft of cardiovascular flow assist device 100 in the expanded, deployed configuration. Conversely, if the accelerometer detects decreased physical activity, such as sitting or laying down, the controller will cause the pump to slow down and, accordingly, the device will decrease blood flow.

In another embodiment, the device includes a flow meter. In an embodiment, the flow meter is a MEMS sensor. In an embodiment, referring to FIG. 1, at least one of sensors 132, 134, and 136, include the flow meter. In some embodiments, four sensors 134 towards the distal end and four sensors 136 towards the proximal end of the device are flow meters. In an embodiment, the flow meter detects surface tension of the blood, which provides fluid velocity. In one embodiment, the surface tension data is used to measure pressure of the flow of blood.

Information pertaining to the fluid velocity and a size of the cage is used to derive a cross-section of the device. The presence of four sensors on each end (distal and proximal) of the device enables recreating a three-dimensional (3D) image of the events that occur at each port of the diameter of the aorta. In one embodiment, the flow meter sends data to the patient via the cable attached to the proximal end of the device. Data collected by the flow meter(s) in combination with other information, such as the dimensions of the device and the velocity of blood, may be used to calculate a volume (in liters per minute) to titrate.

In an embodiment, the flow meter generates data indicative of the physical activity of the patient, and, based on the heightened physical activity, the device increases blood flow to meet demands by increasing the rotational speed of the rotating pump shaft. The flow meter generates data indicative of physical activity, such as walking or climbing stairs and transmits that data to a controller, which is in data communication with the pump. The controller uses data from the flow meter to manipulate the rotational speed of the rotating pump shaft of cardiovascular flow assist device 100 in the expanded, deployed configuration. Conversely, if the flow meter detects decreased blood flow, which may occur when a person sits or lays down, the controller will cause the pump to slow down and, accordingly, the device will decrease blood flow.

In an embodiment, at least one of sensors 132, 134, and 136, includes an EKG sensor. The EKG sensor measures cardiac electrical potential waveforms (voltages produced during the contraction of the heart). The electrical activity of the heart that is measured by the EKG sensor may be used to detect instances of cessation of heartbeats. In an embodiment, device 100 delivers an electric shock when the EKG sensor indicates instance of cessation of heartbeats, thus functioning as a defibrillator or as a pacemaker. In an embodiment, the heart activity is detected by the EKG sensor on a beat-to-beat basis, which is recorded and/or monitored in real time. The real time feedback provided by the EKG sensor may be used to drive an algorithm that is, in turn, used to control rotational speed of the rotating pump shaft of cardiovascular flow assist device 100 in the expanded, deployed configuration. Sensor information on heart's beat-to-beat basis, compared to information pertaining blood flow of the patient, helps overcome challenges in understanding depletion in blood flow due to heart-related diseases versus Von Willebrand factor.

In an embodiment, distal end cap 106 includes at least one camera. In one embodiment, the camera is positioned proximate the distal end of the device. In one embodiment, the camera is an infra-red (IR) charged coupled device (CCD) camera. Each camera positioned on distal end cap 106 is accompanied with at least one light source to provide light within the field of view of the camera. In an embodiment, the light source is a Light Emitting Diode (LED). Images captured by the camera enable real-time viewing of the blood flow.

In an embodiment, the sensors 132, 134, 136, and camera(s) are controlled externally through an interface provided to the operator of the device. Sensor and camera wires connect the sensors 132, 134, 136, and camera(s), to the interface via patient cable 108.

Cage Size

Figure 15A:
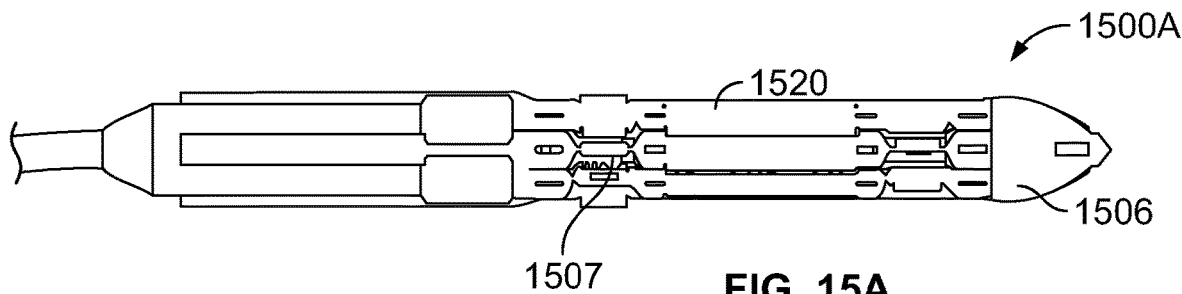
FIG. 15A illustrates an embodiment of a cardiovascular flow assist device, at a first stage, when converting from an initial collapsed, deliverable configuration to various expanded, deployed configurations.
Figure 15B:
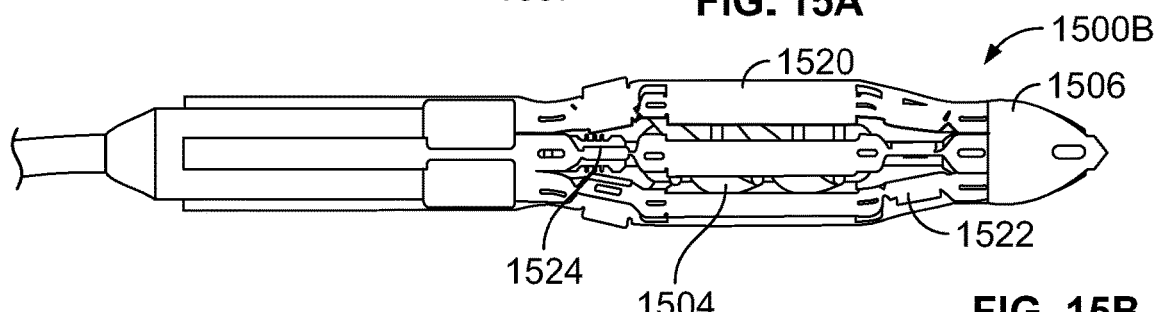
FIG. 15B illustrates an embodiment of a cardiovascular flow assist device, at a second stage, when converting from an initial collapsed, deliverable configuration to various expanded, deployed configurations.
Figure 15C:
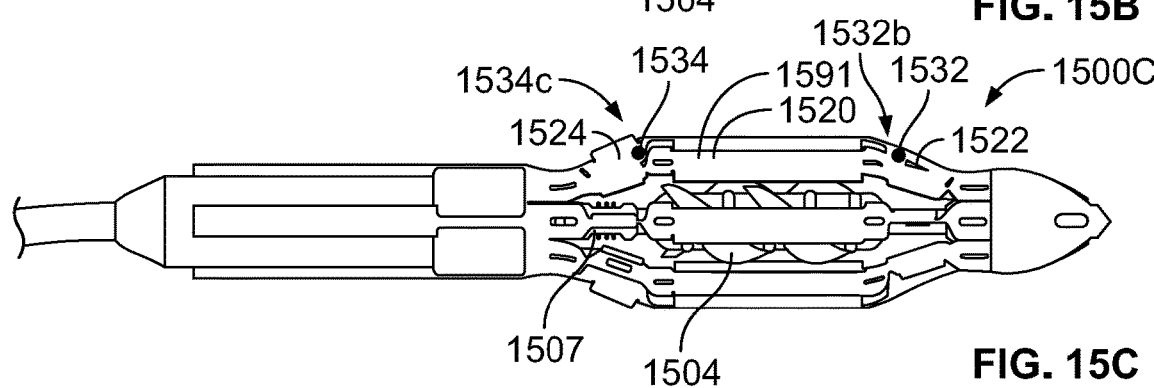
FIG. 15C illustrates an embodiment of a cardiovascular flow assist device, at a third stage, when converting from an initial collapsed, deliverable configuration to various expanded, deployed configurations.
Figure 15D:
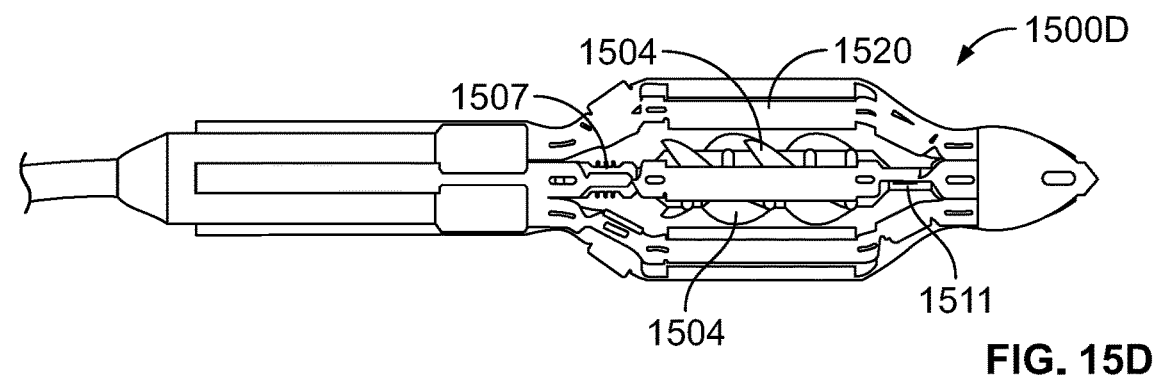
FIG. 15D illustrates an embodiment of a cardiovascular flow assist device, at a fourth stage, when converting from an initial collapsed, deliverable configuration to various expanded, deployed configurations.
Figure 15E:
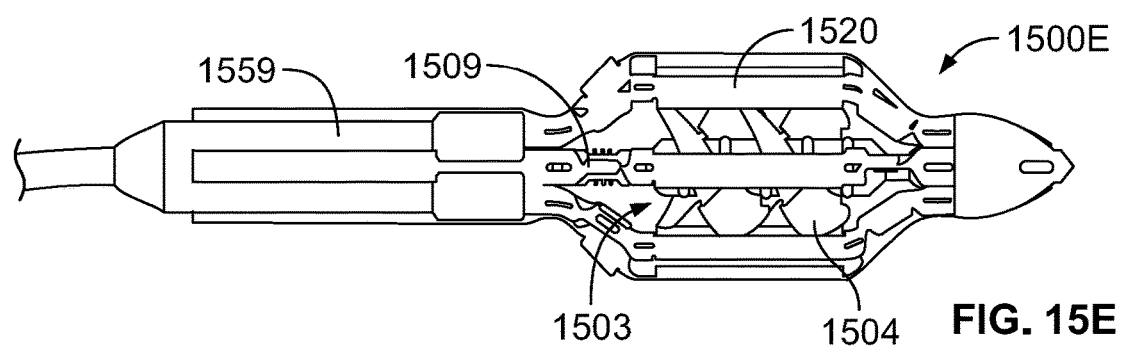
FIG. 15E illustrates an embodiment of a cardiovascular flow assist device, at a fifth stage, when converting from an initial collapsed, deliverable configuration to various expanded, deployed configurations.

In an embodiment, a mechanism is provided for changing a size of the cage based on the size of a patient's aorta. FIGS. 15A to 15E illustrate one embodiment of cardiovascular flow assist device 1500, at various stages from an initial collapsed, deliverable configuration seen in FIG. 15A, to various expanded, deployed configurations seen in FIGS. 15B to 15E. As seen in FIG. 15A, cage support members 1520 of the collapsed device 1500A are seen in their fully compressed state, collapsed toward the center of the device and coming to rest in contact with one another. As can be seen in FIGS. 15A, 15B, 15C, 15D, 15E, the diameter of device 1500B, 1500C, 1500D, and 1500E when in the expanded configuration, particularly the diameter formed by the cage support members 1520, is larger than the diameter of the device 1500A when in the collapsed configuration. As can also be seen in FIGS. 15A to 15E, the length of the device 1500B, 1500C, 1500D, and 1500E when in the expanded configuration is shorter than the length of the device 1500A when in the collapsed configuration. Additionally, the length of device 1500E in the most-expanded configuration, is the shortest. The length of devices 1500A to 1500E can be seen reducing as the device changes from the collapsed configuration through various expanded configurations to the most expanded configuration (device 1500E). Distal end cap 1506 also moves with the expansion of the device from device 1500A to 1500E. Each FIGS. 15A, 15B, 15C, and 15D, provides a configuration that may be adapted for differently sized of aortas of different patients. Configuration of the device can be changed from one to another until a suitable configuration is achieved where the cage formed by the cage support members 1520 is able to fit snugly within the aorta.

As described previously in context of FIGS. 5A, 5B and 9A-D, a helical screw pump 1503 is connected at its proximal end, via a coupling 1507, to a first motor 1509. Operating the first motor 1509 drives the impeller on pump 1503, causing rotation of blades 1504. In one embodiment, the inner shaft portion 1511 of pump 1503 extends through to the coupling 1507 and is slidably movable within the pump's 1503 outer shaft portion segments. This allows the device 1500 to lengthen and shorten during compression and expansion respectively. The distal end of the inner shaft portion 1511 of pump 1503 and the distal ends of the cage support members 1520 attach to the distal end cap 1506. In an embodiment, a second pump is connected to the elongate linear members 1559 attached to the four proximal quarter-circles formed by the pairs of cage support members 1520. The second pump is attached to the elongate linear members 1559 through a housing supporting the second motor at the proximal end of the device. As mentioned earlier, the four to eight elongate linear members 1559 of the cage enclose a housing at the proximal end of the device 1500 and are spaced apart from one another in 90 degree increments. The housing contains the second motor. In an embodiment, operation of the second pump drives the movement of the cage so as to move from a collapsed configuration to an expanded configuration, and vice-versa. Operation of the second pump enables variation in size of the device 1500, specifically variation in the diameter of the cage and the length of the device 1500. In an embodiment, a diameter of the cage is varied from collapsed to expanded configurations with three variable sizes: 18+/−2 mm, 21+/−2 mm, and 24+/−2 mm, or any increment therein.

In embodiments, such as those described in context of FIG. 10, the cage support members 1520 of the device expand to form a basket-like cage in the shape of a trapezoid, as seen in FIGS. 15B-15E. In various other embodiments, the cage includes fewer or more than four support members 1520 and takes on a variety of other shapes, including, but not limited to, an ellipse.

In some embodiments, one or more sensors 1532 and 1534 located on distal and proximal hinged portions 1522 and 1524 of the cage support members 1520 provide information about the size of the cage relative to walls of the aorta within which it is placed. In some embodiments, sensors 1532 and 1534 are strain gauge sensors. In some embodiments, sensors 1532 and 1534 are positioned at locations 1532b and 1534c respectively, which correspond to a first location 1532b at a first junction between distal hinge portion 1522 and a strut 1591 of support member 1520 and a second location 1534c at a second junction between the strut 1591 and proximal hinge portion 1524 of support member 1520. In some embodiments, data from sensors 1532 and 1534 is transmitted to a microprocessor of the device which is configured to calculate an angle at said first and second locations 1532b, 1534c to determine the shape and size of the cage. The microprocessor can then control a motor of the device to adjust the shape and size of the cage. In some embodiments, the microprocessor and motor are contained within a housing at a proximal end of the device. In some embodiments, the housing has a diameter of 5 mm. In some embodiments, at least one MEMS sensor shows the angle of displacement of the cage within the aorta. The cage shape, size, and symmetricity is monitored by strain cells or MEMS sensors embedded in any of the hinge portions 921, 922, 924 (described with respect to FIG. 9C) and 1922, 1924 (described with respect to FIG. 19A). In some embodiments, the sensors are used to determine if the cage has symmetricity and a trapezoidal profile.

In some embodiments, the first motor 1503 (shown in FIG. 15E) includes a tachometer and a Hall Effect sensor (emag). The pressure and hall sensor measurements indicate when the walls of the cage come in to contact with the inner walls of the aorta, thereby providing a diameter of the cage. In embodiments, the first motor 1503 provides biofeedback when the cage touches walls of the aorta and a resistance from the aorta is sensed. The first motor feedback is used to determine contact of the cage with the aorta and to provide data on the size (diameter) of the cage in the expanded configuration. A computing device is connected either through a wire or wirelessly, to the first motor, so as to provide the information about the cage's expansion relative to aortic walls. As a result, the active cage in accordance with embodiments of the present specification can be controlled to adjust according to aortic resistance. In one embodiment, once aortic resistance is sensed, the memory shape of the cage goes back to 30% open. Beyond 30% opening, the cage may have to overcome the weakness of the shape memory alloy (Nitinol). The cage may be further opened by controlling the cage through the second motor. In some embodiments, the shape memory of the cage is responsible for the initial opening of the cage and then the second motor is responsible for adjusting the cage size/opening in relation to aortic resistance. In the compressed configuration, the cage members or components are aligned in a substantially linear shape. The inherent shape memory properties of a shape memory alloy, such as Nitinol, are preferable to cause the initial opening of the cage as an outside manipulative source, such as a motor, could cause the linear shape of the cage to buckle or bend during opening. In certain embodiments, after the cage has opened to a certain percentage, such as 30%, due to its shape memory property, a motor is used to fine-tune and adjust the size and shape of the opened cage.

Figure 15F:
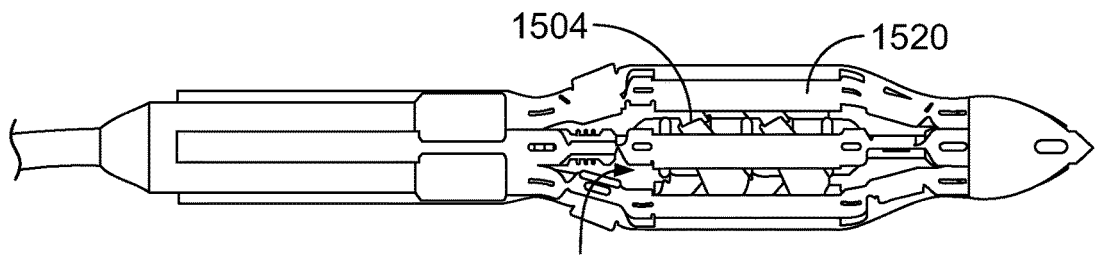
FIG. 15F illustrates an embodiment of a cardiovascular flow assist device, at a sixth stage, when converting from an initial expanded, deployed configuration to various collapsed configurations.
Figure 15G:
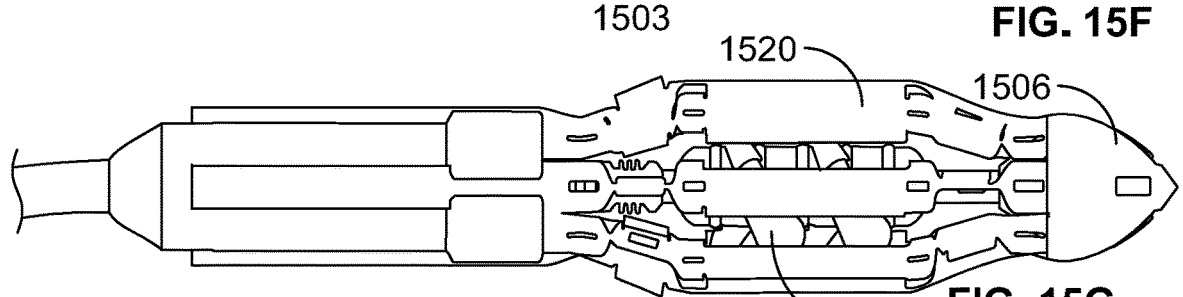
FIG. 15G illustrates an embodiment of a cardiovascular flow assist device, at a seventh stage, when converting from an initial expanded, deployed configuration to various collapsed configurations.
Figure 15H:
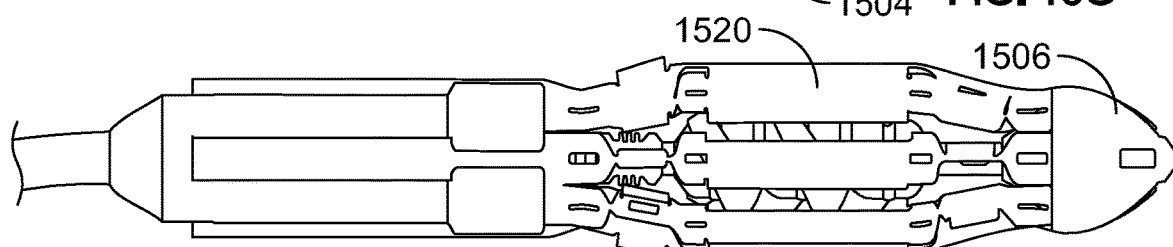
FIG. 15H illustrates an embodiment of a cardiovascular flow assist device, at an eighth stage, when converting from an initial expanded, deployed configuration to various collapsed configurations.
Figure 15I:
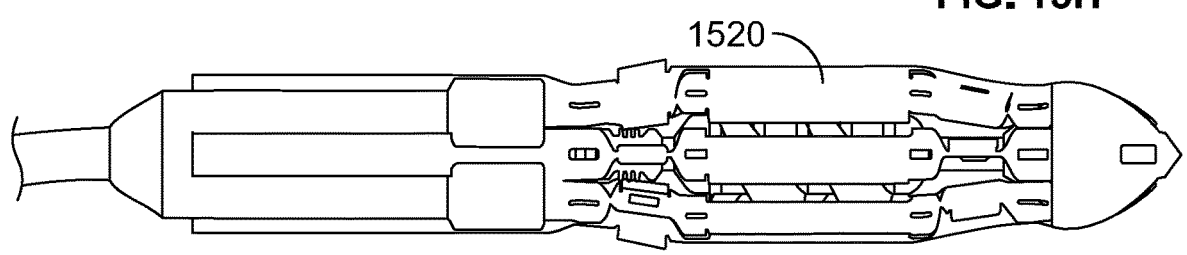
FIG. 15I illustrates an embodiment of a cardiovascular flow assist device, at a ninth stage, when converting from an initial expanded, deployed configuration to various collapsed configurations.
Figure 15J:
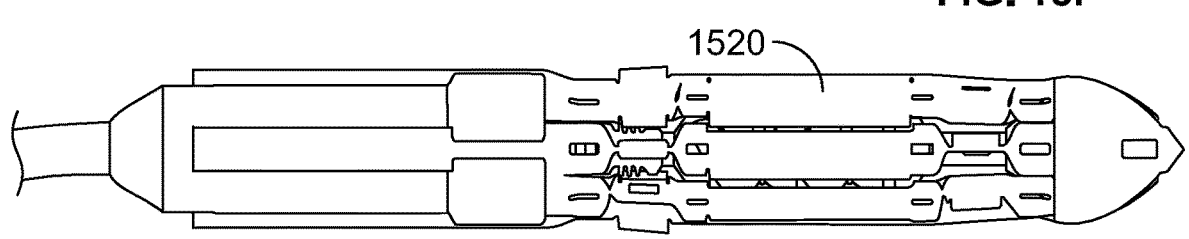
FIG. 15J illustrates an embodiment of a cardiovascular flow assist device, at a tenth stage, when converting from an initial expanded, deployed configuration to various collapsed configurations.
Figure 15K:
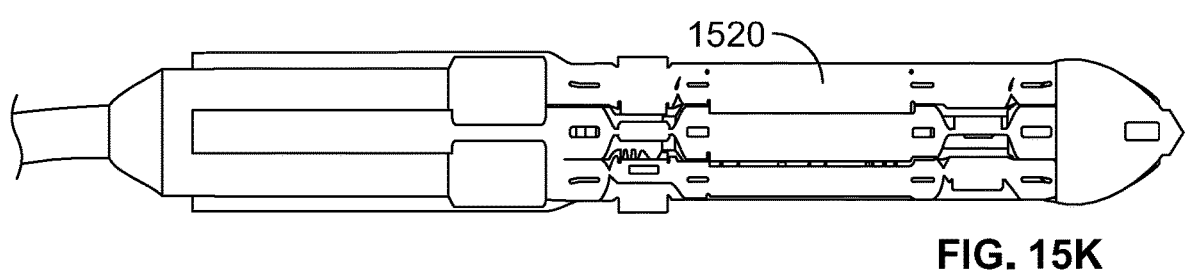
FIG. 15K illustrates an embodiment of a cardiovascular flow assist device, at an eleventh stage, when converting from an initial expanded, deployed configuration to various collapsed configurations.

FIGS. 15F, 15G, 15H, 15I, 15J, and 15K, illustrate the same embodiment of cardiovascular flow assist device 1500, at various stages from expanded, deployed configurations seen in FIG. 15F to a collapsed configuration seen in FIG. 15K. As seen from FIGS. 15F to FIG. 15K, as the device 1500 collapses, sensors on cage support members 1520 of the cage are able to detect proximity of the cage support members 1520 to the impeller on the first motor 1503. In an embodiment, when cage support members 1520 of the cage touch the impeller, the first motor 1503 is rotated backwards in order to move blades 1504 inwards. As mentioned earlier, the blades 1504 are composed of a shape memory metal to allow for compression and expansion of blades 1504. In one embodiment, the shape memory metal is Nitinol. Therefore, blades 1504 that comprise the impeller, wrap about pump's 1503 outer shaft portion as the device collapses. Once the impeller has wrapped itself around the shaft of pump 1503, the device is considered to have reached its collapsed state/configuration seen in FIG. 15K.

Self-Charging

As mentioned earlier, in an embodiment, the four elongate linear members of the cage enclose a housing at the proximal end of the device and are spaced apart from one another in 90 degree increments. In one embodiment, the housing contains the motor to drive the device and a battery to power the motor. The battery powers the motor that is attached to the proximal end of the first shaft for coaxially rotating the first shaft. The at least one set of collapsible blades also rotate with the first shaft, to pump blood through the device. In an embodiment, the battery is a self-charging battery or inverter, wherein the self-charging battery is charged by the unassisted flow of blood turning the blades when a patient having the device implanted is in the resting or prone position.

Figure 16B:
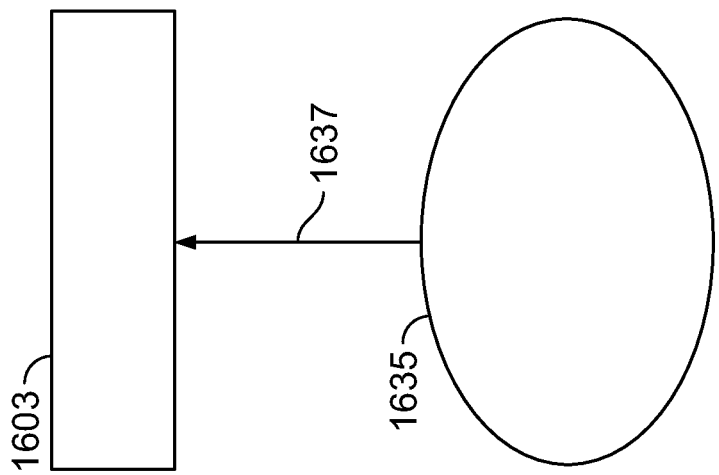
FIG. 16B illustrates a direction of flow of electrical power between the pump and battery at different times.
Figure 16A:
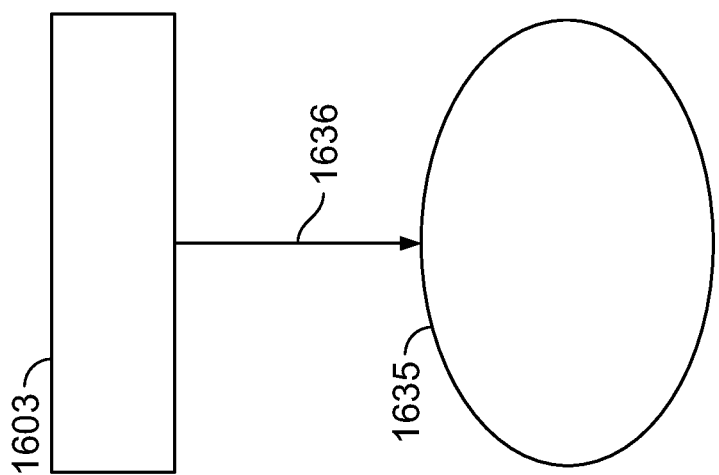
FIG. 16A illustrates a direction of flow of electrical power between the pump and battery at different times.

In an embodiment, the battery is charged when the motor is not being powered by the battery. Specifically, in the resting or prone position, the motor is not being powered by the battery and the heart pumps the blood that causes the impeller to move. The blood may flow over the impeller without creating resistance. Kinetic energy generated by the movement of the impeller is converted to electrical power that is used to charge the battery. FIGS. 16A and 16B illustrate direction of electrical power that flows between the pump 1603 and battery 1635 at different times. Electrical power flows in a direction 1636 from pump 1603 to battery 1635 when the patient is in the resting position, or when the pump is not receiving power. Electrical power flows in a direction 1637 from battery 1635 to pump 1603 when the patient is awake and/or moving. In an embodiment, body heat is used to charge the battery. In another embodiment, a wireless Radio Frequency (RF) system is embedded at the proximal end of the device to enable wireless electromagnetic powering of the device.

Migration Prevention

Embodiments of anchoring mechanisms are now discussed that prevent migration of the hemodynamic flow assist device in either the cranial direction or the caudal direction.

Figure 17A:
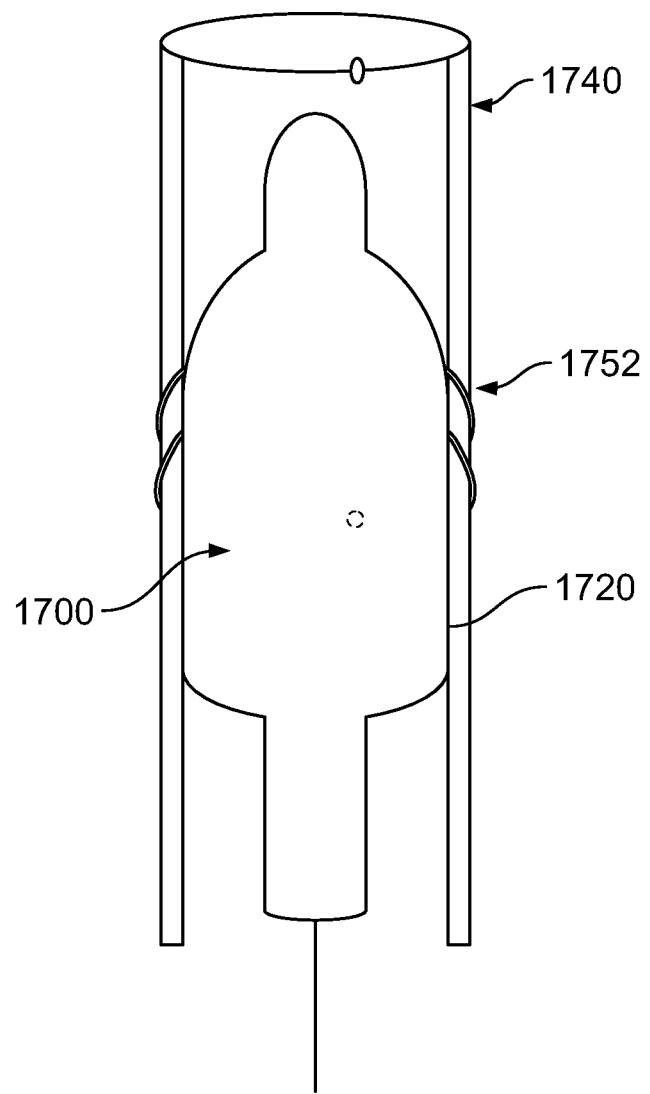
FIG. 17A illustrates an anchoring mechanism in the form of a cone-shaped cage and hooks on the distal end of cage supporting members to resist dislodgement within a patient's aorta, in accordance with an embodiment of the hemodynamic flow assist device of the present specification.

In one embodiment, the cage of the hemodynamic flow assist device has a cone shape configured to resist dislodgement within a patient's aorta. Dislodgement of the flow assist device may cause the device to move or migrate within the aorta. Unintended migration, specifically caudal migration, is prevented by a mechanism that anchors the device within the aorta. FIG. 17A illustrates an anchoring mechanism for a device 1700 placed within an aorta 1740 in the form of a cone-shaped cage, in accordance with an embodiment of the hemodynamic flow assist device of the present specification.

FIG. 17A also illustrates an additional anchoring mechanism where the cage of the hemodynamic flow assist device includes hooks 1752 on the distal end of cage supporting members 1720 to resist dislodgement within patient's aorta 1740. In an embodiment, at least a pair of diametrically opposing hooks 1752 are positioned on the outer wall of the cage supporting members 1720 on the circumference of the cage. Each hook 1752 is attached to cage supporting member 1720 at one end, and the other end protrudes outwards, away from the cage, towards the inners walls of aorta 1740.

Figure 17B:
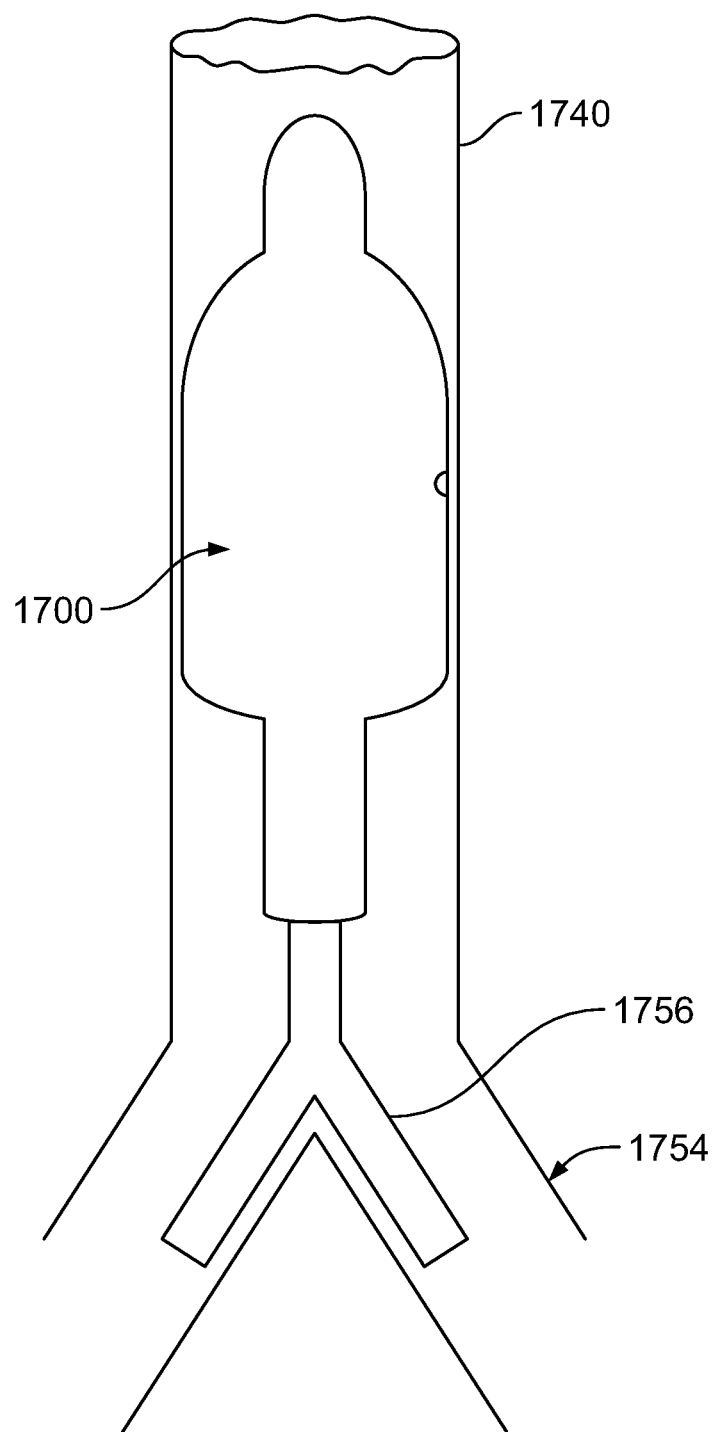
FIG. 17B illustrates yet another embodiment of an anchoring mechanism where the proximal end of the hemodynamic flow assist device includes a bifurcated anchor to resist dislodgement within a patient's aorta.

FIG. 17B illustrates yet another embodiment of an anchoring mechanism where the proximal end of the hemodynamic flow assist device 1700 includes a bifurcated anchor 1756 to resist dislodgement within a patient's aorta 1740. In one embodiment, the anchor 1756 is manufactured using a shape memory alloy, such as Nitinol. In other embodiments, the anchor 1756 is manufactured using any biocompatible metal. The anchor 1756 may be attached to the proximal end of device 1700, such that the anchor 1756 bifurcates after inserting device 1700 in aorta 1750. In one embodiment, a release mechanism is operated to enable bifurcation of the anchor 1756 once it is in the aorta 1750. Further, the anchor 1756 is pulled back such that it wedges against an aorto-iliac bifurcation 1754. Anchor 1756 may bifurcate, similar to the arms of a 'V' shape, to enable each arm after bifurcation to respectively sit within each branch of an aortic bifurcation 1754. Aortic bifurcation 1754 could be an iliac bifurcation. As the forked anchor 1756 places each of its arms within one branch of each bifurcated aorta 1754, the chances of caudal migration of device 1700 are reduced.

Removable Pump

In cases, a physician may decide to allow the hemodynamic flow assist device to stay within the aorta for a longer duration. Patients with chronic conditions that require frequent assistance of cardiovascular flow assist devices may prefer to have a hemodynamic flow assist device deployed for a longer duration. However, devices that remain deployed for a longer duration, such as for more than five weeks, remain in contact with blood vessels and walls of the aorta. It is likely that within this period, tissues grow in to the cage of the device during its deployment, thus making it difficult to subsequently remove the device.

In an embodiment, the cage of the hemodynamic flow assist device can be separated from the remaining components of the device. Consequently, the cage can be allowed to stay within the aorta, functioning as a stent, while the remaining components of the device are removed. In an embodiment, the pump(s), impeller, shaft, and the distal-end cap are removed with the help of a sheath, while the cage remains at the deployed location within the aorta in its expanded state.

Figure 18A:
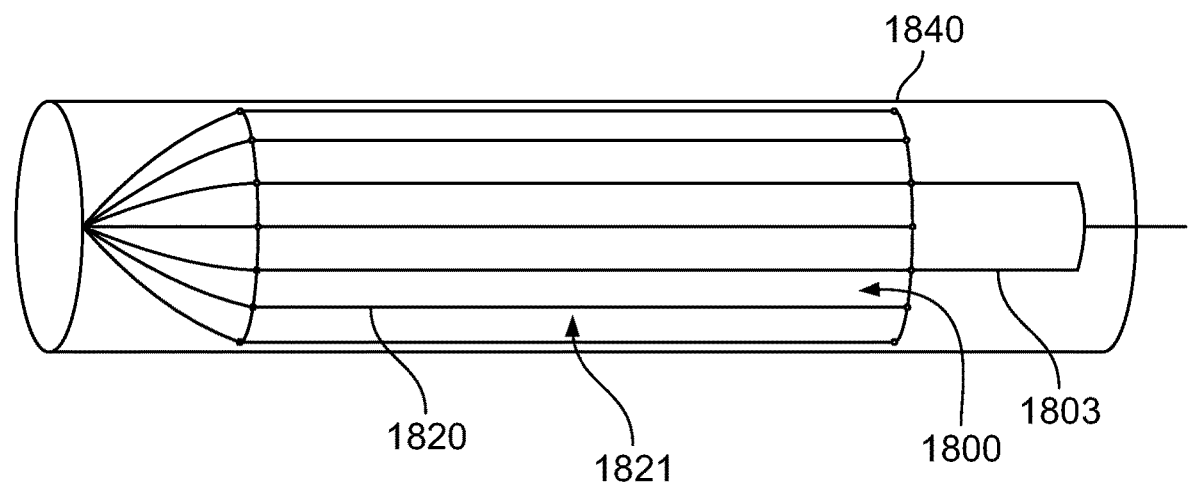
FIG. 18A illustrates the operation of exemplary engagement and release mechanisms to separate the cage from the remaining device, in accordance with an embodiment of the present specification.
Figure 18B:
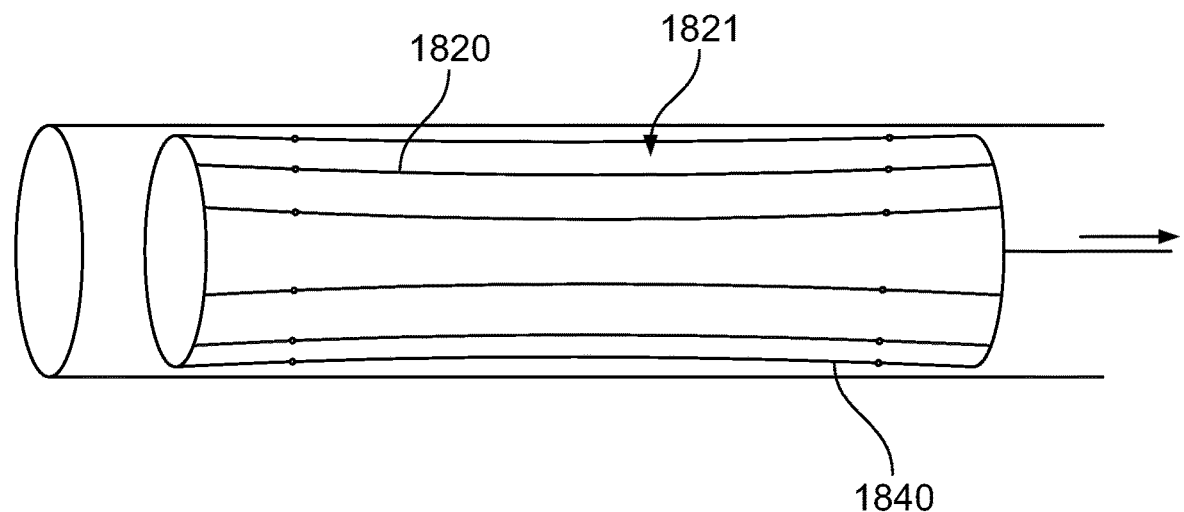
FIG. 18B illustrates the operation of exemplary engagement and release mechanisms, also shown in FIG. 19A, to separate the cage from the remaining device, in accordance with an embodiment of the present specification.

FIGS. 18A and 18B illustrate the operation of exemplary engagement and release mechanisms to separate a cage 1821 from the remaining device, in accordance with an embodiment of the present specification. Cage 1821 is formed by cage support members 1820. The engagement mechanism may include one or more hooks that engage the pump with the cage 1821 while the release mechanism may include a device which interacts with said engagement mechanism via the proximal end of the pump 1803 or cage 1821 to disengage the engagement mechanism, disengaging and releasing the pump 1803 from the cage 1821. FIG. 18A illustrates the cage 1821 within an aorta 1840 when the pump 1803 and other components of the device 1800 are together. In one embodiment, the engagement mechanism is provided between the junction of the pump 1803 and the cage 1821 to allow for release of the pump 1803 from the cage 1821. FIG. 18B illustrates the cage 1821 within the aorta 1840 after the pump 1803 and other device components are withdrawn and removed. In embodiments, the other device components that are attached to the pump 1803 are removed with the pump 1803. In the embodiment, the cage 1821 that remains behind in the aorta 1840 functions similar to a stent.

Figure 19A:
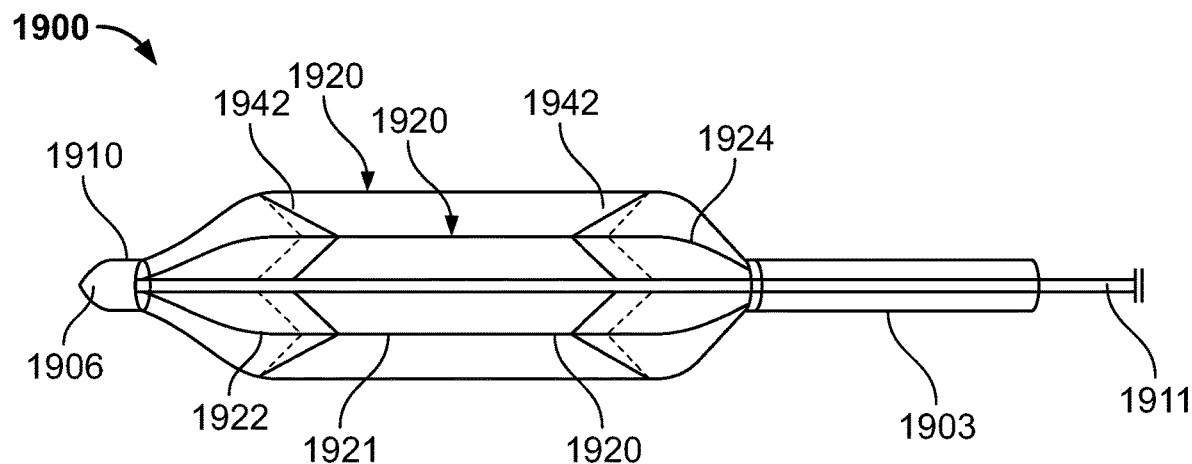
FIG. 19A illustrates an exemplary embodiment of a cage within an aorta integrated with a pump and other components of the hemodynamic flow assist device.

FIGS. 19A, 19B, 19C, and 19D illustrate the operation of exemplary engagement and release mechanisms. FIG. 19A illustrates an exemplary embodiment of a cage formed by cage support members 1920, within an aorta, integrated with a pump 1903 and other various components of a hemodynamic flow assist device 1900. Cage support members 1920 encircle the pump 1903. Cage support members 1920 comprise at least struts 1921 and connectors 1942. Cage support members 1920 further include hinge portions 1922 and 1924, with a distal cap 1906 at the distal end 1910 of device 1900, and with an inner shaft portion 1911 of the pump 1903 at the proximal end 1912 of the device 1900. Struts 1921 are central, thin rectangular shaped portions with proximal and distal ends which link through the distal and proximal hinge portions 1922 and 1924, respectively, to allow for compression and expansion of the cage support members 1920. Connectors 1942 form a sinusoidal structure along the circumference of the cage at both a distal end 1910 and a proximal end 1912. The device includes both proximal and distal connectors 1942. In various embodiments, each of the proximal connectors 1942 comprises a first end and a second end wherein said first end and second end are secured to proximal ends of adjacent struts 1921. Each of said distal connectors 1942 comprises a first end and a second end and said first end and second end are secured to distal ends of adjacent struts 1921. The connectors 1942 are secured at a point on each side (distal and proximal) of each strut 1921 in a contiguous manner. In one embodiment, connectors 1942 are welded to the struts 1921. In an alternative embodiment, the entire cage, including struts 1921 and connectors 1942, is laser cut from a single nitinol cylinder.

In embodiments, the struts 1921, hinge portions 1922 and 1924, and connectors 1942 are manufactured using a shape memory alloy such as Nitinol. In an embodiment, device 1900 comprises eight cage support members 1920, which connect struts 1921 to the proximal and distal ends each with eight hinge portions 1924 and 1922, respectively, which are further connected with elongated portions of the cage support members 1920. In an embodiment, the struts 1921 are discrete. In an embodiment, struts 1921 through hinge portions 1922 are welded to the distal end of the device 1900. In an embodiment, the struts 1921 through hinge portions 1924 are attached to a plate or a housing that encloses the motor of pump 1903 at the proximal end of the device 1900. In an embodiment, hinge portions are attached to the plate with a mechanical bevel and repository attachment that links when compressed together, and detaches when pulled apart.

Figure 19B:
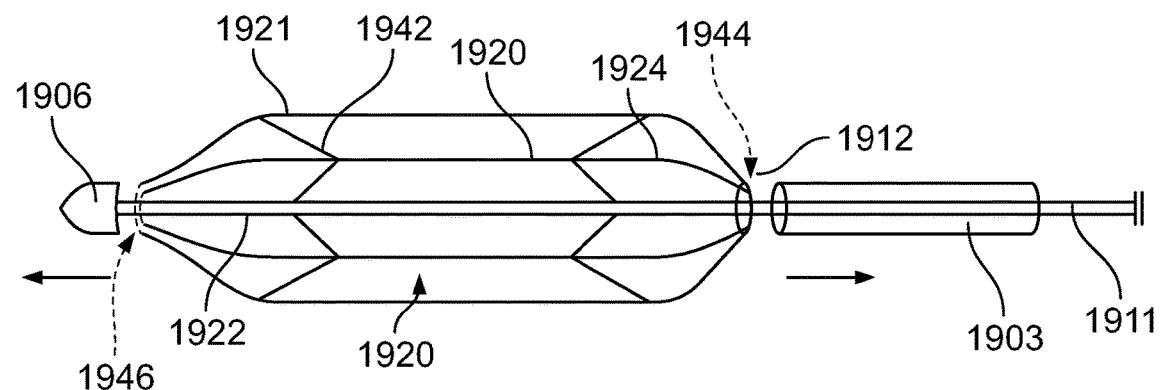
FIG. 19B illustrates an exemplary embodiment of the hemodynamic flow assist device showing an engagement mechanism and a release mechanism in operation to release the cage.

In some embodiments, the release mechanism comprises a central release mechanism within the inner shaft portion 1911 of the pump 1903 of the device 1900. The release mechanism may be controlled from a proximal end of the inner shaft portion 1911 of the pump 1903. FIG. 19B illustrates an exemplary embodiment of the device 1900 where the release mechanism is operated to release the cage support members 1920. The device 1900 further includes one or more engagement mechanisms, comprising proximal couplers 1944 and distal couplers 1946, that engage the pump 1903 with the cage. In an embodiment, a release mechanism on the inner shaft portion 1911 is configured to interact with the couplers 1944, 1946 on the cage support members 1920. In operation, the inner shaft 1911 elongates and releases the proximal couplers 1944 and the distal couplers 1946. In another embodiment, the struts 1921 are clipped with an engagement mechanism comprising a circular bevel in order to attach them to the distal end of the device 1900. In one embodiment, the engagement mechanism further comprises a convex bevel on the outside of the proximal and distal ends of the struts 1921 which dislodges from a concave repository in the inside of the proximal and distal caps when they are pulled apart due to an elongating inner shaft 1911. In embodiments, the components of device 1900, excluding the cage support members 1920, and including the pump 1903 and the distal end cap 1906, are connected to the inner shaft 1911. The release mechanism is activated to disengage the engagement mechanism, disengaging and releasing all of the components of the device 1900 from the cage support members 1920 along with the shaft 1911. In other words, the struts 1921 and hinge members 1922 and 1924 decouple from the inner shaft 1911 and the components attached to the shaft 1911.

Figure 19C:
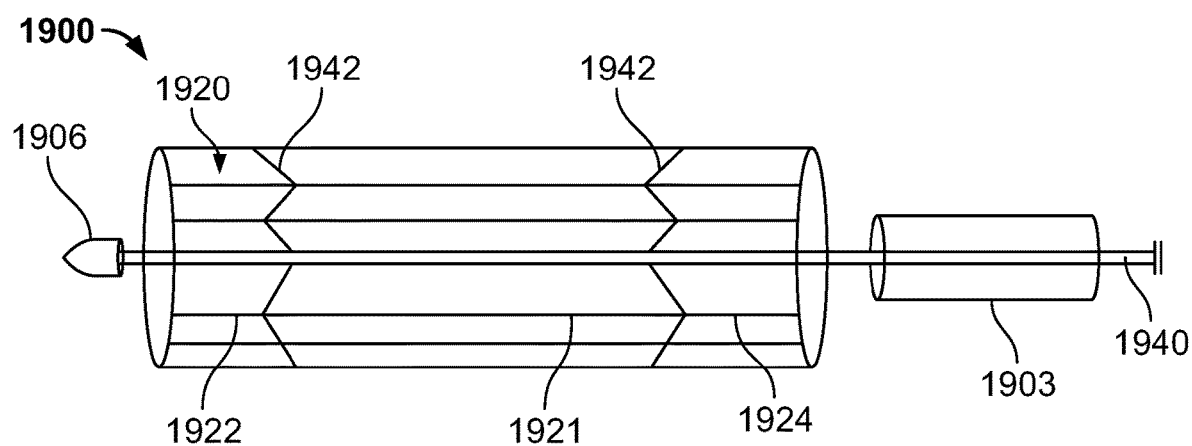
FIG. 19C illustrates an exemplary embodiment of the hemodynamic flow assist device showing the cage separated from the other components.

FIG. 19C illustrates an exemplary embodiment of the device 1900 where the releasing mechanism 1940 has separated the cage supporting members 1920 from the remaining components of the device 1900. Once released, self-expanding nitinol struts 1921 and hinge members 1922, 1924 expand and contact the vessel wall like the rest of the cage. At this point, the connectors 1942, connecting struts 1921, also expand and begin to change from a sinusoidal formation to a linear formation around cage supporting members 1920.

Figure 19D:
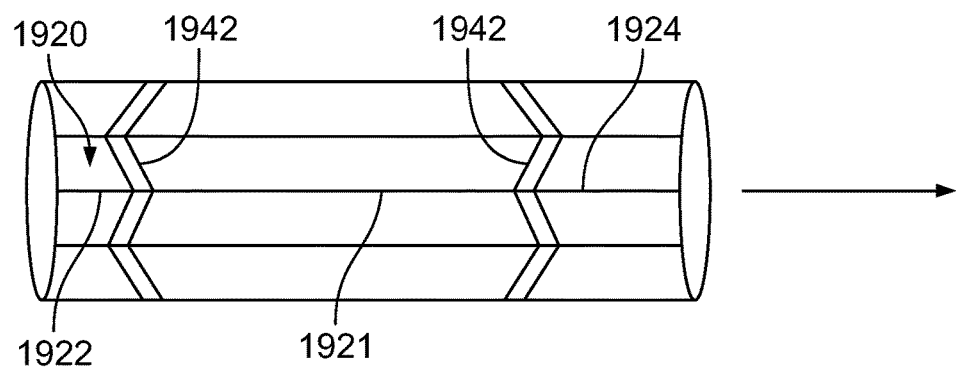
FIG. 19D illustrates an exemplary embodiment of the cage, retained within the vessel and having only the pump removed.

FIG. 19D illustrates an exemplary embodiment of the cage supporting members 1920 that remains within the vessel. The inner shaft 1911, the pump 1903, and the remaining components of the device 1900 are pulled out along with the releasing mechanism. In some embodiments, the cage supporting members 1920 are allowed to stay within the vessel for a period of 90 days. In some embodiments, the cage is allowed to stay within the vessel for less than or more than 90 days and for a period up to six months. In embodiments, the self-expanding cage, post removal of all the other components of the device 1900, expands to form a hollow cylinder that is positioned within the vessel and functions similar to a stent.

Figure 20A:
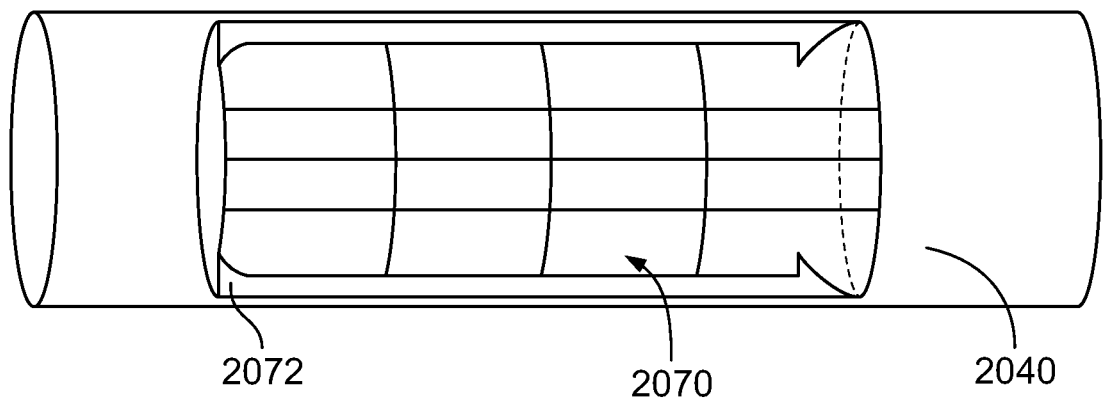
FIG. 20A illustrates an aortic stent with internal hooks, in accordance with an embodiment of the present specification.
Figure 20B:
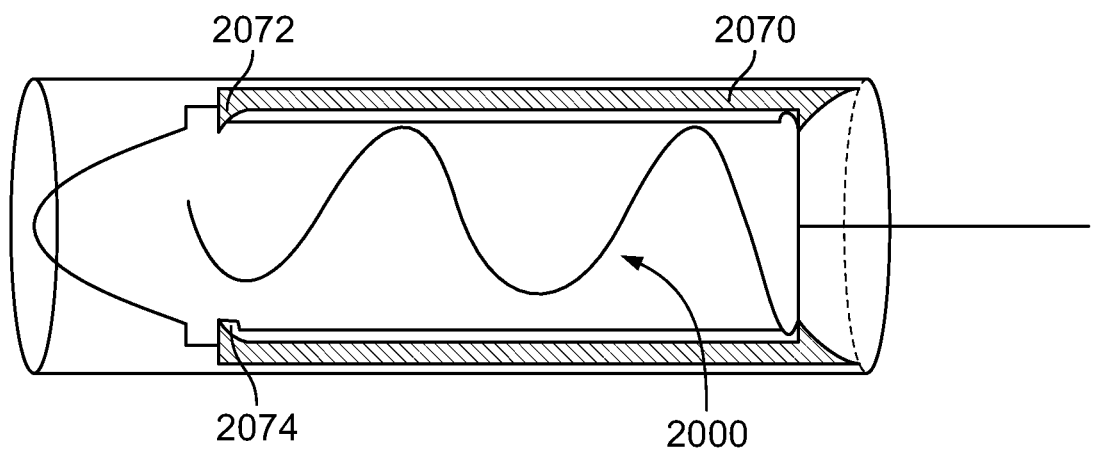
FIG. 20B illustrates a device anchored within the aortic stent with internal hooks of FIG. 20A, in accordance with an embodiment of the present specification.

In another embodiment, the device 1900 is positioned within a removable stent that was previously embedded within the aorta of a patient. FIG. 20A illustrates an aortic stent 2070 with an engagement mechanism comprising internal hooks 2072, in accordance with an embodiment of the present specification. The stent 2070 is positioned inside an aorta 2040. In an embodiment, there are at least four hooks 2072, two each on a proximal and a distal end of the stent 2070. In alternative embodiments, the numbers of hooks 2072 vary. FIG. 20B illustrates a retrievable pump device 2000 anchored within the aortic stent 2070 with internal hooks 2072 of FIG. 20A, in accordance with an embodiment of the present specification. In one embodiment, the engagement mechanism further comprises recesses 2074 positioned on the retrievable pump device 2000 which compliment hooks 2072 such that the retrievable pump device 2000 engages and couples with the stent 2070 once positioned inside the stent 2070. In other embodiments, the attachment of the retrievable pump device 2000 to the inside of the aortic stent 2070 may also be accomplished by non-mechanical means, such as an engagement mechanism comprising positioning magnets of opposing poles positioned on the stent and in the retrievable pump device. In embodiments, the retrievable pump device 2000 comprises the pump and the housing that engages with the cage that was left to remain inside aorta 2040. The hooks 2072 and recesses 2074 in the proximal and distal ends help engage and disengage the pump during insertion and removal from the aorta 2040.

Cage and Pump Occupying Only Partial Lumen in the Aorta

In cases, femoral access may be desired after embedding and deploying a hemodynamic flow assist device. However, presence of the device in the aorta may obstruct access by other medical devices such as catheters.

Figure 21A:
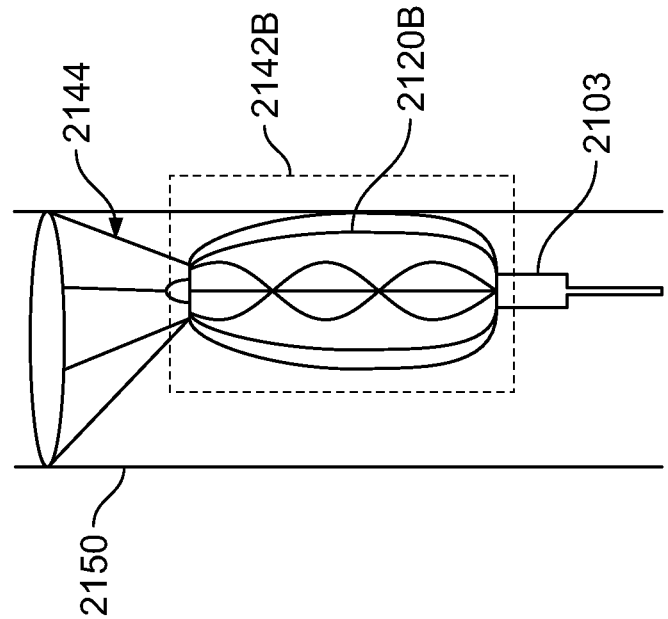
FIG. 21A illustrates an exemplary configuration of a hemodynamic flow assist device deployed in an aorta that allows access for other devices, in accordance with an embodiment of the present specification.

FIG. 21A illustrates an exemplary configuration of a hemodynamic flow assist device deployed in an aorta 2150 that allows access for other devices, in accordance with an embodiment of the present specification. A cage 2142A is configured with cage support members 2120A that are far apart in order to provide a large gap within cage 2142A. Cage 2142A is shaped asymmetrically so that device components within the cage are aligned on one side of the cage, leaving a gap on the other side for other medical devices to pass through.

Figure 21B:
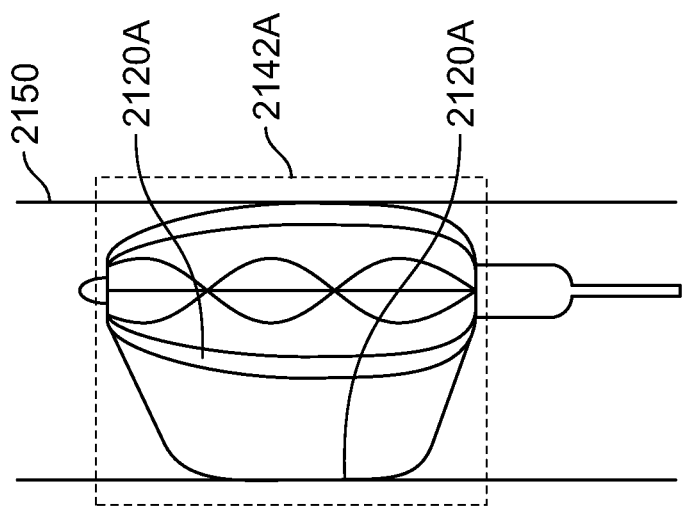
FIG. 21B illustrates another exemplary configuration of a hemodynamic flow assist device deployed in aorta that allows access for other devices, in accordance with an embodiment of the present specification.

FIG. 21B illustrates another exemplary configuration of a hemodynamic flow assist device deployed in aorta 2150 that allows access for other devices, in accordance with an embodiment of the present specification. The device and its cage 2142B are designed to align along one side of the longitudinal axis of aorta 2150. Cage support members 2120B are symmetrically spaced around internal components of the device, including the pump(s) and the impeller. However, some of cage support members 2120B are not in contact with the inner wall of aorta 2150. Distal end of the device is attached to a funnel 2144. A proximal end of funnel 2144, which includes the narrow opening, may include a hook, or any other attachment mechanism, that connects funnel 2144 to the device. The distal end of funnel 2144, which includes the broader opening, faces away from the device. Opening at the distal end of funnel 2144 allows access to other medical devices, through aorta 2150. In an embodiment, pump 2103 is operated at a relatively higher speed than the pump disclosed in alternative embodiments of the present specification. In one embodiment, pump 2103 is operated at 10,000 RPMs. A higher speed of pump 2103 may ensure that sufficient blood flow is maintained through the device, despite the device occupying only a fraction of aorta 2150 along its longitudinal axis.

In an embodiment, the distal end of funnel 2144, with the broader opening, is configured with a one-way flap, or a diaphragm that allows for movement in the proximal direction. The flap or the diaphragm will allow other medical devices to go through the funnel, but do not allow the blood to flow through to the other side (distal) of the flap/diaphragm.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A retrievable intravascular hemodynamic flow assist device comprising:
   a pump comprising:
      a plurality of collapsible blades attached to a rotatable shaft; and
      a motor configured to coaxially rotate said shaft;
   a collapsible cage enclosing said pump; and
   an engagement mechanism configured to engage said pump with said cage;
   wherein said device has a first diameter in an undeployed configuration and a second diameter in a deployed configuration, wherein the second diameter is greater than the first diameter,
   wherein said blades and said cage are positioned against said shaft when the device is in the undeployed configuration, and wherein said blades expand away from said shaft and said cage expands away from said shaft to surround said blades when the device is in said deployed configuration, and
   wherein said engagement mechanism is configured to disengage said pump from said cage, upon activation of a release mechanism, such that said pump is capable of being retrieved from a blood vessel of a patient while said cage remains within said blood vessel.

2. The hemodynamic flow assist device of claim 1, wherein said engagement mechanism comprises at least one hook.

3. The hemodynamic flow assist device of claim 1, wherein said engagement mechanism is provided at a junction of said pump with said cage.

4. The hemodynamic flow assist device of claim 1, wherein said cage is configured to function as a stent after retrieval of said pump.

5. The hemodynamic flow assist device of claim 1, wherein said cage comprises a plurality of cage support members comprising a plurality of struts, proximal and distal hinge portions, and proximal and distal connectors.

6. The hemodynamic flow assist device of claim 5, wherein each of said plurality of struts is rectangular shaped and links one of said plurality of proximal hinge portions with one of said plurality of distal hinge portions to allow for compression and expansion of said cage as said device changes from said undeployed configuration to said deployed configuration.

7. The hemodynamic flow assist device of claim 5, wherein each of said plurality of proximal connectors comprises a first end and a second end wherein said first end and second end are secured to proximal ends of adjacent struts of said plurality of struts and each of said plurality of distal connectors comprises a first end and a second end and said first end and second end are secured to distal ends of adjacent struts of said plurality of struts to create a contiguous structure at a proximal end and a distal end of the cage.

8. The hemodynamic flow assist device of claim 6, wherein each of said plurality of connectors is welded to each of said plurality of struts.

9. The hemodynamic flow assist device of claim 6, wherein said plurality of struts, proximal and distal hinge portions, and proximal and distal connectors are laser cut from a single Nitinol cylinder.

10. The hemodynamic flow assist device of claim 5, wherein said cage comprises eight support members.

11. The hemodynamic flow assist device of claim 1, wherein said release mechanism comprises a central release mechanism positioned within said shaft and is controlled from a proximal end of said shaft.

12. The hemodynamic flow assist device of claim 1, wherein said engagement mechanism comprises a plurality of proximal couplers and a plurality of distal couplers configured to secure said pump to said cage.

13. The hemodynamic flow assist device of claim 12, wherein said shaft is elongated to release said plurality of proximal couplers and said plurality of distal couplers.

14. The hemodynamic flow assist device of claim 5, further comprising a proximal cap and a distal cap, wherein said engagement mechanism comprises a plurality of convex bevels on an outer surface of proximal and distal ends of said struts which are configured to dislodge from a plurality of concave repositories inside said proximal and distal caps when said shaft is elongated.

15. The hemodynamic flow assist device of claim 1, further comprising at least one sensor and a microprocessor, wherein said at least one sensor and microprocessor are configured to monitor data representative of a shape and size of said cage in said deployed configuration and said microprocessor is configured to control said motor to adjust a shape and size of said cage based on said data.

16. The hemodynamic flow assist device of claim 1 wherein said cage is configured to remain in a blood vessel for a period up to six months after retrieval of said pump.

17. A retrievable intravascular hemodynamic flow assist device comprising:
a retrievable helical screw pump comprising:
a first shaft having a lumen, a proximal end, and a distal end, said first shaft comprising a plurality of blades forming a helical screw pump;
a second shaft having a proximal end and a distal end, wherein a portion of said proximal end of said second shaft is disposed within, and configured to telescope into and out of, a portion said lumen of said first shaft at the distal end of said first shaft; and
a motor positioned at said proximal end of said first shaft for coaxially rotating said first shaft and said blades about said second shaft to pump blood through the device;
a cage enclosing said helical screw pump and comprising a plurality of cage support members; and
an engagement mechanism configured to engage said helical screw pump with said cage;
wherein said device has a first diameter in an undeployed configuration and a second diameter in a deployed configuration, wherein the second diameter is greater than the first diameter,
wherein said plurality of blades and said plurality of cage support members are positioned against said first shaft when the device is in the undeployed configuration, and wherein said blades expand away from said first shaft and said cage support members expand away from said first shaft to form a cage surrounding said blades when the device is in said deployed configuration, and
wherein said engagement mechanism is configured to disengage said helical screw pump from said cage, upon activation of a release mechanism, such that said helical screw pump is capable of being retrieved from a blood vessel of a patient while said cage remains within said blood vessel.

18. A retrievable intravascular hemodynamic flow assist device comprising:
a retrievable helical screw pump comprising:
a first shaft having a lumen, a proximal end, and a distal end, said first shaft comprising a plurality of blades forming a helical screw pump;
a second shaft having a proximal end and a distal end, wherein a portion of said proximal end of said second shaft is disposed within, and configured to telescope into and out of, a portion said lumen of said first shaft at the distal end of said first shaft; and
a motor positioned at said proximal end of said first shaft for coaxially rotating said first shaft and said blades about said second shaft to pump blood through the device;
a stent enclosing said helical screw pump; and
an engagement mechanism configured to engage said helical screw pump with said stent, wherein said engagement mechanism is configured to disengage said pump from said stent, upon activation of a release mechanism, such that said pump is capable of being retrieved from a blood vessel of a patient while said stent remains within said blood vessel.

19. The hemodynamic flow assist device of claim 18, wherein said engagement mechanism comprises at least a first hook positioned on a proximal end of said stent and at least a second hook positioned on a distal end of said stent and wherein each of the at least one first hook and at least one second hook is configured to engage with a plurality of recesses positioned in a proximal end of the helical screw pump and a distal end of the helical screw pump respectively.

20. The hemodynamic flow assist device of claim 18, wherein said engagement mechanism comprises a plurality of magnets of opposing poles positioned on said stent and on said helical screw pump.

\* \* \* \* \*